(12) United States Patent
Labrie

(10) Patent No.: US 7,429,576 B2
(45) Date of Patent: Sep. 30, 2008

(54) MEDICAL USES OF A SELECTIVE ESTROGEN RECEPTOR MODULATOR IN COMBINATION WITH SEX STEROID PRECURSORS

(75) Inventor: Fernand Labrie, Sainte-foy (CA)

(73) Assignee: Endorecherche, Inc. (CA)

( * ) Notice: Subject to any disclaimer, the term of this patent is extended or adjusted under 35 U.S.C. 154(b) by 450 days.

(21) Appl. No.: 10/749,981

(22) Filed: Dec. 30, 2003

(65) Prior Publication Data

US 2004/0157812 A1    Aug. 12, 2004

Related U.S. Application Data

(60) Division of application No. 09/330,799, filed on Jun. 11, 1999, now Pat. No. 6,670,346, which is a continuation-in-part of application No. 09/096,284, filed on Jun. 11, 1998, now Pat. No. 6,465,445.

(51) Int. Cl.
    *A61K 31/56*    (2006.01)
    *A61K 31/35*    (2006.01)
    *A61K 31/38*    (2006.01)

(52) U.S. Cl. .................. 514/177; 514/169; 514/171; 514/456; 514/448

(58) Field of Classification Search .................. 514/17, 514/171, 177, 456, 448, 169
See application file for complete search history.

(56) References Cited

U.S. PATENT DOCUMENTS

| 3,742,951 | A |   | 7/1973  | Zaffaroni |         |
|-----------|---|---|---------|-----------|---------|
| 3,797,494 | A |   | 3/1974  | Zaffaroni |         |
| 4,005,200 | A | * | 1/1977  | Utsumi et al. | 514/178 |
| 4,496,556 | A |   | 1/1985  | Orentreich |        |
| 4,542,129 | A |   | 9/1985  | Orentreich |        |
| 4,568,343 | A |   | 2/1986  | Leeper    |         |
| 4,624,665 | A |   | 11/1986 | Nuwayser  |         |
| 4,666,441 | A |   | 5/1987  | Andriola  |         |
| 4,920,115 | A |   | 4/1990  | Nestler et al. | 514/178 |
| 5,064,654 | A |   | 11/1991 | Berner    |         |
| 5,071,644 | A |   | 12/1991 | Viegas    |         |
| 5,071,657 | A |   | 12/1991 | Oloff     |         |
| 5,135,480 | A |   | 8/1992  | Bannon    |         |
| 5,154,922 | A |   | 10/1992 | Govil     |         |
| 5,162,037 | A |   | 11/1992 | Whitson-Fischman |  |
| 5,354,861 | A |   | 10/1994 | Sim       |         |
| 5,362,720 | A |   | 11/1994 | Labrie    |         |
| 5,389,646 | A |   | 2/1995  | Labrie    |         |
| 5,391,557 | A |   | 2/1995  | Cullinan  |         |
| 5,393,763 | A |   | 2/1995  | Black     |         |
| 5,393,785 | A |   | 2/1995  | Labrie    |         |
| 5,395,842 | A |   | 3/1995  | Labrie    |         |
| 5,407,947 | A |   | 4/1995  | Bryant et al. | 514/320 |
| 5,446,071 | A |   | 8/1995  | Grese     | 514/307 |
| 5,489,587 | A |   | 2/1996  | Fontana   |         |
| 5,523,309 | A |   | 6/1996  | Bryant    |         |
| 5,550,107 | A |   | 8/1996  | Labrie    |         |
| 5,567,828 | A |   | 10/1996 | Dodge     |         |
| 5,686,465 | A |   | 11/1997 | Labrie    |         |
| 5,728,688 | A |   | 3/1998  | Labrie    |         |
| 5,840,735 | A |   | 11/1998 | Labrie et al. |     |
| 5,843,984 | A |   | 12/1998 | Clay et al. | 514/443 |
| 6,465,445 | B1 |  | 10/2002 | Labrie    | 514/171 |
| 6,511,970 | B1 | * | 1/2003  | Rodriguez | 514/179 |
| 6,670,346 | B1 |  | 12/2003 | Labrie    | 514/171 |
| 7,005,428 | B1 |  | 2/2006  | Labrie    | 514/171 |

FOREIGN PATENT DOCUMENTS

| DE | 3826297 A1 | 2/1989 |
| DE | 4401554 A1 | 8/1994 |
| EP | 279982     | 8/1988 |
| EP | 635264     | 1/1995 |
| EP | 651998 A1  | 5/1995 |
| EP | 652002 A1  | 5/1995 |
| EP | 652007 A1  | 5/1995 |
| EP | 657162     | 6/1995 |
| EP | 665015 A2  | 8/1995 |

(Continued)

OTHER PUBLICATIONS

Blum et al. The influence of topical vaginal estrogen application on the lipids metabolism Gynecol. obstet. Invest. 15: 10-15 (1983) pp. 10-15.*

(Continued)

*Primary Examiner*—Jennifer Kim
(74) *Attorney, Agent, or Firm*—OStrolenk, Faber, Gerb & Soffen, LLP

(57) ABSTRACT

Novel methods for the medical treatment and/or inhibition of the development of osteoporosis, breast cancer, hypercholesterolemia, hyperlipidemia or atherosclerosis in susceptible warm-blooded animals including humans involving administration of selective estrogen receptor modulator particularly compounds having the general structure:

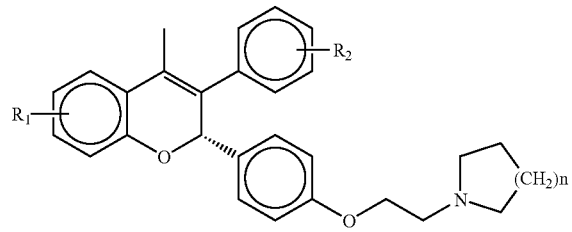

and an amount of a sex steroid precursor selected from the group consisting of dehydroepiandrosterone, dehydroepiandrosterone sulfate, androst-5-ene-3β, 17β-diol and compounds converted in vivo to one of the foregoing presursor. Further administration of bisphosphonates in combination with selective estrogen receptor modulators and/or sex steroid precursor is disclosed for the medical treatment and/or inhibition of the development of osteoporosis. Pharmaceutical compositions for delivery of active ingredient(s) and kit(s) useful to the invention are also disclosed.

1 Claim, 17 Drawing Sheets

FOREIGN PATENT DOCUMENTS

| | | |
|---|---|---|
| EP | 674903 A1 | 10/1995 |
| EP | 693285 A2 | 1/1996 |
| EP | 703231 | 3/1996 |
| EP | 712628 | 5/1996 |
| EP | 724881 A1 | 8/1996 |
| EP | 729955 | 9/1996 |
| EP | 747380 A1 | 12/1996 |
| EP | 0 781 555 | 7/1997 |
| EP | 791591 A1 | 8/1997 |
| EP | 793961 A1 | 9/1997 |
| EP | 801066 A1 | 10/1997 |
| EP | 802183 A1 | 10/1997 |
| EP | 802184 A1 | 10/1997 |
| EP | 806420 A1 | 11/1997 |
| GB | 1 246 639 | 9/1971 |
| GB | 2 185 187 | 7/1987 |
| HU | P 99 002847 | 1/1992 |
| HU | 208150 | 8/1993 |
| HU | P 95 00229 | 5/1996 |
| HU | P 95 01985 | 7/1996 |
| HU | P 98 01230 | 6/1999 |
| JP | A-8-505629 | 6/1996 |
| JP | A-10-36347 | 2/1998 |
| JP | A-10-147522 | 6/1998 |
| JP | A-10-511961 | 11/1998 |
| JP | A-11-500133 | 1/1999 |
| JP | A-2000-505444 | 5/2000 |
| WO | WO 8601105 | 2/1986 |
| WO | WO 9010462 | 9/1990 |
| WO | WO 9300070 | 1/1993 |
| WO | WO 93/10741 | 6/1993 |
| WO | WO 9416709 | 8/1994 |
| WO | WO 9600041 | 1/1996 |
| WO | WO 96/05833 | 2/1996 |
| WO | WO 9605824 | 2/1996 |
| WO | WO 9605825 | 2/1996 |
| WO | WO 9605829 | 2/1996 |
| WO | WO 9607402 | 3/1996 |
| WO | WO 9609040 | 3/1996 |
| WO | WO 9616646 | 6/1996 |
| WO | WO 9626201 | 8/1996 |
| WO | WO 9725034 | 7/1997 |
| WO | WO 9725035 | 7/1997 |
| WO | WO 9725036 | 7/1997 |
| WO | WO 9725037 | 7/1997 |
| WO | WO 9725038 | 7/1997 |
| WO | WO 9732837 | 9/1997 |
| WO | WO 98/58948 | 12/1998 |
| WO | WO 99/59581 | 11/1999 |
| WO | WO 99/63973 | 12/1999 |

OTHER PUBLICATIONS

Calin Chen et al., "Adrenal Steroid Precursors Exert Potent Androgenic Action in the Hamster Sebaceous Glands of Flank Organs and Ears", Endocrinology 137: 1752-1757, 1996.

Claude Labrie et al., "Stimulation of Androgen-Dependent Gene Expression by the Andrenal Precursors Dehydroepiandrosterone and Androstenedione in the Rat Ventral Prostate", Endocrinology 124: 2745-2754, 1989.

Claude Labrie et al., "Androgenic Activity of Dehydroepiandrosterone and Androstenedione in the Rat Ventral Prostate", Endocrinology 123: 1412-1417, 1988.

Delmas et al., N. Engl. J. Med., Dec. 4, 1997; vol. 337(23), pp. 1641-1647.

N. Engl. J. Med., 1998, vol. 319, pp. 1681-1692.

F. Labrie et al., "DHEA and the Intracrine Formation of Androgens and Estrogens in Peripheral Target Tissues: Its Role During Aging," Steroids, 53:322-328 (1998).

F. Labrie et al., "Interactions Between Estrogens, Androgens, Progestins, and Glucocorticoids in ZR-75-1 Human Breast Cancer Cells," Annals New York Academy of Sciences, pp. 130-148, 1990.

S. Luo et al., "Prevention of Development of Dimethylbenz(a)anthracene (DMBA)—Induced Mammary Tumors in the Rat by the New Nonsteroidal Antiestrogen EM-800 (SCH57050)," Breast Cancer Research and Treatment, 49:1-11 (1998).

Schwartz et a., "Dehydroepiandrosterone: an anti-obesity and anti-carcinogenic agent", Nutr. Cancer 1981, 31 (1), 46-53 ISSN: 01635581.

Couillard, S,; Labrie, C.; Gauthier, S.; Labrie, F., Abstract, Maturitas, (1997), vol. 27, No. SUPPL., pp. 80, Title: "Inhibitory Effect of a new Non-Steroidal Pure Antiestrogen (EM-800) in Combination with DHEA on Human ZR-75-1 Breast Tumors in Nude Mice".

Adami, S., Baroni, M.C., Broggini, M., Carratelli, L., Caruso, I., Gnessi, L., laurenzi, M., Lombardi, A., Norbiato, G., Ortolani, S., Ricerca, E., Romanini, L., Subrizi, S., Weinberg, J., Yates, A.J. (1993) Treatment of postmenopausal osteoporosis with continuous daily oral alendronate in comparison with either placebo or intranasal salmon calcitonin. Osteoporosis Int. (Suppl.), 3: S21-S27.

Adams, J., Garcia, M., Rochefort, H. (1981 Estrogenic effects of physiological concentrations of 5-androstene-3β,17b-diol and its metabolism in MCF7 human breast cancer cells. Cancer Res., 41: 4720-4926.

Alison, R.H., Morgan, K.T., Montgomery Jr, C.A. Chapter 26: Ovary. In: Boorman, G.A., Eutis, S.L., Elwell, M.R., Montgomery Jr, C.A. and MacKenzie, W.F., eds, Pathology of the Fischer Rat, pp. 429-442, San Diego: Academic Press, 1990.

Arad, Y., Badimon, J.J., Badimon, L., Hembree, W.C., Ginsberg, H.N. (1989) Dehydroepiandrosterone feeding prevents aortic fatty streak formation and cholesterol accumulation in cholesterol-fed rabbit. Arteriosclerosis, 9: 159-166.

Asselin, J., Kelly, P.A., Caron, M.G., Labrie, F. (1977) Control of hormone receptor levels and growth of 7,12-dimethylbenz(a)anthracene-induced mammary tumors by estrogens, progesterone and prolactin. Endocrinology, 101: 666-671.

Balena, R., Toolan, B.C., Shea, M., Markatos, A., Myers, E.R., Lee, S.C., Opas, E.E., Seedor, J.G., Klein, H., Frankenfield, D., Quartuccio, H., Fioravanti, C., Clair, J., Brown, E., Hayes, W.C., Rodan, G.A. (1993) The effects of 2-year treatment with the aminobisphosphonate alendronate on bone metabolism, bone histomorphometry and bone strength in ovariectomized nonhuman primates. J. Clin. Invest., 92: 2577-2586.

Baran, D.T., Bergfeld, M.A., Teitelbaum, S.L., Avioli, L.V. (1978) Effect of testosterone therapy on bone formation in an osteoporotic hypogonadal male. Calcif. Tiss. Res., 26: 103-106.

Bardon, S., Vignon, F., Chalbos, D., Rochefort, H. (1985) RU 486, a progestin and glucocorticoid antagonist, inhibits the growth of breast cancer cells via the progesterone receptor. J. Clin. Endocrinol. Metab., 60: 692-697.

Barrett-Connor, E., Khaw, K.T., Yen, S.S.C. (1986) A prospective study of dehydroepiandrosterone sulfate, mortality, and cardiovascular disease. New Engl. J. Med., 315: 1519-1524.

Barrett-Connor, E. (1993) Estrogen and estrogen-progestogen replacement: therapy and cardiovascular diseases. Am. J. Med., 95 (Suppl. 5A): 40S-43S.

Black, L.J., Sato, M., Rowley, E.R., Magee, D.E., Bekele, A., Williams, D.C., Cullinan, G.J., Bendele, R., Kauffman, R.F., Bensch, W.R., Frolik, C.A., Termine, J.D., Bryant, H.U. (1994) Raloxifene (LY 139481 HCI) prevents bone loss and reduces serum cholesterol without causing uterine hypertrophy in ovariectomized rats. J. Clin. Invest., 93: 63-69.

Boonekamp, P.M., van der Wee-Pals, L.J.A., van Wijk-van Lennep, M.M.L., Wil Thesing, C., Bijovet, O.L.M. (1986) Two modes of action of bisphosphonates on osteoclastic resorption of mineralized matrix. Bone Miner., 1: 27-39.

Bruning, P.F., Bonfrer, J.M.G., Hart, A.A.M., de Jong-Bakker, M., Linders, D., von Loon, J., Nooyen, W.J. (1988) Tamoxifen, serum lipoproteins and cardiovascular risk. Br. J. Cancer, 58: 497-499.

Bundgaard, H. (1991) In: P. Krogsgaard-Larsen, H.B., ed. Design and application of prodrugs, Switzerland: Harwood Academic Publishers GmfH, Chur, 113-191.

Burger, H., Hailes, J., Nelson, J. (1987) Effect of combined implants of oestradiol and testosterone on libido in postmenopausal women. Br. Med. J., 294: 936-937.

Carano, A., Teitelbaum, S.L., Konsek, J.D., Schlesinger, P.H., Blair, H.C. (1990) Bisphosphonate directly inhibit the bone resorption activity of isolated avian osteoclasts in vitro. J. Clin. Invest, 85: 456-461.

Cardy, R.H. (1991) Sexual dimorphism of the normal rat mammary gland. Vet. Pathol., 28: 139-145.

Chen, C., Bélanger, A., Labrie, F. (1996) Adrenal steroid precursors exert potent androgenic action in the hamster sebaceous glands of flank organs and ears. Endocrinology, 137: 1752-1757.

Cleary, M., Zisk, J. (1983) Effect of dehydroepiandrosterone (DHEA) in adult zucker rats. Fed. Proc., 42: 536 (abst. 1433).

Colditz, G.A., Hankinson, S.E., Hunter, D.J., Willett, W.C., Manson, J.E., Stampfer, M.J., Hennekens, C., Rosner, B., Speizer, F.E. (1995) The use of estrogens and progestins and the risk of breast cancer in postmenopausal women. N. Engl. J. Med., 332: 1589-1593.

Coleman, D.L., Schwizer, R.W., Leiter, E.H. (1983) Effect of genetic background on the therapeutic effects of dehydroepiandrosterone (DHEA) in diabetes-obesity mutants and in aged normal mice. Diabetes, 33: 26-33.

Conover, W.J. (1980) Contingency tables. Practical nonparametric statistics, 2nd Edition, pp. 153-170. New York: John Wiley & Sons.

Couillard, S., Labrie, C., Bélanger, A., Candas, B., Pouliot, F., Labrie, F. (1998) Effect of dehydroepiandrosterone and the antiestrogen EM-800 on growth of human ZR-75-1 breast cancer xenografts. J. Natl. Cancer Inst. 90: 772-778.

Dauvois, S., Li, S., Martel, C., Labrie, F. (1989) Inhibitory effect of androgens on DMBA-induced mammary carcinoma in the rat. Breast Cancer Res. Treatm., 14: 299-306.

Dauvois, S., Spinola, P.G., Labrie, F. (1989) Additive inhibitory effects of bromocriptine (CB-154) and medroxyprogesterone acetate (MPA) on dimethylbenz(a)anthracene (DMBA)-induced mammary tumors in the rat. Eur. J. Cancer Clin. Oncol., 25: 891-897.

Dauvois, S., Geng, C.S., Lévesque, C., Mérand, Y., Labrie, F. (1991) Additive inhibitory effects of an androgen and the antiestrogen EM-170 on estradiol-stimulated growth of human ZR-75-1 breast tumors in athymic mice. Cancer Res., 51: 3131-3135.

De Fazio, J., Meldrum, D.R., Winer, J.H., Judd, H.L. (1984) Direct action of androgen on hot flushes in the human male. Maturitas, 6: 3-8.

Diamond, P., Cusan, L., Gomez, J.L., Bélanger, A., Labrie, F. (1996) Metabolic effects of 12-month percutaneous DHEA replacement therapy in postmenopausal women. J. Endocrinol., 150: S43-S50.

Dipippo, V.A., Lindsay, R., Powers, C.A. (1995) Estradiol and tamoxifen interactions with thyroid hormone in the ovariectomized-thyroidectomized rat. Endocrinology, 136: 1020-1033.

Draper, M.W., Flowers, D.E., Huster, W.J., Neild, J.A., Harper, K., Arnaud, C. (1996) A controlled trial of raloxifene (LY139481) HCI: impact on bone turnover and serum lipid profile in healthy postmenopausal women. J. Bone Miner. Res., 11: 835-842.

Gallagher, A., Chambers, T.J., Tobias, J.H. (1993) The estrogen antagonist ICI 182780 reduces cancellous bone volume in female rats. Endocrinology, 133:2787-2791.

Gauthier, S., Caron, B., Cloutier, J., Dory, Y.L., Favre, A., Larouche, D., Mailhot, J., Ouellet, C., Schwerdtfeger, A., Leblanc, G., Martel, C., Simard, J., Mérand Y., Bélanger, A., Labrie, C., Labrie, F. (1997) (S)-(+)-4-[7-(2,2-dimethyl-1-oxopropoxy)-4-methyl-2-[4-[2-(1-piperidinyl)ethoxy]phenyl]-2H-1-benzopyran-3-yl]-phenyl 2,2-dimethylpropanoate (EM-800): a highly potent, specific, and orally active non steroidal antiestrogen. J. Med. Chem., 40: 2117-2122.

Gordon, G.B., Bush, D.E., Weisman, H.F. (1988) Reduction of atherosclerosis by administration of dehydroepiandrosterone, J. Clin. Invest, 82: 712-720.

Gordon, G.B., Helzlsouer, K.J., Comstock, G.W. (1991) Serum levels of dehydroepiandrosterone and its sulfate and the risk of developing bladder cancer. Cancer Res., 51: 1366-1369.

Harris, S.T., Gertz, B.J., Genant, H.K., Eyre, D.R., Survill, T.T., Ventura, J.N., DeBrock, J., Ricerca, E., Chesnut III, C.H. (1992) The effect of short term treatment with alendronate on vertebral density and biochemical markers of bone remodeling in early postmenopausal women. J. Clin. Endocrinol. Metab., 76: 1399-1406.

Heaney, R.P., Draper, M.W. (1997) Raloxifen and estrogen: comparative bone-remodeling kinetics. J. Clin. Endocrinol. Metab., 82: 3425-3429.

Hughes, D.E., MacDonald, B.R., Russell, R.G.G., Gowen, M. (1989) Inhibition of osteoclast-like cell formation by bisphosphonates in long-term cultures of human bone marrow. J. Clin. Invest., 83: 1930-1935.

Jordan, V.C., Phelps, E., Lindgren, J.U. (1987) Effects of anti-estrogens on bone in castrated and intact female rats. Breast Cancer Res. Treat., 10: 31-35.

Kaurfman, R.F., Bryant, H.U. (1995) Effective therapeutic management of the postmenopausal state will be a cornerstone in strategies for preserving or improving women's health in the $21^{st}$ century. Selective estrogen receptor modulators. DN & P 8: 531-539.

Ke, H.Z., Simmons, H.A., Pirie, C.M., Crawford, D.T., Thompson, D.D. (1995) Droloxifene, a new estrogen antagonist/agonist, prevents bone loss in ovariectomized rats. Endocrinology, 136: 2435-2441.

Kent, S. (1982) DHEA: "Miracle" drug? Geriatrics, 37: 157-161.

Kleerekoper, M., Villanueva, A.R., Stanciu, J., Sudhaker Rao, R.D., Parfitt, A.M. (1985) The role of three-dimensional trabecular microstructure in the pathogenesis of vertebral compression fractures. Calcif. Tissue Int., 37: 594-597.

Koller, C., Buri, P. (1987) Propriétés et intérêt pharmaceutique des gels thermoréversibles à base de poloxamers et polyxamines. S.T.P. Pharma, 3: 115-124.

Kramer, C.Y. (1956) Extension of multiple range tests to group means with unequal numbers of replications. Biometrics, 12: 307-310.

Kreitmann, B., Bayard, F. (1979) Androgen interaction with the oestrogen receptor in human tissues. J. Steroid Biochem., 11: 1589-1595.

Labrie, F., Dupont, A., Bélanger, A. (1985) Complete blockade for the treatment of prostate cancer. In: De Vita, V.T., Hellman, S., Rosenberg, S.A., ed. Importance Advances in Oncology, pp. 193-217. Philadelphia: J.B. Lippincott Co.

Labrie, F. (1991) Intracrinology. Mol. Cell. Endocrinol., 78: C113-C118.

Labrie, F., Bélanger, A., Simard, J., Luu-The, V., Labrie, C. (1995) DHEA and peripheral androgen and estrogen formation: Intracrinology. Ann. N. Y. Acad. Sci., 774: 16-28.

Labrie, F., Li, S., Labrie, C., Lévesque, C., Mérand, Y. (1995) Inhibitory effect of a steroidal antiestrogen (EM-170) on estrone-stimulated growth of 7,12 dimethylbenz(a)anthracene (DMBA)-induced mammary carcinoma in the rat. Breast Cancer Res. Treat., 33: 237-244.

Labrie, F., Simard, J., Luu-The, V., Bélanger, A., Pelletier, G., Morel, Y., Mebarki, F., Sanchez, R., Durocher, F., Turgeon, C., Labrie, Y., Rhéaume, E., Labrie, C., Lachance, V. (1996) The 3β-hydroxysteroid dehydrogenase/isomerase gene family: lessons from type II 3β-HSD congenital deficiency. In: Hansson, V., Levy, F.O. and Taskén, K., eds, Signal Transduction in Testicular Cells. Ernst Schering Research Foundation Workshop, pp. 185-218. Berlin, Heidelberg, New York: Springer-Verlag.

Labrie, F., Luu-The, V., Lin, S.X., Labrie, C., Simard, J., Breton, R., Bélanger, A. (1997) The key role of 17β-HSDs in sex steroid biology. Steroids, 62: 148-158.

Labrie, F., Bélanger, A., Cusan, L., Candas, B. (1997) Physiological changes in DHEA are not reflected by the serum levels of active androgens and estrogens but of their metabolites: intracrinology. J. Clin. Endocrinol. Metab., 82: 2403-2409.

Labrie, F., Diamond, P., Cusan, L., Gomez, J.L., Bélanger, A. (1997) Effect of 12-month DHEA replacement therapy on bone, vaginum, and endometrium in postmenopausal women. J. Clin. Endocrinol. Metab., 82: 3498-3505.

Lippman, M.E. (1983) Antiestrogen therapy of breast cancer. Semin. Oncol., 10: 11-19.

Love, R.R., Newcomb, P.A., Wiebe, D.A., Surawicz, T.S., Jordan, V.C., Carbone, P.P., DeMets, D.L. (1990) Effects of tamoxifen therapy on lipid and lipoprotein levels in postmenopausal patients with node-negative breast cancer. J. Natl. Cancer Inst., 82: 1327-1332.

Love, R.R., Wiebe, D.A., Newcomb, P.A., Cameron, L., Leventhal, H., Jordan, V.C., Feyzi, J., DeMets, D.L. (1991) Effects of tamoxifen on cardiovascular risk factors in postmenopausal women. Ann. Intern. Med., 115: 860-864.

Lu, K.H., Chang, R.S., Kledzik, G.S. (1979) Daily patterns of ovarian and pituitary hormone secretion in old female rats just prior to the onset of estrous cycle irregularity and during chronic anovulation. 61st Annual Meeting of the Endocrine Society, p. 106, Abst. No. 134.

Lundeen, S.C., Carver, J.M., McKean, M.L., Winneker, R.C. (1997) Characterization of the ovariectomized rat model for the evaluation of estrogen effects on plasma cholesterol levels. Endocrinology, 138: 1552-1558.

Luo, S., Sourla, A., Labrie, C., Bélanger, A., Labrie, F. (1997) Combined effects of dehydroepiandrosterone and EM-800 on bone mass, serum lipids, and the development of dimethylbenz(a)anthracene (DMBA)-induced mammary carcinoma in the rat. Endocrinology, 138: 4435-4444.

Martel, C., Sourla, A., Fournier, M., Picard, S., Li, S., Stojanovic, M., Pelletier, G., Labrie, F. (1998) Predominant androgenic component in the stimulatory effect of dehydroepiandrosterone (DHEA) on bone mineral density in the rat. J. Endocrinol., in press.

Meites, J. (1980) Relation of the neuroendocrine system to the development and growth of experimental mammary tumors. J. Neural. Transmission, 48: 25-42.

Melsen, F., Melsen, B., Mosekilde, L., Bergmann, S. (1978) Histomorphometric analysis of normal bone from the iliac crest. Acta Pathol. Microbiol. Scand., 86: 70-81.

Morales, A.J., Nolan, A.J., Nelson, J.C., Yen, S.C. (1994) Effects of replacement dose of dehydroepiandrosterone in men and women of advancing age. J. Clin. Endocrinol. Metab., 78: 1360-1367.

Mortensen, L., Charles, P., Bekker, P.J., Digennaro, J., Johnston, C.C. (1998) Risedronate increases bone mass in an early postmenopausal population: two years of treatment plus one year of follow-up. J. Clin. Endocrinol. Metab., osteoporosis, 83: 396-402.

Need, A.G., Horowitz, M., Bridges, A., Morris, H.A., Nordin, C. (1989) Effects of nandrolone decanoate and antiresorptive therapy on vertebral density in osteoporotic postmenopausal women. Arch. Intern. Med., 149: 57-60.

Need, A.G., Horowitz, M., Moris, H.A., Walker, C.J., Nordin, B.E.C. (1987) Effects of nadrolone therapy on forearm bone mineral contant in osteoporosis. Clin. Orthop., 225: 273-278.

Odell, W.D., Swerdloff, R.S. (1976) Male hypogonadism. West. J. Med., 124: 446-475.

Papapoulos, S.E., Landman, J.O., Bijvoet, O.L.M., Lowik, C.W.G. M., Valkema, R., Pauwels, E.K.J., Vermeij, P. (1992) The use of biphosphonates in the treatment of osteoporosis. Bone, 13: S41-S49.

Parfitt, A.M. (1984) The cellular basis of bone remodeling: the quantum concept reexamined in light of recent advances in the cell biology of bone. Calcified Tissue International, 36 Suppl. 1: S37-S45.

Parker, C.R., Simpson, E.R., Bilheimer, D.W., Leveno, K., Carr, B.R., MacDonald, P.C. (1980) Inverse relation between low-density lipoprotein-cholesterol and dehydroisoandrosterone sulfate in human fetal plasma. Science, 208: 512-514.

Podenphant, J., Larsen, N.E., Christiansen, C. (1984) An easy and reliable method for determination of urinary hydroxyproline. Clinica Chimica Acta, 142: 145-148.

Poulin, R., Baker, D., Labrie, F. (1988) Androgens inhibit basal and estrogen-induced cell proliferation in the ZR-75-1 human breast cancer cell line. Breast Cancer Res. Treatm., 12: 213-225.

Poulin, R., Labrie, F. (1986) Stimulation of cell proliferation and estrogenic response by adrenal C19-D5-steroids in the ZR-75-1 human breast cancer cell line. Cancer Res., 46: 4933-4937.

Preston Martin, S., Pike, M.C., Ross, R.K., Jones, P.A., Henderson, B.E. (1990) Increased cell division as a cause of human cancer. Cancer. Res., 50: 7415-21.

Reginster, J.Y., Deroisy, R., Denis, D., Collette, J., Lecart, M.P., Sarlet, N., Ethgen, D., Franchimont, P. (1989) Prevention of postmenopausal bone loss by tiludronate. Lancet, 2: 1469-1471.

Rossini, M., Gatti, D., Zamberlan, N., Brage, V., Dorizzi, R., Adami, S. (1994) Long-term effects of a treatment course with oral alendronate of postmenopausal osteoporosis. J. Bone Miner. Res., 9: 1833-1837.

Russell, J.C., Amy, R.M., Graham, S., Wenzel, L,M., Dolphin, P.J. (1993) Effect of castration on hyperlipidemic, insulin resistant JCR: LA-corpulent rats. Atherosclerosis, 100: 113-122.

Russo, I.H., Medado, J., Russo, J. (1989) Endocrine influences on the mammary gland. Monographs on pathology of laboratory animals: integument and mammary glands, pp. 252-266.

Saarto, T., Blomqvist, C., Valimaki, M., Makela, P., Sarna, S., Elomaa, I. (1997) Clodronate improves bone mineral density in post-menopausal breast cancer patients treated with adjuvant antioestrogens. Br. J. Cancer, osteoporosis, 75: 602-605.

Sato, M., Grasser, W., Endo, N., Akins, R., Simmons, H., Thompson, D.D., Golub, E., Rodan, G.A. (1991) Bisphosphonate action. Alendronate localization in rat bone and effects on osteoclast ultrastructure. J. Clin. Invest., 88: 2095-2105.

Schwartz, A.G. (1979) Inhibition of spontaneous breast cancer formation in female C3H (Avy/a) mice by long-term treatment with dehydroepiandrosterone. Cancer Res., 39: 1129-1132.

Sherwin, B.B., Gelfand, M.M. (1984) Effects of parenteral administration of estrogen and androgen on plasma hormone levels and hot flushes in the surgical menopause. Am. J. Obstet. Gynecol., 148: 552-557.

Sherwin, B.B., Gelfand, M.M. (1985) Differential symptom response to parenteral estrogen and/or androgen administration in the surgical menopause. Am. J. Obstet. Gynecol., 151: 153-160.

Sherwin, B.B., Gelfand, M.M. (1987) The role of androgen in the maintenance of sexual functioning in oophorectomized women. Psychosom Med., 49: 397-409.

Sherwin, B.B., Gelfand, M.M., Schucher, R., Gabor, J. (1987) Postmenopausal estrogen and androgen replacement and lipoprotein lipid concentrations. Am. J. Obstet. Gynecol., 156: 414-419.

Sherwin, B.B. (1988) Affective changes with estrogen and androgen replacement therapy in surgically menopausal women. J. Affect. Disord., 14: 177-187.

Sibonga, J.D., Evans, G.L., Hauck, E.R., Bell, N.H., Turner, R.T. (1996) Ovarian status influences the skeletal effects of tamoxifen in adult rats. Breast Cancer Res. Treatm., 41: 71-79.

Simard, J., Labrie, F. (1987) Adrenal C19-5-ene steroids induce full estrogenic responses in rat pituitary gonadotrophs. J. Steroid Biochem. 26: 539-546.

Sledge, G.W., McGuire, W.L. (1983) Steroid hormone receptors in human breast cancer. Adv. Cancer Res., 38: 61-75.

Smith, D.A.S., Walker, M.S. (1976) Changes in plasma steroids and bone density in Klinefelter's syndrome. Calif. Tissue Res., 22 (Suppl.): 225-228.

Sortino, M.A., Wise, P.M. (1989) Effects of age and long term ovariectomy on prolactin secretion, as assessed by the reverse hemolytic plaque assay. Endocrinology, 124: 90-96.

Storm, T., Thamborg, G., Steiniche, T., Genant, H.K., Sorensen, O.H. (1990) Effect of intermittent cyclical etidronate therapy on bone mass and fracture rate in women with postmenopausal osteoporosis. N. Engl. J. Med., 322: 1265-1271.

Svec, F., Richards, R., Porter, J.R. (1997) The effect of dehydroepiandrosterone (DHEA) on lean Zucker rats. 2nd International Conference on Cortisol & Anti-Cortisols, Las Vegas, Nevada, USA, p. 56 (Abst.).

Tang, F.Y., Bonfiglio, T.A., Tang, L.K. (1984) Effect of estrogen and progesterone on the development of endometrial hyperplasia in the Fischer rat. Biol. Reprod., 31: 399-413.

Tchernof, A., Després, J.P., Bélanger, A., Dupont, A., Prud'homme, D., Moorjani, S., Lupien, P.J., Labrie, F. (1995) Reduced testosterone and adrenal C19 steroid levels in obese men. Metabolism, osteoporosis, 44: 513-519.

Thoman, M., Weigle, W. (1989) The cellular and subcellular bases of immunosenescence. Adv. Immunol., 46: 221-260.

Wakeling, A.E. (1993) The future of new pure antiestrogens in clinical breast cancer. Breast Cancer Res. Treat., 25: 1-9.

Walsh, B.W., Schiff, I., Rosner, B., Greenberg, L., Ravnikar, V., Sacks, F.M. (1991) Effects of postmenopausal estrogen replacement on the concentrations and metabolism of plasma lipoproteins. New Engl. J. Med., 325: 1196-1204.

Watts, N.B., Harris, S.T., Genant, H.K., Wasnich, R.D., Miller, P.D., Jackson, R.D., Licata, A.A., Ross, P., Woodson, G.C., Yanover, M.J., Mysiw, J., Kohse, L., Rao, M.B., Steiger, P., Richmond, B., Chesnut III, C.H. (1990) Intermittent cyclical etidronate treatment of postmenopausal osteoporosis. N. Engl. J. Med., 323: 73-79.

Weinstein, R.S., Hutson, M.S. (1987) Decreased trabecular width and increased trabecular spacing contribute to bone loss with aging. Bone, 8: 137-142.

Wilson, T.M., Norris, J.D., Wagner, B.L., Asplin, I., Baer, P., Brown, H.R., Jones, S.A., Henke, B., Sauls, H., Wolfe, S., Morris, D.C., McDonnell, D.P. (1997) Dissection of the molecular mechanism of action of GW5638, a novel estrogen receptor ligand, provides insights into the role of estrogen receptor in bone. Endocrinology, 138: 3901-3911.

Wittliff, J.L. (1984) Steroid-hormone receptors in breast cancer. Cancer, 53: 630-643.

Wolkowitz, O., Reus, V.I., Vinogradov, S., Marco, E., Chan, T., Manfredi, F., Poole, J., Johnson, R., Canick, J., Lichtmacher, J., Keebler, A., Friedland, M., Brizendine, L. (1997) Antiglucocorticoid treatment of depression and schizophrenia: double-blind ketoconazole. 2nd International Conference on Cortisol & Anti-Cortisols, Las Vegas, Nevada, USA, p. 62 (Abst.).

Yen, T.T., Allen, J.A., Pearson, D.V., Acton, J.M. (1977) Prevention of obesity in Avy/a mice by dehydroepiandrosterone. Lipids, 12: 409-413.

Guidelines for preclinical and clinical evaluation of agents used in the prevention or treatment of postmenopausal osteoporosis, Division of Metabolism and Endocrine Drug Products, FDA, May 1994.

abstract of U.S. 5,478,579 Jul. 21, 1993 Sawruk.

abstract of U.S. 5,476,865 Jul. 6, 1994 Panetta.

Minutes of the Endocrinology and Metabolism Drugs Advisory Committee, FDA Thursday, Meeting #68, Nov. 20, 1997.

Sourla, et al., Endocrinology, 139(2):753-764 (1998).

Hackenberg, et al., J. Steroid Biochem., 46(5):597-603 (1993).

Labrie, et al., J. Steroid Biochem., 69:51-84 (1999).

CA 130:108222, Nawata et al.

CA 129:270586, Clarke et al.

CA 119:108253, Ono.

Office Action dated Aug. 25, 2006 issued in U.S. Appl. No. 09/405,182, filed Sep. 24, 1999.

Office Action issued by Japanese Patent Office on Sep. 5, 2006 in connection with corresponding Japanese Application No. 2000-553043.

English translation of relevant parts of Examiner's comments in Japanese Office Action issued Sep. 5, 2006 in connection with corresponding Japanese Application No. 2000-553043.

Ylitalo, R., et al., "Effects of clodronate (dichloromethylene bisphosphonate) on the development of experimental atherosclerosis in rabbits", J. Lab. Clin. Med, 123, pp. 769-776, 1994.

Tremblay, A., et al., EM-800, A Novel Antiestrogen Acts as a Pure Antagonist of Transcriptinal Functions of Estrogen Receptors ▌ and ▌ , Endocrinology, 139(1), pp. 111-118, Jan. 1998.

U.S. Appl. No. 09/405,182, filed Sep. 24, 1999 in the name of Fernand Labrie and entitled "*Medical Uses of A Selective Estrogen Receptor Modulator in Combination With Sex Steroid Precursors*".

U.S. Appl. No. 11/062,233, filed Feb. 18, 2005 in the name of Fernand Labrie and entitled "*Medical Uses of A Selective Estrogen Receptor Modulator in Combination With Sex Steroid Precursors*".

U.S. Appl. No. 11/542,788, filed Oct. 3, 2006 in the name of Fernand Labrie and entitled "*Medical Uses of A Selective Estrogen Receptor Modulator in Combination With Sex Steroid Precursors*".

U.S. Appl. No. 11/542,733, filed Oct. 3, 2006 in the name of Fernand Labrie and entitled "*Medical Uses of A Selective Estrogen Receptor Modulator in Combination With Sex Steroid Precursors*".

U.S. Appl. No. 11/542,789, filed Oct. 3, 2006 in the name of Fernand Labrie and entitled "*Medical Uses of A Selective Estrogen Receptor Modulator in Combination With Sex Steroid Precursors*".

CA 130:108222, Nawata et al., 1996.

CA 129:270586, Clarke et al., 1998.

CA 119:108253, Ono, 1993.

Carter et al., Chemotherapy of Cancer, Second Edition, 1981, A Wiley Medical Publication John Wiley & Sons, pp. 361-367.

Schwartz et al., Dehydroepiandrosterone and Structural Analogs, 1988, Advances in Cancer Research, 51, pp. 391-424, ISSN: 0062-230X, abstract.

* cited by examiner

MEDICAL USES OF A SELECTIVE ESTROGEN RECEPTOR MODULATOR IN COMBINATION WITH SEX STEROID PRECURSORS

CROSS REFERENCE TO RELATED APPLICATIONS

This is a divisional of U.S. patent application Ser. No. 09/330,799, filed Jun. 11, 1999, now allowed, which is a Continuation-in-part of U.S. patent application Ser. No. 09/096,284, filed Jun. 11, 1998, now U.S. Pat. No. 6,465,445, which issued Oct. 12, 2002 in the name of Fernand Labrie and entitled "MEDICAL USES OF A SELECTIVE ESTROGEN RECEPTOR MODULATOR IN COMBINATION WITH SEX STEROID PRECURSORS".

FIELD OF THE INVENTION

The present invention relates to a method for treating or reducing the likelihood of acquiring osteoporosis, hypercholesterolemia, hyperlipidemia or atherosclerosis using a novel combination therapy on susceptible warm-blooded animals, including humans. In particular, the combination includes administering a selective estrogen receptor modulator (SERM) and raising the patient's level of precursor to sex steroids, said precursor being selected from the group consisting of dehydroepiandrosterone (DHEA), dehydroepiandrosterone sulfate (DHEA-S), and androst-5-ene-3β,17β-diol (5-diol). The invention also relates to kits and pharmaceutical composition for practicing the foregoing combination.

BACKGROUND OF THE RELATED ART

Man is thus unique, with some other primates, in having adrenals that secrete large amounts of the precursor steroids dehydroepiandrosterone sulfate (DHEA-S) and dehydroepiandrosterone (DHEA) which are converted into androstenedione (4-dione) and then into active androgens and/or estrogens in peripheral tissues (Labrie et al., In: Important Advances in Oncology. Edited by V. T. de Vita, S. Hellman, S. A. Rosenberg. J. B. Lippincott, Philadelphia, 193-217, 1985; Labrie, Mol. Cell. Endocrinol., 78: C113-C118, 1991; Labrie, et al., In Signal Transduction in Testicular Cells. Ernst Schering Research Foundation Workshop. Edited by V. Hansson, F. O. Levy, K. Taskén. Springer-Verlag, Berlin-New York (Suppl. 2), pp. 185-218, 1996; Labrie et al., Steroids, 62: 148-158, 1997). In a recent study (Labrie, et al., J. Clin. Endocrinol. Metab., 82: 2403-2409, 1997), we have described a dramatic decline in the circulating levels of dehydroepiandrosterone (DHEA), DHEA-sulfate (DHEA-S), androst-5-ene-3β,17β-diol (5-diol), 5-diol-S, 5-diol fatty acid esters, and androstenedione in both men and women between the ages of 20 and 80 years.

Despite the marked fall in endogenous androgens in women during aging, the use of androgens in post-menopausal women has been limited mainly because of the fear of an increased risk of cardiovascular disease as based upon older studies showing an unfavorable lipid profile with androgens. Recent studies, however, have shown no significant effect of combined estrogen and androgen therapy on the serum levels of cholesterol, triglycerides, HDL, LDL, and HDL/LDL ratio when compared to estrogen alone (Sherwin et al., Am. J. Obstet. Gynecol., 156: 414-419, 1987). In agreement with these observations, we have shown that DHEA, a compound having a predominantly androgenic influence, has apparently no deleterious effect on the serum lipid profile (Diamond, et al., J. Endocrinol., 150: S43-S50, 1996). Similarly, no change in the concentrations of cholesterol, its subfractions or triglycerides, over a treatment with estradiol alone has been observed after 6 months of therapy with estradiol+testosterone implants (Burger et al., Br Med. J. Clin. Res. Ed., 294: 936-937, 1987). It should be mentioned that a study in man has shown an inverse correlation between serum DHEA-S and low density lipoproteins (Parker et al., Science, 208: 512-514, 1980). More recently, a correlation has been found between low serum testosterone and DHEA and increased visceral fat, a parameter of higher cardiovascular risk (Tchernof et al., Metabolism, 44: 513-519, 1995).

Five-diol is a compound biosynthesized from DHEA through the action of reductive 17β-hydroxysteroid dehydrogenase (17β-HSD) and is a weak estrogen. It has an 85-fold lower affinity than 17β-estradiol ($E_2$) for the estrogen receptor in rat anterior pituitary gland cytosol (Simard and Labrie, J. Steroid Biochem., 26: 539-546, 1987), further confirming the data obtained on the same parameter in human myometrial and breast cancer tissue (Kreitmann and Bayard, J. Steroid Biochem., 11: 1589-1595, 1979; Adams et al., Cancer Res., 41: 4720-4926, 1981; Poulin and Labrie, Cancer Res., 46: 4933-4937, 1986). However, at concentrations well within the range of the plasma levels found in adult women, 5-diol enhances cell proliferation and progesterone receptor levels in human mammary tumor ZR-75-1 cells (Poulin and Labrie, Cancer Res., 46: 4933-4937, 1986) and increases the estrogen-dependent synthesis of the 52 kDa glycoprotein in MCF-7 cells (Adams et al., Cancer Res., 41: 4720-4926, 1981).

As mentioned above, it is known that the serum levels of DHEA, DHEA-S and 5-diol decrease with age and correspondingly, that there is a dramatic age-dependent reduction in the formation of androgens and estrogens in peripheral target tissues. Such changes in DHEA-S and DHEA secretion result in a marked decrease in the biochemical and cellular functions stimulated by sex steroids. As a result, DHEA and DHEA-S have recently been used in the treatment of a variety of conditions which are associated with decrease and/or imbalance in the levels of sex steroids.

Osteoporosis, a condition which affects both men and women, is associated with a decrease in androgens and estrogens. Estrogens have been shown to decrease the rate of bone degradation while androgens have been shown to build bone mass. However, estrogen replacement therapy commonly used against osteoporosis requires the addition of progestins to counteract the endometrial proliferation and the risk of endometrial cancer induced by estrogens. Moreover, since both estrogens and progestins are thought to increase the risk of breast cancer (Bardon et al., J. Clin. Endocrinol. Metab., 60: 692-697, 1985; Colditz et al., N. Engl. J. Med., 332: 1589-1593, 1995), the use of estrogen-progestin replacement therapy is accepted by a limited number of women and, usually, for too short periods of time.

Several studies suggest that osteoporosis is a clinical manifestation of androgen deficiency in men (Baran et al., Calcif. Tissue Res. 26: 103-106, 1978; Odell and Swerdloff, West J. Med. 124: 446-475, 1976; Smith and Walker, California Tissue Res. 22 (Suppl.): 225-228, 1976). Androgen therapy, as observed with nandrolone decanoate, has been found to increase vertebral bone mineral density in postmenopausal women (Need et al., Arch. Intern. Med., 149: 57-60, 1989). Therapy of postmenopausal women with nandrolone increased cortical bone mineral content (Need et al., Clin. Orthop. 225: 273-278, 1987). Androgenic side-effects, however, were recorded in 50% of patients. Such data are of interest since while almost all present therapies are limited to a reduction of bone loss, an increase in bone mass was found with the use of the anabolic steroid nandrolone. A similar stimulation of bone formation by androgens has been suggested in a hypogonadal male (Baran et al., Calcif. Tissue Res. 26: 103, 1978). A stimulation of bone formation in postmenopausal women treated with DHEA for 12 months is reported in Labrie et al. (J. Clin. Endocrinol. 82: 3498-3505, 1997).

DHEA (450 mg/kg, b.w., 3 times a week) markedly delayed the appearance of breast tumors in C3H mice which were genetically bred to develop breast cancer (Schwartz, Cancer Res. 39: 1129-1132, 1979). Moreover, the risk of developing bladder cancer was found to be increased in men having lower serum DHEA levels (Gordon et al., Cancer Res. 51: 1366-1369, 1991).

U.S. Patent Application U.S. Pat. No. 5,550,107 relates to a method of treatment of breast and endometrial cancer in susceptible warm-blooded animals which may include inhibition of ovarian hormonal secretion by surgical means (ovariectomy) or chemical means (use of an LHRH agonist, e.g. [D-Trp$^6$, des-Gly-NH$_2$$^{10}$]LHRH ethylamide, or antagonist) as part of a combination therapy.

Antiestrogens, androgens, progestins, inhibitors of sex steroid formation (especially of 17β-hydroxysteroid dehydrogenase- or aromatase-catalyzed production of sex steroids), inhibitors of prolactin secretion and of growth hormone secretion and ACTH secretion are discussed. A counterpart thereof has been published under international publication number WO 90/10462.

In addition, cardiovascular diseases have been associated with decreased serum levels of DHEA and DHEA-S and both DHEA and DHEA-S have been suggested to prevent or treat these conditions (Barrett-Connor et al., N. Engl. J. Med. 315: 1519-1524, 1986).

In aged Sprague-Dawley rats, Schwartz (in Kent, Geriatrics 37: 157-160, 1982) has observed that body weight was reduced from 600 to 550 g by DHEA without affecting food intake. Schwartz (Cancer 39: 1129-1132, 1979) observed that C3H mice given DHEA (450 mg/kg, 3 times a week) gained significantly less weight and grew older than the control animals, had less body fat and were more active. The reduction in body weight was achieved without loss of appetite or food restriction. Furthermore, DHEA could prevent weight gain in animals bred to become obese in adulthood (in Kent, Geriatrics 37: 157-160, 1982).

DHEA administration to lean Zucher rats decreased body weight gain despite increased food intake. Treated animals had smaller fat pads thus, overall, suggesting that DHEA increases food metabolism, resulting in lower weight gain and fat accumulation (Svec et al., Proc. 2$^{nd}$ Int. Conf. Cortisol and Anti-Cortisols, Las Vegas, Nev., USA, p. 56 abst., 1997).

Obesity was found to be improved in the A$^{vy}$ mutant mouse (Yen et al., Lipids 12: 409-413, 1977) and in the Zucker rat (Cleary and Zisk, Fed. Proc. 42: 536, 1983). DHEA-treated C3H mice had a younger appearance than controls (Schwartz, Cancer Res. 39: 1129-1132, 1979).

DHEA reduced the incidence of atherosclerosis in cholesterol-fed rabbits (Gordon et al., J. Clin. Invest. 82: 712-720, 1988; Arad et al., Arteriosclerosis 9: 159-166, 1989). Moreover, high serum concentrations of DHEA-S have been reported to protect against death from cardiovascular diseases in men (Barrett-Connor et al., N. Engl. J. Med. 315: 1519-1524, 1986). Circulating levels of DHEA and DHEA-S have thus been found to be inversely correlated with mortality from cardiovascular disease (Barrett-Connor et al., N. Engl. J. Med. 315: 1519-1524, 1986) and to decrease in parallel with the diminished immune competence (Thoman and Weigle, Adv. Immunol. 46: 221-222, 1989). A study in man has shown an inverse correlation between fetal serum DHEA-S and low density lipoprotein (LDL) levels (Parker et al., Science 208: 512, 1980).

Uses of DHEA as well as the benefits of androgen and estrogen therapy are discussed in International Patent Publication WO 94/16709.

Correlations observed in the prior art are not believed to suggest treatment or prophylactic methods that are effective, or as free of undesirable side-effects, as are combination therapies disclosed here.

SUMMARY OF THE INVENTION

It is accordingly an object of the present invention to provide effective methods of treatment for osteoporosis, hypercholesterolemia, hyperlipidemia, atherosclerosis, breast cancer, endometrial cancer, ovarian cancer and uterine cancer while minimizing undesirable side effects.

It is another object to provide methods of reducing the risk of acquiring the above diseases.

It is another object to provide kits and pharmaceutical compositions suitable for use in the above methods.

In one embodiment, the invention pertains to a method of treating or reducing the risk of acquiring osteoporosis comprising increasing levels of a sex steroid precursor selected from the group consisting of dehydroepiandrosterone (DHEA), dehydroepiandrosterone-sulfate (DHEA-S) and androst-5-ene-3β,17β-diol (5-diol), in a patient in need of said treatment or said reduction, and further comprising administering to said patient a therapeutically effective amount of a selective estrogen receptor modulator (SERM) as part of a combination therapy.

In another embodiment, the invention provides a method of treating or reducing the risk of acquiring hypercholesterolemia comprising increasing levels of a sex steroid precursor selected from the group consisting of dehydroepiandrosterone, dehydroepiandrosterone-sulfate and androst-5-ene-3β, 17β-diol, in a patient in need of said treatment or said reduction, and further comprising administering to said patient a therapeutically effective amount of a selective estrogen receptor modulator as part of a combination therapy.

In another embodiment, the invention provides a method of treating or reducing the risk of acquiring hyperlipidemia comprising increasing levels of a sex steroid precursor selected from the group consisting of dehydroepiandrosterone, dehydroepiandrosterone-sulfate and androst-5-ene-3β, 17β-diol, in a patient in need of said treatment or said reduction, and further comprising administering to said patient a therapeutically effective amount of a selective estrogen receptor modulator as part of a combination therapy.

In another embodiment, the invention provides a method of treating or reducing the risk of acquiring atherosclerosis comprising increasing levels of a sex steroid precursor selected from the group consisting of dehydroepiandrosterone, dehydroepiandrosterone-sulfate and androst-5-ene-3β,17β-diol, in a patient in need of said treatment or said reduction, and further comprising administering to said patient a therapeutically effective amount of a selective estrogen receptor modulator as part of a combination therapy.

In another embodiment, the invention provides a method of treating or reducing the risk of acquiring breast cancer comprising increasing levels of a sex steroid precursor selected from the group consisting of dehydroepiandrosterone, dehydroepiandrosterone-sulfate and androst-5-ene-3β,17β-diol, in a patient in need of said treatment or said reduction, and further comprising administering to said patient a therapeutically effective amount of a selective estrogen receptor modulator as part of a combination therapy.

In another embodiment, the invention provides a method of treating or reducing the risk of acquiring endometrial cancer comprising increasing levels of a sex steroid precursor selected from the group consisting of dehydroepiandrosterone, dehydroepiandrosterone-sulfate and androst-5-ene-3β,17β-diol, in a patient in need of said treatment or said reduction, and further comprising administering to said patient a therapeutically effective amount of a selective estrogen receptor modulator as part of a combination therapy.

In another embodiment, the invention provides a method of treating or reducing the risk of acquiring uterine cancer comprising increasing levels of a sex steroid precursor selected from the group consisting of dehydroepiandrosterone, dehydroepiandrosterone-sulfate and androst-5-ene-3β,17β-diol, in a patient in need of said treatment or said reduction, and further comprising administering to said patient a therapeutically effective amount of a selective estrogen receptor modulator as part of a combination therapy.

In another embodiment, the invention provides a method of treating or reducing the risk of acquiring ovarian cancer comprising increasing levels of a sex steroid precursor selected from the group consisting of dehydroepiandrosterone, dehydroepiandrosterone-sulfate and androst-5-ene-3β,17β-diol, in a patient in need of said treatment or said reduction, and further comprising administering to said patient a therapeutically effective amount of a selective estrogen receptor modulator as part of a combination therapy.

In another embodiment, the invention provides a kit comprising a first container containing a therapeutically effective amount of at least one sex steroid precursor selected from the group consisting of dehydroepiandrosterone, dehydroepiandrosterone-sulfate, androst-5-ene-3β,17β-diol and any prodrug that is converted in vivo into any of the foregoing precursors; and further comprising a second container containing a therapeutically effective amount of at least one selective estrogen receptor modulator.

In another embodiment, the invention provides a pharmaceutical composition comprising: a) a pharmaceutically acceptable excipient, diluent or carrier; b) a therapeutically effective amount of at least one sex steroid precursor selected from the group consisting of dehydroepiandrosterone, dehydroepiandrosterone-sulfate, androst-5-ene-3β,17β-diol and a prodrug that is converted in vivo into any of the foregoing sex steroid precursors; and c) a therapeutically effective amount of at least one selective estrogen receptor modulator.

In another embodiment, the invention provide a method of reducing the risk of acquiring breast cancer comprising administering, to a patient in need of such reduction a prophylactically effective amount of a selective estrogen receptor modulator.

In one embodiment of reducing the likelihood of acquiring breast cancer, it is desirable to combine administration of a SERM with administration of a sex steroid precursor. However, the invention also includes administering a SERM alone, which is shown, for example, in FIGS. 1 and 2, to provide significant prophylactic effect, even in the absence of administered precursors. Preferred SERMs for this purpose are the same as discussed for other uses herein. Preferred dosages and methods of administration are also the same.

As used herein, a selective estrogen receptor modulator (SERM) is a compound that either directly or through its active metabolite functions as an estrogen receptor antagonist ("antiestrogen") in breast tissue, yet provides estrogenic or estrogen-like effect on bone tissue and on serum cholesterol levels (i.e. by reducing serum cholesterol). Non-steroidal compounds that function as estrogen receptor antagonists in vitro or in human or rat breast tissue (especially if the compound acts as an antiestrogen on human breast cancer cells) is likely to function as a SERM. Conversely, steroidal antiestrogens tend not to function as SERMs because they tend not to display any beneficial effect on serum cholesterol. Non-steroidal antiestrogens we have tested and found to function as SERMs include EM-800, EM-01538, Raloxifene, Tamoxifen and Droloxifene. We have tested the steroidal antiestrogen ICI 182,780 and found not to function as SERMs. SERMs in accordance with the invention may be administered in the same dosage as known in the art when these compounds are used as antiestrogens.

We have also noted a correlation between the beneficial effect SERMs have on serum cholesterol and beneficial estrogenic or estrogen-like effects on bone and on serum lipids. SERMs that have been shown in our research to act beneficially on all of these parameters, include bone mass, cholesterol, and triglyceride levels. Without intending to be bound by theory, it is believed that SERMs, many of which preferably, have two aromatic rings linked by one to two carbon atoms, are expected to interact with the estrogen receptor by virtue of the foregoing portion of the molecule that is best recognized by the receptor. Preferred SERMs have side chains which may selectively cause antagonistic properties in breast tissue without having significant antagonistic properties in other tissues. Thus, the SERMs may desirably functions as antiestrogens in the breast while surprisingly and desirably functioning as estrogens (or providing estrogen-like activity) in bone and in the blood (where concentrations of lipid and cholesterol are favorably affected). The favorable effect on cholesterol and lipid translates to a favorable effect against atherosclerosis which is known to be adversely, affected by improper levels of cholesterol and lipid.

All of the diseases treated by the invention as discussed herein respond favorably to androgens. Rather than utilizing androgens per se, applicants utilize sex steroid precursors such as DHEA, DHEA-S, 5-diol, or prodrugs converted to any such sex steroid precursors. In vivo, DHEA-S is converted to DHEA which in turn converts to 5-diol. It is believed that any tissue responding favorably to one is likely to respond favorably to the others. Prodrug forms of active metabolites are well known in the art. See, e.g. H. Bundgaard "Design and Application of Prodrugs" (In: A Textbook of Drug Design and Development. Edited by H. Bundgaard and P. Krogsgaard-Larsen; Harwook Academic Publishers GmfH, Chur: Switzerland, 1991), the contents of which are incorporated herein by reference. In particular, see pages 154-155 describing various functional groups of active metabolites and appropriate corresponding prodrug groups that convert in vivo to each functional group. Where a patients' levels of sex steroid precursors are raised in accordance with the invention, that may typically be accomplished by administering such a precursor or by administering a prodrug of such a precursor. By utilizing precursors instead of androgens, undesirable androgenic activity in tissues other than the target is reduced. Tissues convert precursors such as DHEA to androgens only through a natural and more regulated process. A large percentage of androgens are locally produced in peripheral tissues and to different extents in different tissues.

The cancers treated in accordance with the invention respond adversely to estrogenic activity. On the other hand, osteoporosis, hypercholesterolemia, hyperlipidemia, and atherosclerosis respond favorably to estrogenic or estrogen-like activity. By using SERMs in accordance with the invention, desirable effects are provided in target tissues without undesirable effects in certain other tissues. For example, a SERM can have favorable estrogenic effect in the bone (or on lipid or cholesterol) while avoiding unfavorable estrogenic effect in the breast.

Thus both precursor and SERM provide favorable effect in target tissues while minimizing unfavorable effects in certain other tissues. Moreover, there are substantial synergies in using the two together in accordance with the invention. For example, estrogens and androgens provide beneficial effect against osteoporosis by different mechanisms (estrogen reducing bone resorption, androgen contributing to bone formation). The combination of the present invention provides bone with beneficial estrogen or estrogen-like effect through the activity of SERM, and also provides beneficial androgen through local conversion of precursor to androgen in the bone. Precursor is also believed to provide estrogen. The same is true in connection with controlling lipid or cholesterol (useful for treating or preventing atherosclerosis). A similar synergy is provided against breast, endometrial, ovarian or uterine cancer where the SERM provides desirable antiestrogenic effect and the precursor provides desirable androgenic effect (with any incidental conversion of precursor to estrogen being mitigated by the antiestrogen). Undesirable effects are also mitigated in a synergistic way by the combination used in the invention. For all diseases discussed herein, any other effect on breast tissues that might otherwise result from estrogens produced by the precursor (when the precursor is used for promoting androgenic effects in accordance with the invention) is mitigated by the antiestrogenic effect of the SERM in breast tissue.

In some embodiments, progestins are added to provide further androgenic effect. Progestins may be used at low dosages known in the art without adversely affecting receptors other than the androgen receptors (e.g. glucocorticoid receptors). They also are relatively free of unwanted androgenic side effects (such as facial hair with female patients).

Preferred SERMs discussed herein relate: (1) to all diseases stated to be susceptible to the invention; (2) to both therapeutic and prophylactic applications; and (3) to preferred pharmaceutical compositions and kits.

In one embodiment, the precursor is DHEA.

In another embodiment, the precursor is DHEA-S.

In another embodiment, the precursor is 5-diol.

A patient in need of treatment or of reducing the risk of onset of a given disease is one who has either been diagnosed with such disease or one who is susceptible to acquiring such disease.

Except where otherwise stated, the preferred dosage of the active compounds (concentrations and modes of administration) of the invention is identical for both therapeutic and prophylactic purposes. The dosage for each active component discussed herein is the same regardless of the disease being treated (or of the disease whose likelihood of onset is being reduced).

Except when otherwise noted or where apparent from context, dosages herein refer to weight of active compounds unaffected by pharmaceutical excipients, diluents, carriers or other ingredients, although such additional ingredients are desirably included, as shown in the examples herein. Any dosage form (capsule, tablet, injection or the like) commonly used in the pharmaceutical industry is appropriate for use herein, and the terms "excipient", "diluent", or "carrier" include such nonactive ingredients as are typically included, together with active ingredients in such dosage forms in the industry. For example, typical capsules, pills, enteric coatings, solid or liquid diluents or excipients, flavorants, preservatives, or the like may be included.

All of the active ingredients used in any of the therapies discussed herein may be formulated in pharmaceutical compositions which also include one or more of the other active ingredients. Alternatively, they may each be administered separately but sufficiently simultaneous in time so that a patient eventually has elevated blood levels or otherwise enjoys the benefits of each of the active ingredients (or strategies) simultaneously. In some preferred embodiments of the invention, for example, one or more active ingredients are to be formulated in a single pharmaceutical composition. In other embodiments of the invention, a kit is provided which includes at least tow separate containers wherein the contents of at least one container differs, in whole or in part, from the contents of at least one other container with respect to active ingredients contained therein.

Combination therapies discussed herein also include use of one active ingredient (of the combination) in the manufacture of a medicament for the treatment (or risk reduction) of the disease in question where the treatment or prevention further includes another active ingredient of the combination in accordance with the invention. For example in one embodiment, the invention provides the use of a SERM in the preparation of a medicament for use, in combination with a sex steroid precursor selected from the group consisting of DHEA, DHEA-S, 5-diol, and pro-drugs converted to any of the foregoing sex steroid precursors, in vivo, in the treatment of any of the diseases for which the present combination therapy is believed effective (i.e., breast cancer, endometrial cancer, uterine cancer, ovarian cancer, osteoporosis, hypercholesterolemia, hyperlipidemia, and atherosclerosis). In another embodiment, the invention provides the use of a sex steroid precursor selected from the group consisting of DHEA, DHEA-S, 5-diol, and pro-drugs converted to any of the foregoing sex steroid precursors, in vivo, in the preparation of a medicament for use, in combination with a SERM, for treatment of any of those same diseases.

In one embodiment of the invention, DHEA is not utilized as the precursor. In another embodiment, EM-800 is not used as the SERM. In another embodiment, the combination of DHEA with EM-800 is not used.

In one preferred embodiment, DHEA is used in combination with EM-1538.

DETAIL DESCRIPTION OF THE INVENTION

Figure 1:
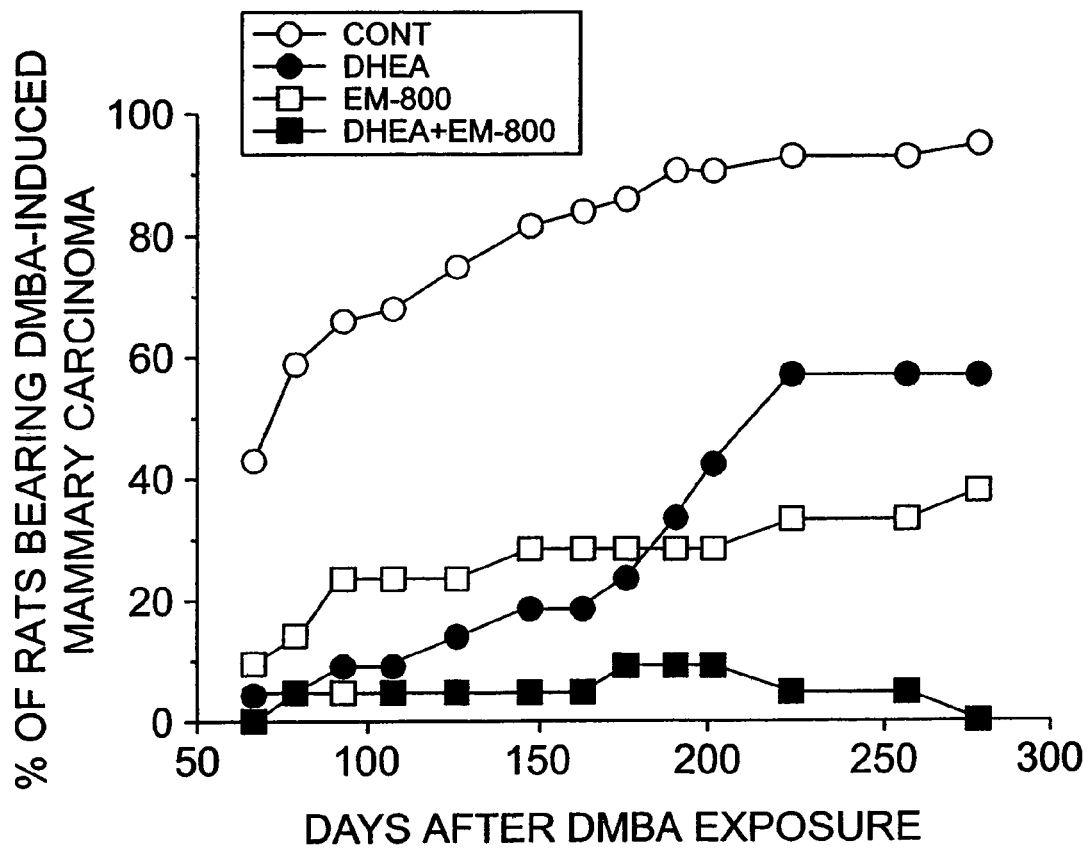
FIG. 1 shows the effect of treatment with DHEA (10 mg, percutaneously, once daily) or EM-800 (75 μg, orally, once daily) alone or in combination for 9 months on the incidence of DMBA-induced mammary carcinoma in the rat throughout the 279-day observation period. Data are expressed as percentage of the total number of animals each group.

Estrogens are well-known to stimulate the proliferation of breast epithelial cells and cell proliferation itself is thought to increase the risk of cancer by accumulating random genetic errors that may result in neoplasia (Preston Martin et al., Cancer. Res. 50: 7415-21, 1990). Based on this concept, antiestrogens have been introduced to prevent breast cancer with the objective of reducing the rate of cell division stimulated by estrogens.

The loss of ovarian cyclicity found in female Sprague-Dawley rats after 10 months of age is accompanied by increased serum estrogen and prolactin levels and decreased serum androgen and progesterone concentrations (Lu et al., 61st Annual Meeting of the Endocrine Society 106 (abst. #134), 1979; Tang et al., Biol. Reprod. 31: 399-413, 1984; Russo et al., Monographs on Pathology of Laboratory Animals: Integument and Mammary Glands 252-266, 1989; Sortino and Wise, Endocrinology 124: 90-96, 1989; Cardy, Vet. Pathol. 28: 139-145, 1991). These hormonal changes that spontaneously occur in aging female rats are associated with multifocal proliferation and increased secretory activity of the acinar/alveolar tissue as well as mammary gland duct dilatation and formation of cysts (Boorman et al., 433, 1990; Cardy, Vet. Pathol. 28: 139-145, 1991). It should be mentioned that hyperplastic and neoplastic changes of the rat mammary gland are often accompanied by increased levels of estrogens and prolactin (Meites, J. Neural. Transm. 48: 25-42, 1980). Treatment with EM-800, a SERM of the present invention, induces atrophy of the mammary gland which is characterized by a decrease in the size and number of the lobular structures, and no evidence of secretory activity, indicating the potent antiestrogenic activity of EM-800 in the mammary gland (Luo et al. Endocrinology 138: 4435-4444, 1997).

Treatment with DHEA, a sex steroid precursor of the present invention, leads to an elevation in serum DHEA and 5-diol while serum 4-dione, testosterone, dihydrotestosterone, and estradiol levels are only moderately increased or more often remain unchanged, thus confirming the intracellular biotransformation of this precursor steroid in peripheral tissues (Labrie et al., Mol. Cell. Endocrinol. 78: C113-C118, 1991). However, the stimulatory effect of orally administered DHEA on serum androgens, such as testosterone and dihydrotestosterone, is of greater amplitude than the effect on serum estrogens, thus suggesting that DHEA is predominantly transformed into androgens in these animals. This observation is in agreement with the data obtained in women where the formation of androgens from DHEA was a more important pathway than the conversion of DHEA into estrogens (Morales et al., J. Clin. Endocrinol. Metab. 78: 1360-1367, 1994; Labrie et al., Ann. N.Y. Acad. Sci. 774: 16-28, 1995; Labrie et al., Steroids 62: 148-158, 1997).

With the knowledge of the above-described potent antiestrogenic activity resulting in mammary gland atrophy and the predominant androgenic effect of DHEA on the mammary gland, the histomorphological changes seen in animals treated with the combination of a SERM and a sex steroid precursor are best explained by an unopposed androgenic action of DHEA in the rat mammary gland.

Most importantly, it has been observed that androgens exert a direct antiproliferative activity on the growth of ZR-75-1 human breast cancer cells in vitro and that such an inhibitory effect of androgens is additive to that of an antiestrogen (Poulin and Labrie, Cancer Res. 46: 4933-4937, 1986; Poulin et al., Breast Cancer Res. Treat. 12: 213-225, 1988). Similar inhibitory effects have been observed in vivo on ZR-75-1 xenographts in nude mice (Dauvois et al., Cancer Res. 51: 3131-3135, 1991). Androgens have also been shown to inhibit the growth of DMBA-induced mammary carcinoma in the rat, this inhibition being reversed by the simultaneous administration of the pure antiandrogen Flutamide (Dauvois et al., Breast Cancer Res. Treat. 14: 299-306, 1989). Taken together, the present data indicate the involvement of the androgen receptor in the inhibitory action of DHEA on breast cancer.

Since antiestrogens and sex steroid precursors exert inhibitory effects on breast cancer via different mechanisms, the present invention shows that the combination of a SERM (EM-800) and a sex steroid precursor (DHEA) exerts more potent inhibitory effects than each compound used alone on the development of DMBA-induced rat mammary carcinoma as well illustrated in FIGS. 1 and 2. In fact, no DMBA-induced tumor was found at the end of the experiment in animals that had received both DHEA and EM-800.

The present invention describes that the combination of a sex steroid precursor (DHEA) and a SERM (EM-800) maintained the stimulatory effect of DHEA on bone formation and potentiated the inhibitory effect of the SERM (EM-800) alone on bone turnover and resorption as demonstrated by the further decreases in urinary hydroxyproline and calcium excretion when both compounds were combined.

We have shown that DHEA has beneficial effects on bone in both the female rat (Luo et al., Endocrinology 138: 4435-4444, 1997), and postmenopausal women (Labrie et al., J. Clin.

Endocrinol. Metab. 82:. 3498-3505, 1997). Thus, in intact female rats, treatment with DHEA increases bone mineral density (BMD) of total skeleton, lumbar spine and femur (Luo et al., Endocrinology 138: 4435-4444, 1997).

On the other hand, treatment with EM-800 had no significant effect on BMD in intact animals although potent stimulatory effects are observed in the ovariectomized rat (Martel et al., unpublished data). Since EM-800 exerts such stimulatory effects on BMD of total skeleton, lumbar spine and femur in ovariectomized rats, the lack of significant stimulatory effect of EM-800 in intact animals could be due to the fact that the sex steroids present in intact female rats exert maximal effect on BMD (Luo et al., Endocrinology 138: 4435-4444, 1997). Similarly, the lack of significant effect of EM-800 in ovariectomized rats already receiving DHEA is likely due to the maximal stimulatory effects exerted by the androgens (and possibly estrogens) synthesized in bone cells from exogenous DHEA.

Figure 3A:
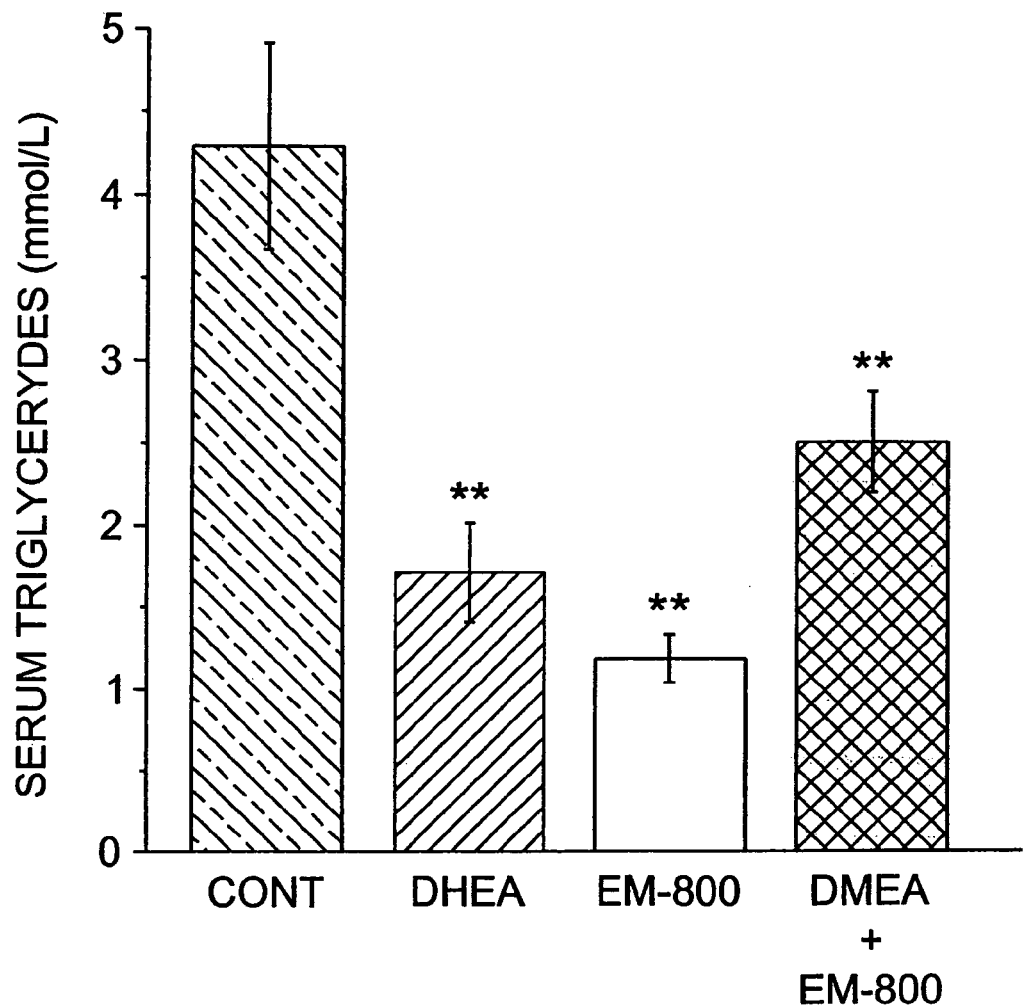
FIG. 3 shows the effect of treatment with DHEA (10 mg, percutaneously, once daily) or EM-800 (75 μg, orally, once daily) alone or in combination for 9 months on serum triglyceride (A) and cholesterol (B) levels in the rat. Data are expressed as the means±SEM. **: $P<0.01$ experimental versus respective control.
Figure 3B:
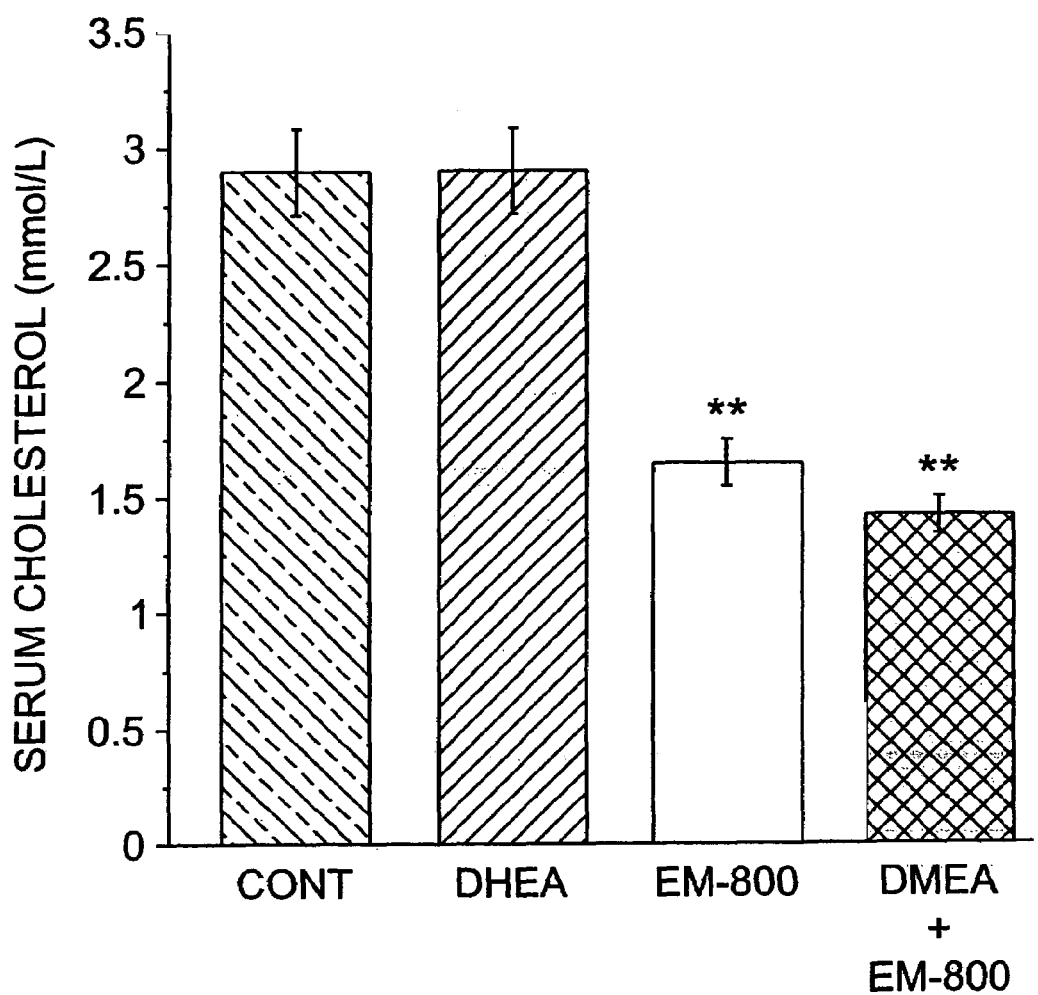

Estrogens are known to lower serum cholesterol but to increase or to have no effect on serum triglycerides levels (Love et al., Ann. Intern. Med. 115: 860-864, 1991; Walsh et al., New Engl. J. Med. 325: 1196-1204, 1.991; Barrett-Connor, Am. J. Med. 95 (Suppl. SA): 40S-43S, 1993; Russell et al., Atherosclerosis 100: 113-122, 1993; Black et al., J. Clin. Invest. 93: 63-69, 1994; Dipippo et al., Endocrinology 136: 1020-1033, 1995; Ke et al., Endocrinology 136: 2435-2441, 1995). FIG. 3 shows that EM-800 possesses both hypocholesterolemic and hypotriglyceridemic effects in the rat, thus showing its unique action on the serum lipid profile which is apparently different from other SERMs, such as tamoxifen (Bruning et al., Br. J. Cancer 58: 497-499, 1988; Love et al., J. Natl. Cancer Inst. 82: 1327-1332, 1990; Dipippo et al., Endocrinology 136: 1020-1033, 1995; Ke et al., Endocrinology 136: 2435-2441, 1995), droloxifene (Ke et al., Endocrinology 136: 2435-2441, 1995), and raloxifene (Black et al., J. Clin. Invest. 93: 63-69, 1994). The combination of DHEA and EM-800 preserved the hypocholesterolemic and hypotriglyceridemic effects of EM-800, thus suggesting that such a combination could exert beneficial effects on serum lipids.

It should be mentioned that the serum lipid profile is markedly different between rats and humans. However, since an estrogen receptor-mediated mechanism is involved in the hypocholesterolemic effect of estrogens as well as antiestrogens (Lundeen et al., Endocrinology 138: 1552-1558, 1997), the rat remains a useful model to study the cholesterol-lowering effect of estrogens and "antiestrogens" in humans.

In brief, the above-described data clearly demonstrate the effects of the combination of a SERM (EM-800) and a sex steroid precursor (DHEA) on the development of mammary carcinoma induced by DMBA as well as the protective effects of such a combination on bone mass and serum lipids.

Such data suggest the additional beneficial effects of such a combination for treatment and prevention of osteoporosis while improving the lipid profile.

We have also studied the potential interaction of the inhibitory effect of the novel antiestrogen (EM-800) with that of sex steroid precursor (DHEA) on the growth of human ZR-75-1 breast cancer xenografts in nude mice by combined administration of the two drugs. FIGS. 4 and 5 show that DHEA, by itself, at the doses used, causes a 50 to 80% inhibition of tumor growth while the near complete inhibition of tumor growth achieved with a low dose of the antiestrogen was not affected by DHEA.

The limitations of bone mineral density (BMD) measurements are well known. As an example, BMD measurements showed no change in rats treated with the steroidal antiestrogen ICI 182780 (Wakeling, Breast Cancer Res. Treat. 25: 1-9, 1993) while inhibitory changes were seen by histomorphometry (Gallagher et al., Endocrinology 133: 2787-2791, 1993). Similar differences were reported with Tamoxifen (Jordan et al., Breast Cancer Res. Treat. 10: 31-35, 1987; Sibonga et al., Breast Cancer Res. Treatm. 41: 71-79, 1996).

It should be indicated that reduced bone mineral density is not the only abnormality associated with reduced bone strength. (Guidelines for preclinical and clinical evaluation of agents used in the prevention or treatment of postmenopausal osteoporosis, Division of Metabolism and Endocrine Drug Products, FDA, May 1994). It is thus important to analyze the changes in biochemical parameters of bone metabolism induced by various compounds and treatments in order to gain a better knowledge of their action.

It is particularly important to indicate that the combination of DHEA and EM-800 exerted unexpected beneficial effects on important biochemical parameters of bone metabolism. In fact, DHEA alone did not affect the urinary hydroxyproline/ creatinine ratio, a marker of bone resorption. Moreover, no effect of DHEA could be detected on daily urinary calcium or phosphorus excretion (Luo et al., Endocrinology 138: 4435-4444, 1997). EM-800, on the other hand, decreased the urinary hydroxyproline/creatinine ratio by 48% while, similarly to DHEA, no effect of EM-800 was seen on urinary calcium or phosphorus excretion. EM-800, moreover, had no effect on serum alkaline phosphatase activity, a marker of bone formation while DHEA increased the value of the parameter by about 75% (Luo et al., Endocrinology 138: 4435-4444, 1997).

Figure 6:
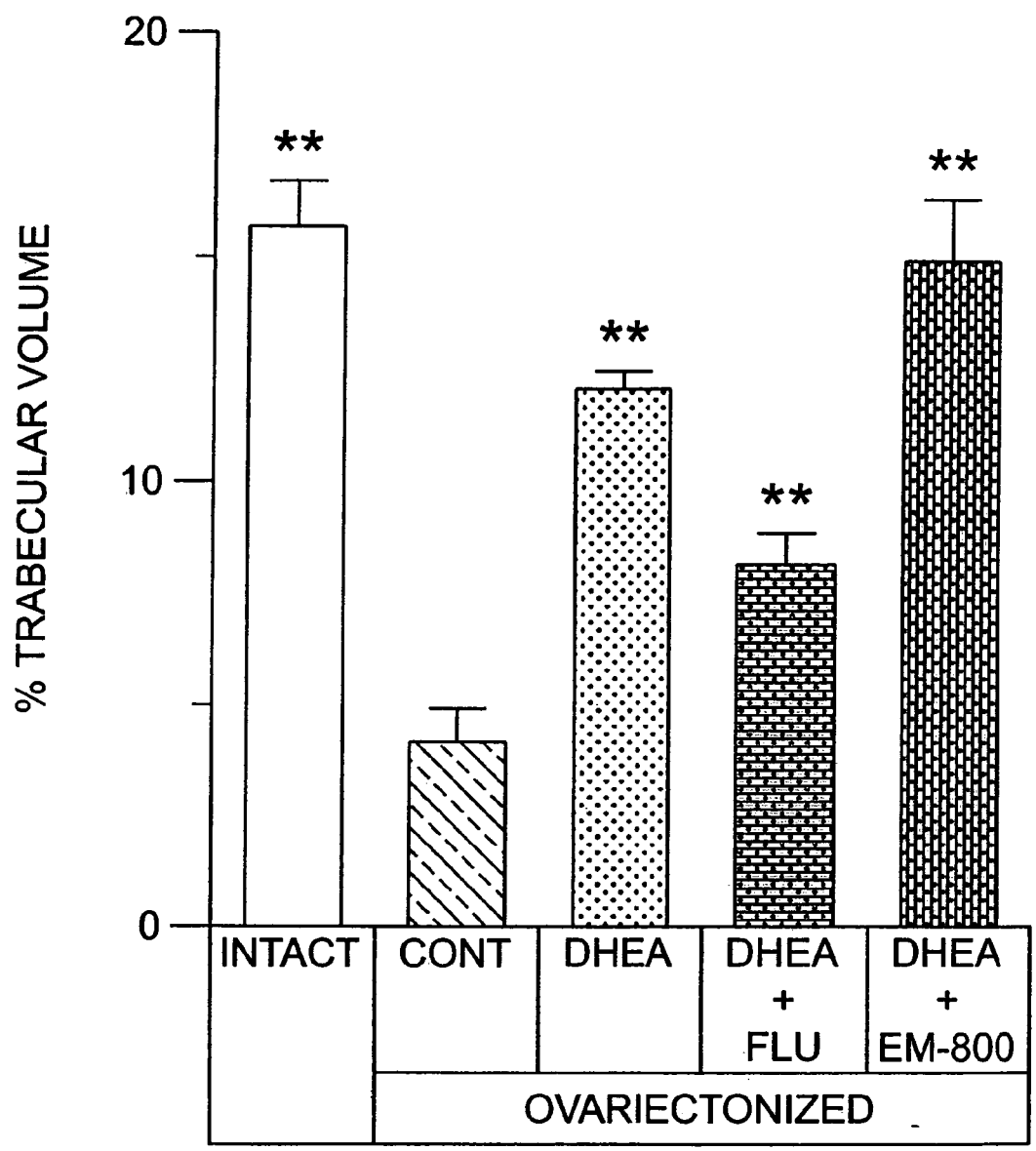
FIG. 6 shows the effect of 12-month treatment with dehydroepiandrosterone (DHEA) alone or in combination with Flutamide or EM-800 on trabecular bone volume in ovariectomized rats. Intact animals are added as additional controls. Data are presented as mean±SEM ** p<0.01 versus OVX Control.

One of the unexpected effects of the combination of DHEA and EM-800 relates to the urinary hydroxyproline/creatinine ratio, a marker of bone resorption, which was reduced by 69% when both DHEA and EM-800 were combined, this value being statistically different ($p<0.01$) from the 48% inhibition achieved by EM-800 alone while DHEA alone did not show any effect. Thus, the addition of DHEA to EM-800 increases by 50% of the inhibitory effect of EM-800 on bone reabsorption. Most importantly, another unexpected effect of the addition of DHEA to EM-800 was the approximately 84% decrease in urinary calcium (from $23.17\pm1.55$ to $3.71\pm0.75$ µmol/24 h/100 g ($p<0.01$) and the 55% decrease in urinary phosphorus (from $132.72\pm6.08$ to $59.06\pm4.76$ µmol/24 h/100 g ($p<0.01$) respectively, (Luo et al., Endocrinology 138: 4435-4444, 1997).

the addition of EM-800 to DHEA further increased trabecular bone volume to $14.7\pm1.4\%$, a value similar to that found in intact controls (FIG. 6)

Figure 7:
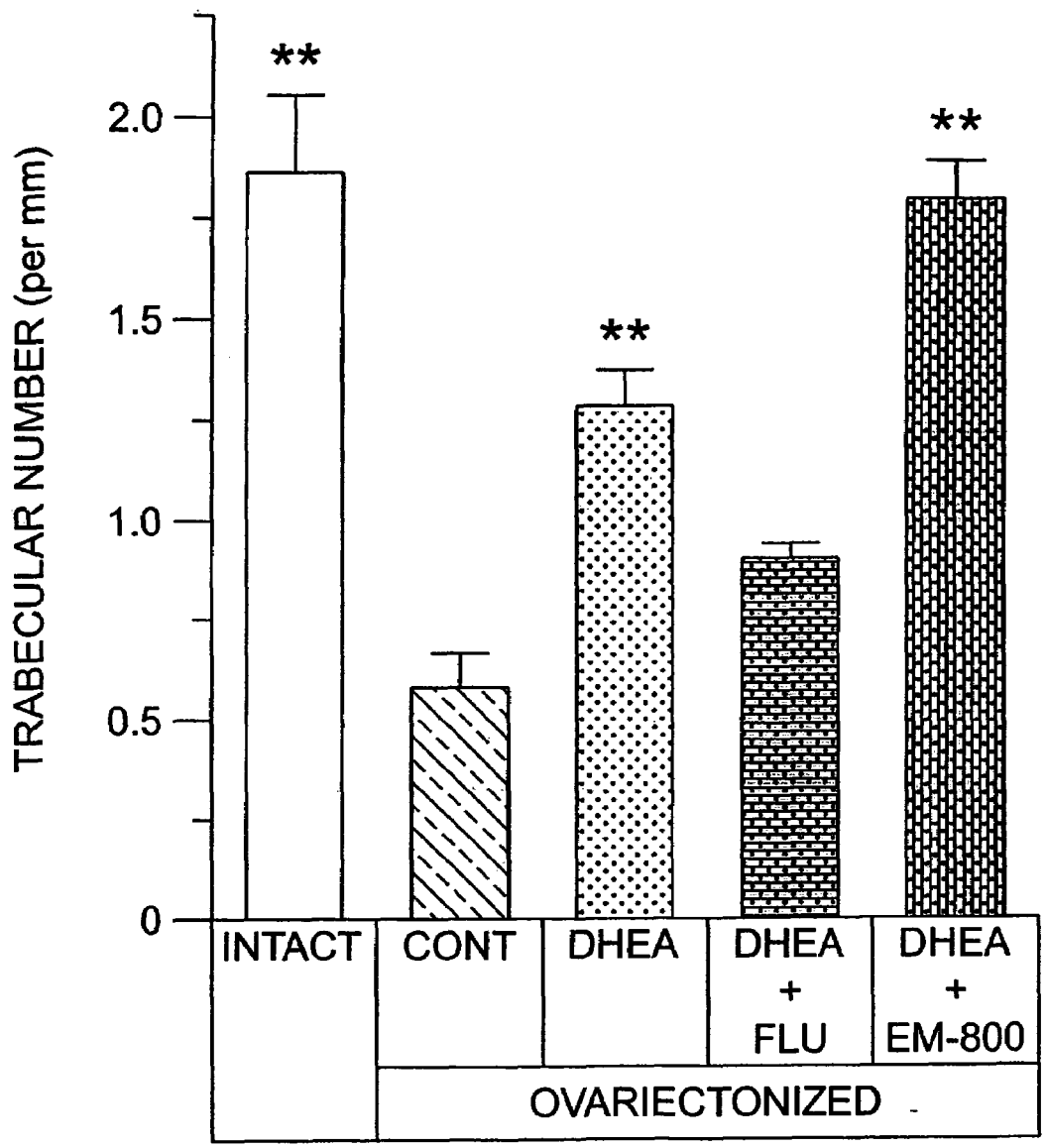
FIG. 7 shows the effect of 12-month treatment with dehydroepiandrosterone (DHEA) alone or in combination with Flutamide or EM-800 on trabecular number in ovariectomized rats. Intact animals are added as additional controls. Data are presented as mean±SEM ** p<0.01 versus OVX Control.

From a value of $0.57\pm0.08$ per mm in ovariectomized rats, treatment with DHEA resulted in a 137% increase in trabecular bone number compared to ovariectomized controls. The stimulatory effect of DHEA thus reached $1.27\pm0.1$ per mm while simultaneous treatment with EM-800 and DHEA resulted in an additional 28% increase in trabecular bone number ($p<0.01$) compared to that achieved by DHEA alone (FIG. 7). Similarly, the addition of EM-800 to DHEA treatment, resulted in an additional 15% ($p<0.05$) decrease in trabecular bone separation, compared to that achieved with DHEA alone, thus leading to values not different from those seen in intact controls.

Figure 8:
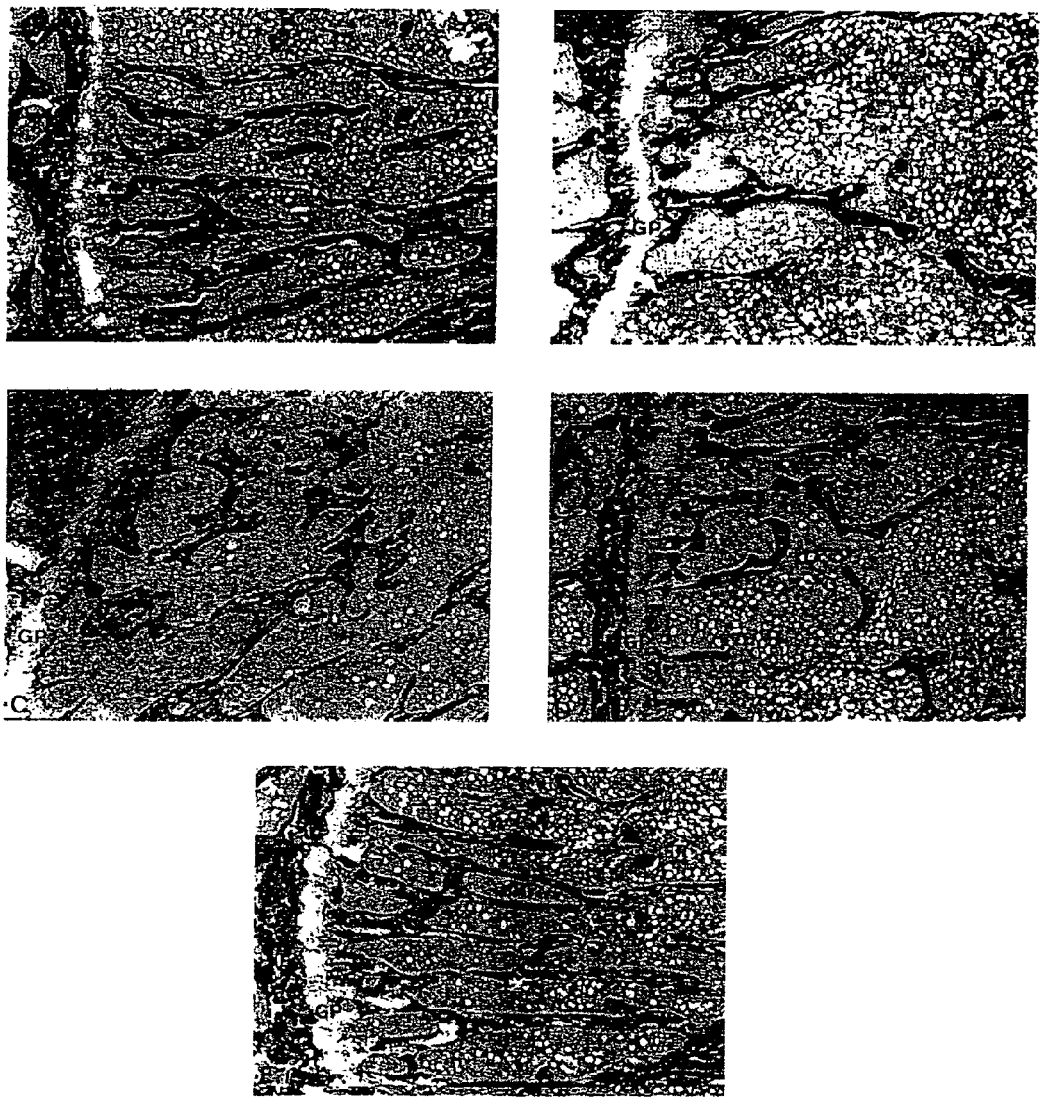
FIG. 8 shows proximal tibia metaphyses from intact control (A), ovariectomized control (B), and ovariectomized rats treated with DHEA alone (C) or in combination with Flutamide (D) or EM-800 (E). Note the reduced amount of trabecular bone (T) in ovariectomized control animals (B), and the significant increase in trabecular bone volume (T) induced after DHEA administration (C). The addition of Flutamide to DHEA partially blocked the effect of DHEA on the trabecular bone volume (D), whereas the combination of DHEA and EM-800 provided complete protection against the ovariectomy-associated bone loss. Modified trichrome Masson-Goldner, magn.x80. T: Trabeculae, GP: Growth Plate.
Figure 9:
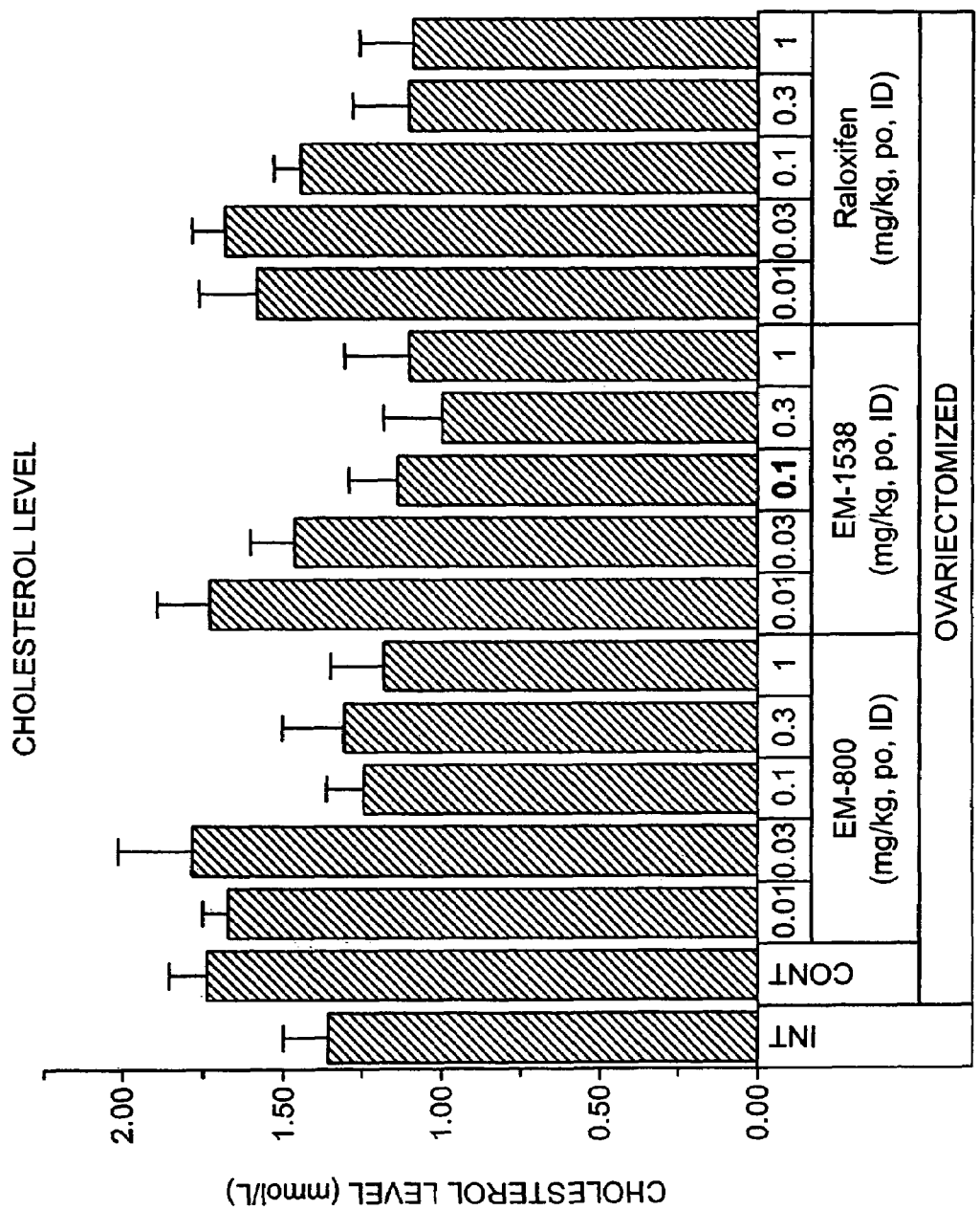
FIG. 9 shows the effect of increasing doses (0.01, 0.03, 0.1, 0.3, and 1 mg/kg) of EM-800, EM-1538 and Raloxifene (EM-11095) administered per os daily for 4 days on cholesterol level of ovariectomized rat.
Figure 10:
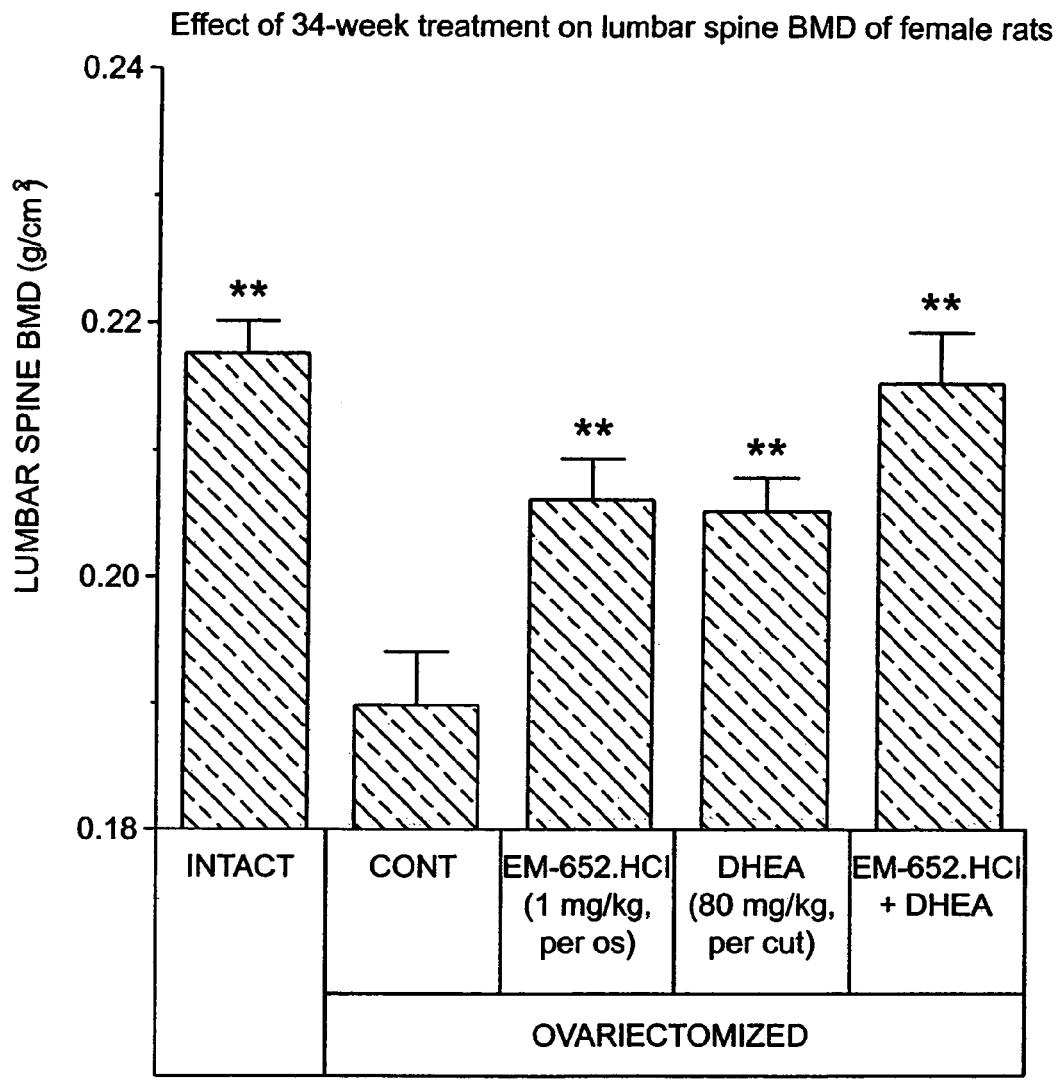
FIG. 10 shows the effect of 34-week treatment with dehydroepiandrosterone (DHEA) alone or in combination with EM-1538 (EM-652.HCl) on lumbar spine BMD in ovariectomized rats. Intact animals are added as additional controls. Data are presented as mean±SEM ** p<0.01 versus OVX Control.
Figure 11:
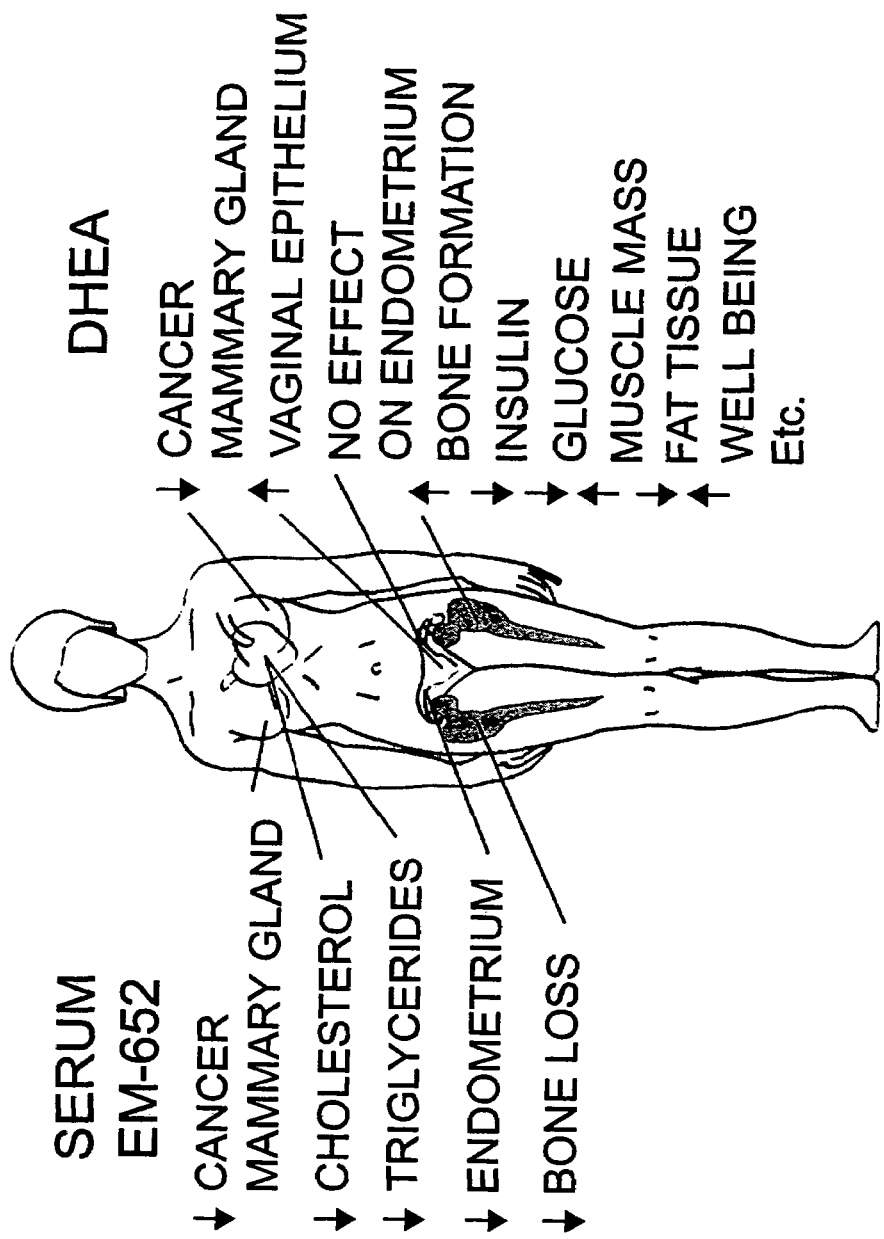
FIG. 11 shows the combined effects of the SERM (EM-652) and DHEA on parameters of menopause. No negative effect is expected.

As complement to the numerical data presented in FIGS. 6 and 7, FIG. 8 illustrates the increase in trabecular bone volume in the proximal tibia metaphysis induced by DHEA in ovariectomized treated animals (C) compared to ovariectomized controls (B), as well as the partial inhibition of the stimulatory effect of DHEA after the addition of Flutamide to DHEA treatment (D). On the other hand, administration of DHEA in combination with EM-800 resulted in a complete

TABLE 1

| GROUP | URINE | | | SERUM |
|---|---|---|---|---|
| | CALCIUM (µmol/24 h/100 g) | PHOSPHORUS (µmol/24 h/100 g) | HP/Cr (µmol/mmol) | tALP (IU/L) |
| CONTROL | $23.17 \pm 1.55$ | $132.72 \pm 6.08$ | $13.04 \pm 2.19$ | $114.25 \pm 14.04$ |
| DHEA (10 mg) | $25.87 \pm 3.54$ | $151.41 \pm 14.57$ | $14.02 \pm 1.59$ | $198.38 \pm 30.76$* |
| EM-800 (75 µg) | $17.44 \pm 4.5$ | $102.03 \pm 25.13$ | $6.81 \pm 0.84$** | $114.11 \pm 11.26$ |
| DHEA + EM-800 | $3.71 \pm 0.75$** | $59.06 \pm 4.76$** | $4.06 \pm 0.28$** | $204.38 \pm 14.20$** |

It is also of interest to note that the potent inhibitory effect of EM-800 on serum cholesterol is not prevented by simultaneous treatment with DHEA (Luo et al., Endocrinology 138: 4435-4444, 1997). While Raloxifene and similar compounds prevent bone loss and decrease serum cholesterol (like estrogens), it should be mentioned that when Raloxifene was compared to Premarin on BMD, the effect of Raloxifene on BMD was less potent than that of Premarin (Minutes of the Endocrinology and Metabolism Drugs Advisory Committee, FDA Thursday, Meeting #68, Nov. 20, 1997). Because of its well known adverse effects on breast and uterine cancer, the addition of an estrogen to Raloxifene, EM-800 or other similar compounds is not an acceptable solution.

The present results obtained in the rat clearly demonstrate that DHEA can provide the beneficial effects which are lacking with the use of a selective estrogen receptor modulator (SERM) alone such as EM-800, Raloxifene, etc. While a SERM has effects limited to inhibition of bone resorption, the addition of DHEA, 5-diol, DHEA-S is believed to stimulate bone formation (an effect not found with a SERM or an estrogen) and further reduce bone resorption above the effect achieved with EM-800.

Importantly, the combination of EM-800 and DHEA in ovariectomized rats treated for 12 months has beneficial effects on bone morphometry. Trabecular bone volume is particularly important for bone strength and to prevent bone fractures. Thus, in the above-mentioned study, trabecular bone volume of the tibia increased from $4.1\pm0.7\%$ in ovariectomized rats to $11.9\pm0.6\%$ ($p<0.01$) with DHEA alone while prevention of the ovariectomy-induced osteopenia (E), the trabecular bone volume being comparable to that seen in intact controls (A).

The bone loss observed at menopause in women is believed to be related to an increase in the rate of bone resorption which is not fully compensated by the secondary increase in bone formation. In fact, the parameters of both bone formation and bone resorption are increased in osteoporosis and both bone resorption and formation are inhibited by estrogen replacement therapy. The inhibitory effect of estrogen replacement on bone formation is thus believed to result from a coupled mechanism between bone resorption and bone formation, such that the primary estrogen-induced reduction in bone resorption entrains a reduction in bone formation (Parfitt, Calcified Tissue International 36 Suppl. 1: S37-S45, 1984).

Cancellous bone strength and subsequent resistance to fracture do not only depend upon the total amount of cancellous bone but also on the trabecular microstructure, as determined by the number, size, and distribution of the trabeculae. The loss of ovarian function in postmenopausal women is accompanied by a significant decrease in total trabecular bone volume (Melsen et al., Acta Pathologica & Microbiologica Scandinavia 86: 70-81, 1978; Vakamatsou et al., Calcified Tissue International 37: 594-597, 1985), mainly related to a decrease in the number and, to a lesser degree, in the width of trabeculae (Weinstein and Hutson, Bone 8: 137-142, 1987).

In the present study, the androgenic stimulatory effect of DHEA was observed on almost all the bone histomorphometric parameters studied. DHEA thus resulted in a significant increase in trabecular bone volume as well as trabecular number, while it decreased the intertrabecular area.

In order to facilitate the combination therapy aspect of the invention, for any indication discussed herein, the invention contemplates pharmaceutical compositions which include both the SERM or the bisphosphonate compound and the sex steroid precursor (DHEA, DHEAS, 5-diol) in a single composition for simultaneous administration. The composition may be suitable for administration in any traditional manner including but not limited to oral administration, subcutaneous injection, intramuscular injection or percutaneous administration. In other embodiments, a kit is provided wherein the kit includes one or more SERM or bisphosphonate and sex steroid precursors in separate or in one container. The kit may include appropriate materials for oral administration, e.g. tablets, capsules, syrups and the like and for transdermal administration, e.g., ointments, lotions, gels, creams, sustained release patches and the like.

Applicants believe that administration of SERMs and sex steroid precursors has utility in the treatment and/or prevention of the development of osteoporosis, breast cancer, hypercholesterolemia, hyperlipidemia or atherosclerosis. The active ingredients of the invention (whether SERM or precursor or bisphosphonate or otherwise) may be formulated and administered in a variety of manner.

Active ingredient for transdermal or transmucosal is preferably present at from 0.5% to 20% by weight relative to the total weight of the pharmaceutical composition more preferably between 2 and 10%. DHEA or 5-diol should be at a concentration of at least 7% for percutaneous administration.

Alternatively, the active ingredient may be placed into a transdermal patch having structures known in the art, for example, structures such as those set forth in E.P. Patent No.0279982.

When formulated as an ointment, lotion, gel or cream or the like, the active compound is admixed with a suitable carrier which is compatible with human skin or mucosa and which enhances transdermal penetration of the compound through the skin or mucosa. Suitable carriers are known in the art and include but are not limited to Klucel HF and Glaxal base. Some are commercially available, e.g., Glaxal base available from Glaxal Canada Limited Company. Other suitable vehicles can be found in Koller and Buri, S.T.P. Pharma 3(2), 115-124, 1987. The carrier is preferably one in which the active ingredient(s) is (are) soluble at ambient temperature at the concentration of active ingredient that is used. The carrier should have sufficient viscosity to maintain the inhibitor on a localized area of skin or mucosa to which the composition has been applied, without running or evaporating for a time period sufficient to permit substantial penetration of the precursor through the localized area of skin or mucosa and into the bloodstream where it will cause a desirable clinical effect. The carrier is typically a mixture of several components, e.g. pharmaceutically acceptable solvents and a thickening agent. A mixture of organic and inorganic solvents can aid hydrophylic and lipophylic solubility, e.g. water and an alcohol such as ethanol.

Preferred sex steroid precursors are dehydroepiandrosterone (DHEA) (available from Diosynth Inc., Chicago, Ill., USA), its prodrugs (available from Steraloids, Wilton, N.H., USA), 5-androsten-3β,17β-diol and its prodrugs EM-1304 and EM-01474-D (available from Steraloids, Wilton, N.H. USA).

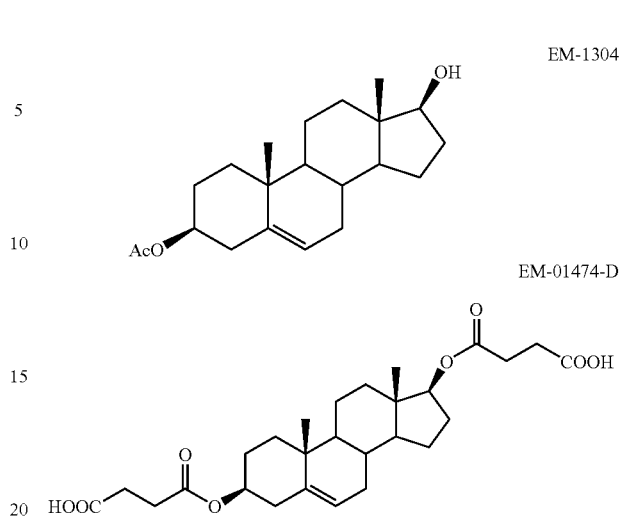

It is preferred that the sex steroid precursor is formulated as an alcoholic gel containing 2.0 to 10% of caprylic-capric triglyceride (Neobee M-5); 10 to 20% of hexylene glycol; 2.0 to 10% of diethyleneglycol monomethyl ether (Transutol); 2.0 to 10% of Cyclomethicone (Dow Corning 345); 1.0 to 2% of benzyl alcohol and 1.0 to 5.0% of hydroxypropylcellulose (Klucel HF).

The carrier may also include various additives commonly used in ointments and lotions and well known in the cosmetic and medical arts. For example, fragrances, antioxidants, perfumes, gelling agents, thickening agents such as carboxymethylcellulose, surfactants, stabilizers, emollients, coloring agents and other similar agents may be present. When used to treat systemic diseases, the site of application on the skin should be changed in order to avoid excess local concentration of active ingredient and possible overstimulation of the skin and sebaceous glands by androgenic metabolites of sex steroid precursor.

In a pharmaceutical composition for oral administration, DHEA or other precursor is preferably present in a concentration between 5 and 98% by weight relative to total weight of the composition more preferably between 50 and 98 percent, especially between 80 and 98 percent. A single precursor such as DHEA may be the only active ingredient, or alternatively, a plurality of precursors and/or their analogues may be used (e.g., a combination of DHEA, DHEA-S, 5-diol, or a combination of two or more compounds converted in vivo to DHEA, DHEA-S or 5-diol or a combination of DHEA or 5-diol and one or more analogues thereof which are converted to DHEA or 5-diol in vivo, etc. The blood level of DHEA is the final criteria of adequate dosage which takes into account individual variation in absorption and metabolism.

Preferably, the attending clinician will, especially at the beginning of treatment, monitor an individual patient's overall response and serum levels of DHEA (in comparison to the preferred serum concentrations discussed above), and monitor the patient's overall response to treatment, adjusting dosages as necessary where a given patients' metabolism or reaction to treatment is a typical.

Treatment in accordance with the invention is suitable for indefinite continuation. It is expected that DHEA and/or 5-diol treatment will simply maintain DHEA levels within a range similar to that which occurs naturally in women before menopause (serum concentration between 4 and 10 micrograms per liter), or naturally in young adult men (serum concentration between 4 and 10 micrograms per liter).

The SERM compound or bisphosphonate and/or the sex steroid precursor can also be administered, by the oral route, and may be formulated with conventional pharmaceutical excipients, e.g. spray dried lactose, microcrystalline cellulose, and magnesium stearate into tablets or capsules for oral administration.

The active substance can be worked into tablets or dragee cores by being mixed with solid, pulverulent carrier substances, such as sodium citrate, calcium carbonate or dicalcium phosphate, and binders such as polyvinyl pyrrolidone, gelatin or cellulose derivatives, possibly by adding also lubricants such as magnesium stearate, sodium lauryl sulfate, "Carbowax" or polyethylene glycol. Of course, taste-improving substances can be added in the case of oral administration forms.

As further forms, one can use plug capsules, e.g. of hard gelatin, as well as closed solf-gelatin capsules comprising a softner or plasticizer, e.g. glycerine. The plug capsules contain the active substance preferably in the form of granulate, e.g. in mixture with fillers, such as lactose, saccharose, mannitol, starches, such as potato starch or amylopectin, cellulose derivatives or highly dispersed silicic acids. In solf-gelatin capsules, the active substance is preferably dissolved or suspended in suitable liquids, such as vegetable oils or liquid polyethylene glycols.

The lotion, ointment, gel or cream should be thoroughly rubbed into the skin so that no excess is plainly visible, and the skin should not be washed in that region until most of the transdermal penetration has occurred preferably at least 4 hours and, more preferably, at least 6 hours.

A transdermal patch may be used to deliver precursor in accordance with known techniques. It is typically applied for a much longer period, e.g., 1 to 4 days, but typically contacts active ingredient to a smaller surface area, allowing a slow and constant delivery of active ingredient.

A number of transdermal drug delivery systems that have been developed, and are in use, are suitable for delivering the active ingredient of the present invention. The rate of release is typically controlled by a matrix diffusion, or by passage of the active ingredient through a controlling membrane.

Mechanical aspects of transdermal devices are well known in the rat, and are explained, for example, in U.S. Pat. Nos. 5,162,037, 5,154,922, 5,135,480, 4,666,441, 4,624,665, 3,742,951, 3,797,444, 4,568,343, 5,064,654, 5,071,644, 5,071,657, the disclosures of which are incorporated herein by reference. Additional background is provided by European Patent 0279982 and British Patent Application 2185187.

The device may be any of the general types known in the art including adhesive matrix and reservoir-type transdermal delivery devices. The device may include drug-containing matrixes incorporating fibers which absorb the active ingredient and/or carrier. In a reservoir-type device, the reservoir may be defined by a polymer membrane impermeable to the carrier and to the active ingredient.

In a transdermal device, the device itself maintains active ingredient in contact with the desired localized skin surface. In such a device, the viscosity of the carrier for active ingredient is of less concern than with a cream or gel. A solvent system for a transdermal device may include, for example, oleic acid, linear alcohol lactate and dipropylene glycol, or other solvent systems known in the art. The active ingredient may be dissolved or suspended in the carrier.

For attachment to the skin, a transdermal patch may be mounted on a surgical adhesive tape having a hole punched in the middle. The adhesive is preferably covered by a release liner to protect it prior to use. Typical material suitable for release includes polyethylene and polyethylene-coated paper, and preferably silicone-coated for ease of removal. For applying the device, the release liner is simply peeled away and the adhesive attached to the patient's skin. In U.S. Pat. No. 5,135,480, the disclosure of which is incorporated by reference, Bannon et al. describe an alternative device having a non-adhesive means for securing the device to the skin.

The percutaneous or transmucosal delivery system of the invention may also be used as a novel and improved delivery system for the prevention and/or treatment of osteoporosis or other diseases which respond favorably to treatment with androgens and/or estrogens.

A selective estrogen receptor modulator of the invention has a molecular formula with the following features: a) two aromatic rings spaced by 1 to 2 intervening carbon atoms, both aromatic rings being either unsubstituted or substituted by a hydroxyl group or a group converted in vivo to hydroxyl; and b) a side chain possessing an aromatic ring and a tertiary amine function or salt thereof.

One preferred SERM of the invention is EM-800 reported in PCT/CA96/00097 (WO 96/26201)

The molecular structure of EM-800 is:

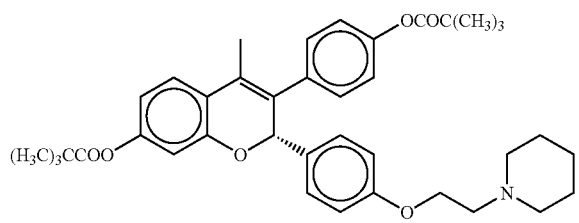

Another preferred SERM of the invention is EM-01538:

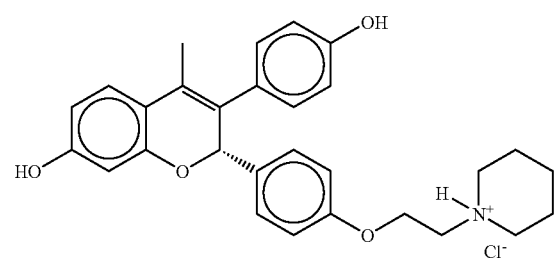

EM-1538, (also called EM-652.HCL) is the hydrochloride salt of the potent antiestrogen EM-652 compared to EM-800, EM-1538 is a simpler and easier salt to synthesize. It was also easy to isolate, purify, crystallizable, and displayed good solid state stability. In administering either EM-800 or EM-1538, it is believed to result in the same active compound in vivo.

Other preferred SERMs of the invention include Tamoxifen ((Z)-2-[4-(1,2-diphenyl-1-butenyl)]-N,N-dimethylethanamine) (available from Zeneca, UK), Toremifene (available from Orion-Farmos Pharmaceuticla, Finland, or Schering-Plough), Droloxifene and CP-336,156 (cis-1R-[4'-pyrrolidinoethoxyphenyl]-2S-phenyl-6-hydroxy-1,2,3,4,-tetrahydronapthalene D-(−)-tartrate salt) (Pfizer Inc., USA), Raloxifene (Eli Lilly and Co., USA), LY 335563 and LY 353381 (Eli Lilly and Co., USA), Iodoxifene (SmithKline Beecham, USA), Levormeloxifene (3,4-trans-2,2-dimethyl-3-phenyl-4-[4-(2-(2-(pyrrolidin-1-yl)ethoxy)phenyl]-7- methoxychroman) (Novo Nordisk, A/S, Denmark) which is disclosed in Shalmi et al. WO 97/25034, WO 97/25035, WO 97/25037, WO 97/25038; and Korsgaard et al. WO 97/25036), GW5638 (described by Willson at al., Endocrinology, 138(9), 3901-3911, 1997) and indole derivatives (disclosed by Miller et al. EP 0802183A1) and TSE 424 developed by Wyeth Ayers (USA) and disclosed in JP10036347 (American home products corporation) and nonsteroidal estrogen derivatives described in WO 97/32837.

Any SERM used as required for efficacy, as recommended by the manufacturer, can be used. Appropriate dosages are known in the art. Any other non steroidal antiestrogen commercially available can be used according to the invention. Any compound having activity similar to SERMs (example: Raloxifene can be used).

SERMs administered in accordance with the invention are preferably administered in a dosage range between 0.01 to 10 mg/kg of body weight per day (preferably 0.05 to 1.0 mg/kg), with 5 mg per day, especially 10 mg per day, in two equally divided doses being preferred for a person of average body weight when orally administered, or in a dosage range between 0.003 to 3.0 mg/kg of body weight per day (preferably 0.015 to 0.3 mg/ml), with 1.5 mg per day, especially 3.0 mg per day, in two equally divided doses being preferred for a person of average body weight when parentally administered (i.e. intramuscular, subcutaneous or percutaneous administration). Preferably the SERMs are administered together with a pharmaceutically acceptable diluent or carrier as described below.

Preferred bisphosphonates of the invention include Alendronate [(4-amino-1-hydroxybutylidene)bis phosphonic acid, disodium salt, hydrate] available from Merck Shape and Dohme under the Tradename of Fosamax, Etidronate [(1-hydroxyethylidene)bis phosphonic acid, 2,2'-iminobis ethanol] available from Procter and Gamble under the Trade names of Didrocal and Didronel, Clodronate [(dichloromethylene)bis phosphonic acid, disodium salt] available from Rhône-Poulenc Rorer under the Trade name of Bonefos or available from Boehringer Mannheim under the Trade name of Ostac and, Pamidronate (3-amino-1-hydroxypropylidene) bis phosphonic acid, disodium salt) available from Geigy under the Tradename of Aredia. Risedronate (1-hydroxy-2-(3-pyridinyl)ethylidene bisphosphonic acid monosodium salt) is under clinical development. Any other bisphosphonates commercially available can be used according to the invention, all at the manufacturers' recommended dosage. Likewise sex steroid precursors may be utilized at dosages recommended in the prior art, preferably at dosages that restore circulating levels to those of healthy males 20-30 years of age or those of premenopausal adult females.

With respect to all of the dosages recommended herein, the attending clinician should monitor individual patient response and adjust dosage accordingly.

EXAMPLES

Example 1

Materials and Methods

Animals

Female Sprague-Dawley rats [Crl:CD(SD)Br] were obtained at 44-46 days of age from Charles River Canada Inc. (St. Constant, Quebec) and housed 2 per cage in a light (12 h light/day; lights on at 07:15 h)- and temperature (22±2° C.)- controlled environment. Animals received Purina rodent chow and tap water ad libitum. The animal studies were conducted in a Canadian Council on Animal Care (CCAC)-approved facility in agreement with the CCAC Guide for Care and Use of Experimental Animals.

Induction of Mammary Tumors by DMBA

Mammary carcinomas were induced by a single intragastric administration of 20 mg of DMBA (Sigma Chemical Co., St. Louis, Mo.) in 1 ml of corn oil at 50-52 days of age. Two months later, tumor measurement was performed biweekly. The two largest perpendicular diameters of each tumor were recorded with calipers to estimate tumor size as described (Asselin et al., Endocrinology 101: 666-671, 1977). Tumor site, size and number were recorded.

Treatment

The animals were randomly divided into groups each containing 20 rats with the exception of 40 animals in the control group. The animals were treated for 282 days with the following: (1) control vehicles, for both DHEA and EM-8.00; (2) EM-800 ((+)-7-pivaloyloxy-3-(4'-pivaloyloxyphenyl)-4-methyl-2-(4"-(2'"-piperidinoethoxy)phenyl)-2H-benzopyran) (75 µg, orally, once daily) in 0.5 ml of a 4% ethanol, 4% polyethylene glycol-600, 1% gelatin, 0.9% NaCl suspension; (3) DHEA (10 mg, percutaneously, once daily) in 0.5 ml of 50% ethanol, 50% propylene glycol; and (4) both EM-800 and DHEA. Treatment was initiated 3 days before the oral administration of DMBA. EM-800 was synthesized in the Medicinal Chemistry Division of our laboratory while DHEA was purchased from Steraloids Inc., Wilton, N.H.

Many of the control animals and some of EM-800- or DHEA-treated animals were sacrificed by cervical dislocation under isoflurane-induced anesthesia 6 months after DMBA administration because of the too large size of tumors. The values of tumor size and number of these rats at sacrifice, together with those measured at later time intervals from the surviving animals, were used for the later analysis of the incidence of tumors, average tumor number per tumor-bearing rat and average tumor size per tumor-bearing animal. The remaining animals (9 rats from control and 13-19 rats from each other group) continued to receive treatment for another 3-month period in order to observe long-term preventive potency of DHEA and EM-800 alone or in combination. Rats were sacrificed 279 days after DMBA administration. The uteri, vaginas, and ovaries were immediately removed, freed from connective and adipose tissue, and weighed.

Sample Collection and Processing

Twenty-four-hour urinary samples were collected at the end of the experiment from the first 9 rats of each group following transfer in metabolic cages (Allentown Caging Equipment Co., Allentown, N.J.). Two urinary samples were collected and analyzed on different days for each animal in order to minimize the influence of daily variation. Therefore, each value shown represents the mean of the two measurements performed on two different days. 0.5 ml of toluene was added into the urine collecting tubes to prevent urine evaporation and bacterial growth and the urinary volume was recorded. Trunk blood was collected at sacrifice and was allowed to clot at 4° C. overnight before centrifugation at 3000 rpm for 30 min.

Analysis of Urine and Serum Biochemical Parameters

Fresh samples were used for the assay of urinary creatinine, calcium, and phosphorus as well as serum total alkaline phosphatase (tALP) activity, cholesterol and triglycerides. These biochemical parameters were measured automatically with a Monarch 2000 Chemistry System (Instrumentation Laboratory Co. Lexington, Mass.) under Good Laboratory Practice conditions. Urinary hydroxyproline was measured as described (Podenphant et al., Clinica Chimica Acta 142: 145-148, 1984).

Bone Mass Measurements

Rats were anesthetized with an i.p. injection of ketamine hydrochloride and diazepam at doses of 50 and 4 mg/kg B.W., respectively. The whole skeleton and the right femur were scanned using dual energy X-ray absorptiometry (DEXA; QDR 2000-7.10° C, Hologic, Waltham, Mass.) equipped with a Regional High Resolution software. The scan field sizes were 28.110×17.805 cm and 5.0×1.902 cm, the resolutions were 0.1511×0.0761 cm and 0.0254×0.0127 cm, while the scan speeds were 0.3608 and 0.0956 mm/sec for total skeleton and femur, respectively. Both bone mineral content (BMC) and bone mineral density (BMD) of total skeleton, lumbar spine, and femur were measured on the scan images of total skeleton and femur.

Statistical Analyses

Statistical significance was measured according to the multiple range test of Duncan-Kramer (Biometrics 12: 307-310, 1956). Analysis of the incidence of development of mammary tumors was performed using the Fisher's exact test (Conover, Practical nonparametric statistics, 2nd Edition 153-170, 1980). The data are presented as means±S.E.M.

Results

Effect on the Development of DMBA-induced Mammary Carcinoma

As illustrated in FIG. 1, 95% of control animals developed palpable mammary tumors by 279 days after DMBA administration. Treatment with DHEA or EM-800 partially prevented the development of DMBA-induced mammary carcinoma and the incidence was thus reduced to 57% ($p<0.01$) and 38% ($p<0.01$), respectively. Interestingly, combination of the two compounds led to a significantly higher inhibitory effect than those achieved by each compound alone ($p<0.01$ versus DHEA or EM-800 alone). In fact, the only two tumors which developed in the group of animals treated with both compounds disappeared before the end of experiment.

Figure 2A:
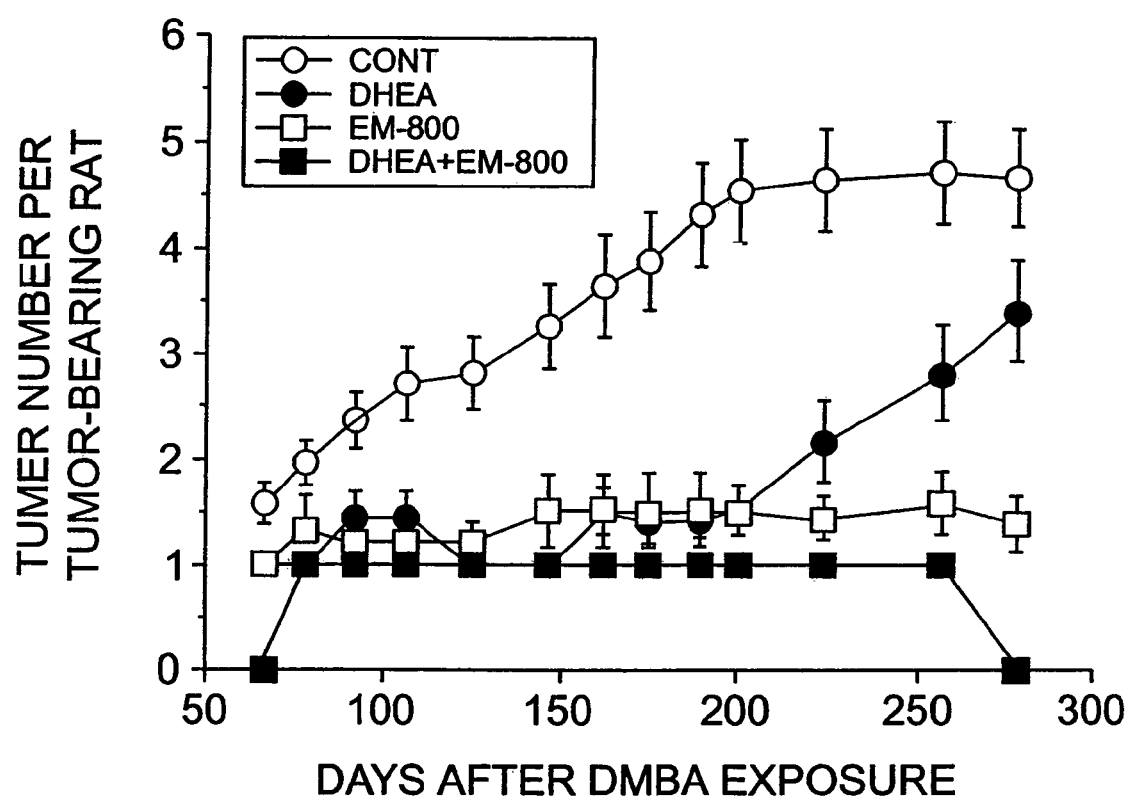
FIG. 2 shows the effect of treatment with DHEA (10 mg, percutaneously, once daily) or EM-800 (75 μg, orally, once daily) alone or in combination for 9 months on average tumor number per tumor-bearing animal (A) and on average tumor size per tumor-bearing rat (B) throughout the 279-day observation period. Data are expressed as the means±SEM.
Figure 2B:
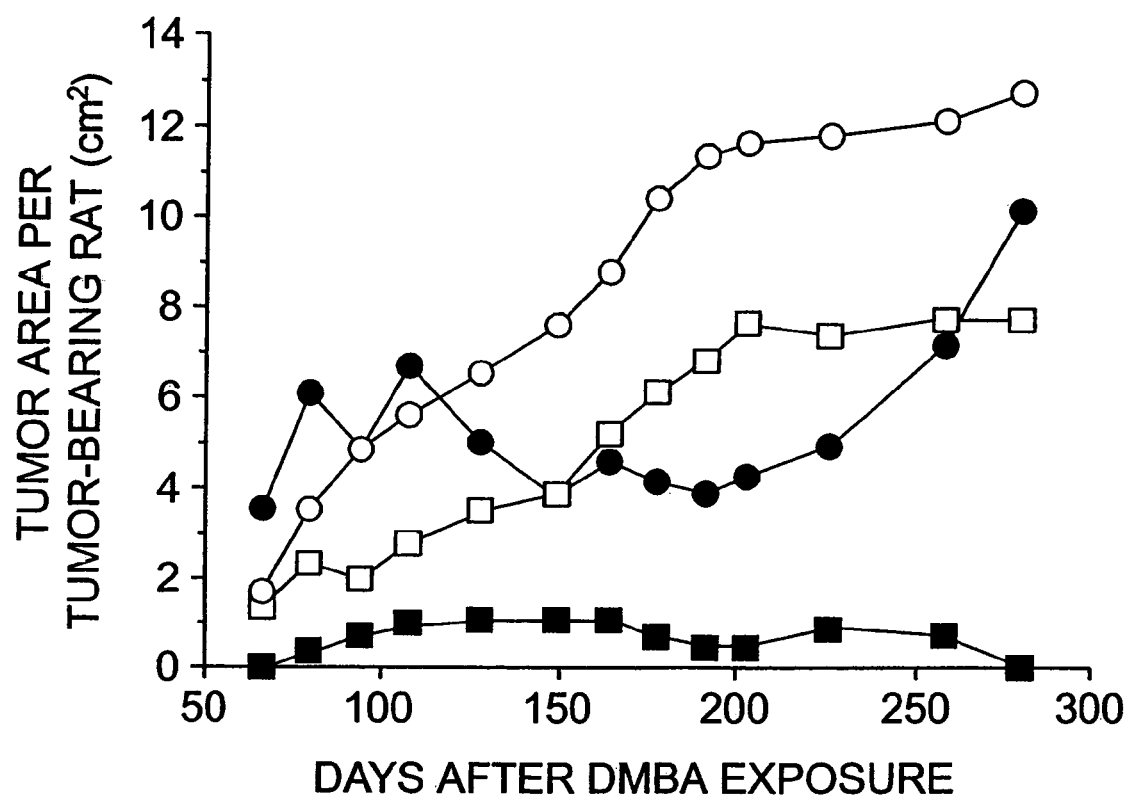

Treatment with DHEA or EM-800 decreased average tumor number per tumor-bearing animal from 4.7±0.5 tumors in control animals to 3.4±0.7 (N.S.) and 1.4±0.3 ($p<0.01$) tumors/animal, respectively, while no tumor was found at the end of the experiment in the animals who received both drugs ($p<0.01$ versus the three other groups) (FIG. 2A). One of the two tumors which later disappeared was present from day 79 to day 201 following DMBA administration while the other tumor was palpable from day 176 to day 257. It can be seen in FIG. 2B that DHEA or EM-800 alone decreased average tumor area per tumor-bearing animal from 12.8±1.3 cm$^2$ at the end of the experiment to 10.2±2.1 cm$^2$ (N.S.) and 7.7±1.8 cm$^2$ (N.S.), respectively, while the combination treatment resulted in a zero value ($p<0.01$ versus the three other groups). The two tumors which developed in the group of animals treated with both DHEA and EM-800 did not grow larger than 1 cm$^2$. It should be mentioned that the real values of average tumor area as well as the average tumor number per tumor-bearing animal in the control group should be higher than the values presented in FIG. 2, since many rats had to be sacrificed before the end of the experiment because of the excessive size of tumors. The values measured at time of sacrifice were thus included as such in the calculations made at later time intervals in order to minimize a bias in the control group which, in any case, remained significantly above the other groups.

Effect on Bone

Long-term percutaneous administration of DHEA to female rats induced 6.9% ($p<0.01$), 10.6% ($p<0.05$), and 8.2% ($p<0.01$) increases in bone mineral density (BMD) of total skeleton, lumbar spine, and femur, respectively (Table 2). On the other hand, no significant change was found in the animals treated with EM-800. Furthermore, when both compounds were administered simultaneously, the values obtained were comparable to those achieved with DHEA alone.

Treatment with DHEA increased serum total alkaline phosphatase (tALP) activity by 74% ($p<0.05$), but had no effect on daily urinary calcium and phosphorus excretion and on the urinary ratio of hydroxyproline to creatinine (Table 3). On the other hand, treatment with EM-800 decreased the urinary hydroxyproline to creatinine ratio by 48% ($p<0.01$), but had no statistically significant influence on daily urinary calcium or phosphorus excretion and serum tALP activity. The combination of DHEA and EM-800 led to an increase in serum tALP activity ($p<0.01$) similar to that achieved with DHEA alone and reduced the urinary hydroxyproline to creatinine ratio by 69%, a value significantly ($p<0.01$) lower than that achieved with EM-800 alone. In addition, the combination of the two drugs significantly reduced daily urinary calcium and phosphorus excretion by 84% ($p<0.01$) and 56% ($p<0.01$), respectively, while no significant change was observed with each drug alone (Table 3).

Effect on Serum Lipid Levels

Long-term treatment with EM-800 lowered serum triglyceride and cholesterol levels by 72% ($p<0.01$) and by 45% ($p<0.01$), respectively, whereas long-term administration of DHEA decreased serum triglycerides levels by 60% ($p<0.01$), serum cholesterol levels being unaffected. Moreover, 42% ($p<0.01$) and 52% ($p<0.01$) decreases in serum triglyceride and cholesterol concentrations were measured in the animals treated with both EM-800 and DHEA (FIG. 3).

TABLE 2

Effect of treatment with DHEA (10 mg, percutaneously, once daily) or EM-800 (75 μg, orally, once daily) alone or in combination for 9 months on bone mineral density (BMD) of femur, lumbar spine, and total skeleton in the female rat. Measurements were performed in 9 rats per group.
*$p < 0.05$;
**$p < 0.01$, experimental versus control.

| GROUP | BMD (g/cm2) | | |
|---|---|---|---|
| | TOTAL SKELETON | LUMBAR SPINE | FEMUR |
| CONTROL | 0.1371 ± 0.0025 | 0.1956 ± 0.0067 | 0.3151 ± 0.0063 |
| DHEA (10 mg) | 0.1465 ± 0.0010** | 0.2163 ± 0.0049* | 0.3408 ± 0.0038** |
| EM-800 (75 μg) | 0.1356 ± 0.0017 | 0.1888 ± 0.0045 | 0.3097 ± 0.0047 |
| DHEA + EM-800 | 0.1498 ± 0.0019** | 0.2108 ± 0.0061 | 0.3412 ± 0.0056** |

TABLE 3

Effect of treatment with DHEA (10 mg, percutaneously, once daily) or EM-800 (75 μg, orally, once daily) alone or in combination for 9 months on parameters of bone metabolism in the rat: daily urinary calcium and phosphorus excretion, urinary hydroxyproline to creatinine ratio (HP/Cr), and serum total alkaline phosphotase activity (tALP).
Samples were obtained from 9 animals per group.
$*p < 0.05$;
$**p < 0.01$ experimental versus control.

| GROUP | URINE | | | SERUM |
| --- | --- | --- | --- | --- |
| | CALCIUM (μmol/24 h/100 g) | PHOSPHORUS (μmol/24 h/100 g) | HP/Cr (μmol/mmol) | tALP (IU/L) |
| CONTROL | 23.17 ± 1.55 | 132.72 ± 6.08 | 13.04 ± 2.19 | 114.25 ± 14.04 |
| DHEA (10 mg) | 25.87 ± 3.54 | 151.41 ± 14.57 | 14.02 ± 1.59 | 198.38 ± 30.76* |
| EM-800 (75 μg) | 17.44 ± 4.5 | 102.03 ± 25.13 | 6.81 ± 0.84** | 114.11 ± 11.26 |
| DHEA + EM-800 | 3.71 ± 0.75** | 59.06 ± 4.76** | 4.06 ± 0.28** | 204.38 ± 14.20** |

Example 2

Abstract

In the mammary gland, androgens are formed from the precursor steroid dehydroepiandrosterone (DHEA). Clinical evidence indicates that androgens have inhibitory effects on breast cancer. Estrogens, on the other hand, stimulate the development and growth of breast cancer. We studied the effect of DHEA alone or in combination with the newly described pure antiestrogen, EM-800, on the growth of tumor xenografts formed by the human breast cancer cell line ZR-75-1 in ovariectomized nude mice.

Mice received daily subcutaneous injections of 0.5 μg estrone (an estrogenic hormone) immediately after ovariectomy. EM-800 (15, 50 or 100 μg) was given orally once daily. DHEA was applied twice daily (total dose 0.3, 1.0 or 3.0 mg) to the dorsal skin either alone or in combination with a 15 μg daily oral dose of EM-800. Changes in tumor size in response to the treatments were assessed periodically in relation to the measurements made on the first day. At the end of the experiments, tumors were dissected and weighed.

A 9.4-fold increase in tumor size in 9.5 months was observed in ovariectomized mice receiving estrone alone in comparison with mice not receiving estrone. Administration of 15, 50 or 100 μg EM-800 in estrone-supplemented ovariectomized led to inhibitions of 88%, 93%, and 94% in tumor size, respectively. DHEA, on the other hand, at doses of 0.3, 1.0 or 3.0 mg inhibited terminal tumor weight by 67%, 82%, and 85%, respectively. Comparable inhibitions in tumor size were obtained with a daily 15 μg oral dose of EM-800 with or without different doses of percutaneous DHEA.

DHEA and EM-800 independently suppressed the growth of estrone-stimulated ZR-75-1 mouse xenograft tumors in nude mice. Administration of DHEA at the defined doses does not alter the inhibitory effect of EM-800.

Materials and Methods

ZR-75-1 Cells

ZR-75-1 human breast cancer cells were obtained from the American Type Culture Collection (Rockville, Md.) and routinely cultured as monolayers in RPMI 1640 medium supplemented with 2 mM L-glutamine, 1 mM sodium pyruvate, 100 IU penicillin/ml, 100 μg streptomycin/ml, and 10% fetal bovine serum, under a humidified atmosphere of 95% air/5% $CO_2$ at 37° C. as described (Poulin and Labrie, Cancer Res. 46: 4933-4937, 1986; Poulin et al., Breast Cancer Res. Treat. 12: 213-225, 1988). Cells were passaged weekly after treatment with 0.05% trypsin:0.02% EDTA (w/v). The cell cultures used for the experiments described in this report were derived from passage 93 of the cell line ZR-75-1.

Animals

Female homozygous Harlan Sprague-Dawley (nu/nu) athymic mice (28- to 42-day-old) were obtained from HSD (Indianapolis, Ind., USA). Mice were housed in vinyl cages with air filter tops in laminar air flow hoods and maintained under pathogen-limited conditions. Cages, bedding, and food were autoclaved before use. Water was autoclaved, acidified to pH 2.8, and provided ad libitum.

Cell Inoculation

Mice were bilaterally ovariectomized (OVX) one week before tumor cell inoculation under anesthesia achieved by intraperitoneal injection of 0.25 ml/animal of Avertin (amylic alcohol: 0.8 g/100 ml 0.9% NaCl; and tribromo ethanol: 2 g/100 ml 0.9% NaCl). $1.5 \times 10^6$ ZR-75-1 cells in logarithmic growth phase were harvested after the treatment of monolayer with 0.05% trypsin/0.02% EDTA (w/v), were suspended in 0.1 ml of culture medium containing 25% Matrigel and were inoculated subcutaneously on both flanks of the animals using a 1 inch-long 20-gauge needle as described previously (Dauvois et al., Cancer Res. 51: 3131-3135, 1991). In order to facilitate growth of the tumors, each animal received daily subcutaneous injection of 10 μg of estradiol ($E_2$) in vehicle composed of 0.9% NaCl 5% ethanol 1% gelatin for 5 weeks. After appearance of palpable ZR-75-1 tumors, tumor diameter was measured with calipers and mice having tumor diameter between 0.2 and 0.7 cm were selected for this study.

Hormonal Treatment

All animals, except those in the control OVX group, received daily subcutaneous injections of 0.5 μg estrone ($E_1$) in 0.2 ml of 0.9% NaCl 5% ethanol 1% gelatin. In the indicated groups, DHEA was administered percutaneously twice daily at the doses of 0.3, 1.0 or 3.0 mg/animal applied in a volume of 0.02 ml on the dorsal skin area outside the area of tumor growth. DHEA was dissolved in 50% ethanol 50% propylene glycol. EM-800, ((+)-7-pivaloyloxy-3-(4'-pivaloyloxyphenyl)-4-methyl-2-(4"-(2"'-piperidinoethoxy)phenyl)-2H-benzopyran), was synthesized as described earlier (Gauthier et al., J. Med. Chem. 40: 2117-2122, 1997) in the medicinal chemistry division of the Laboratory of Molecular Endocrinology of the CHUL Research Center. EM-800 was dissolved in 4% (v/v) ethanol 4% (v/v) polyethylene glycol (PEG) 600 1% (w/v) gelatin 0.9% (w/v) NaCl. Animals of the indicated groups received daily oral doses of 15 µg, 50 µg, or 100 µg of EM-800 alone or in combination with DHEA while animals of the OVX group received the vehicle (0.2 ml 4% ethanol 4% PEG 600 1% gelatin 0.9% NaCl) alone. Tumors were measured once a week with Vernier calipers. Two perpendicular diameters in cms (L and W) were recorded and tumor area (cm$^2$) was calculated using the formula: $L/2 \times W/2 \times \pi$ (Dauvois et al., Cancer Res. 51: 3131-3135, 1991). The area measured on the first day of treatment was taken as 100% and changes in tumor size were expressed as percentage of initial tumor area. In case of subcutaneous tumors in general, it is not possible to accurately access three dimensional volume of tumor, therefore, only tumors areas were measured. After 291 days (or 9.5 months) of treatment, the animals were sacrificed.

The categories of responses were evaluated as described (Dauvois et al., Breast Cancer Res. Treat. 14: 299-306, 1989; Dauvois et al., Eur. J. Cancer Clin. Oncol. 25: 891-897, 1989; Labrie et al., Breast Cancer Res. Treat. 33: 237-244, 1995). In short, partial regression corresponds to the tumors that regressed equal to or more than 50% of their original size; stable response refers to tumors that regressed less than 50% of the original size or progressed less than 50% of their original size, while complete regression refers to those tumors that were undetectable at the end of treatment. Progression refers to tumors that progressed more than 50% compared with their original size. At the end of the experiment, all animals were killed by decapitation. Tumors, uterus, and vagina were immediately removed, freed from connective and adipose tissues, and weighed.

Statistical Analysis

Statistical significance of the effects of treatments on tumor size was assessed using an analysis of variance (ANOVA) evaluating the effects due to DHEA, EM-800, and time, and repeated measures in the same animals performed at the initiation and at the end of the treatment (subjects within group factor). The repeated measures at time 0 and after 9.5 months of treatment constitute randomized blocks of animals. The time is thus analyzed as a within-block effect while both treatments are assessed as between-block effects. All interactions between main effects were included in the model. The significance of the treatment factors and of their interactions was analyzed using the subjects within group as the error term. Data were log-transformed. The hypotheses underlying the ANOVA assumed the normality of the residuals and the homogeneity of variance.

A posteriori pairwise comparisons were performed using Fisher's test for least significant difference. Main effects and the interaction of treatments on body weight and organ weight were analyzed using a standard two-way ANOVA with interactions. All ANOVAs were performed using SAS program (SAS Institute, Cary, N.C., USA). Significance of differences were declared using a 2-tailed test with an overall level of 5%.

Categorical data were analyzed with a Kruskall-Wallis test for ordered categorical response variables (complete response, partial response, stable response, and progression of tumor). After overall assessment of a treatment effects, subsets of the results presented in Table 4 were analyzed adjusting the critical p-value for multiple comparisons. The exact p-values were calculated using StatXact program (Cytel, Cambridge, Mass., USA).

Data are expressed as means±standard error of the mean (SEM) of 12 to 15 mice in each group.

Results

Figure 4A:
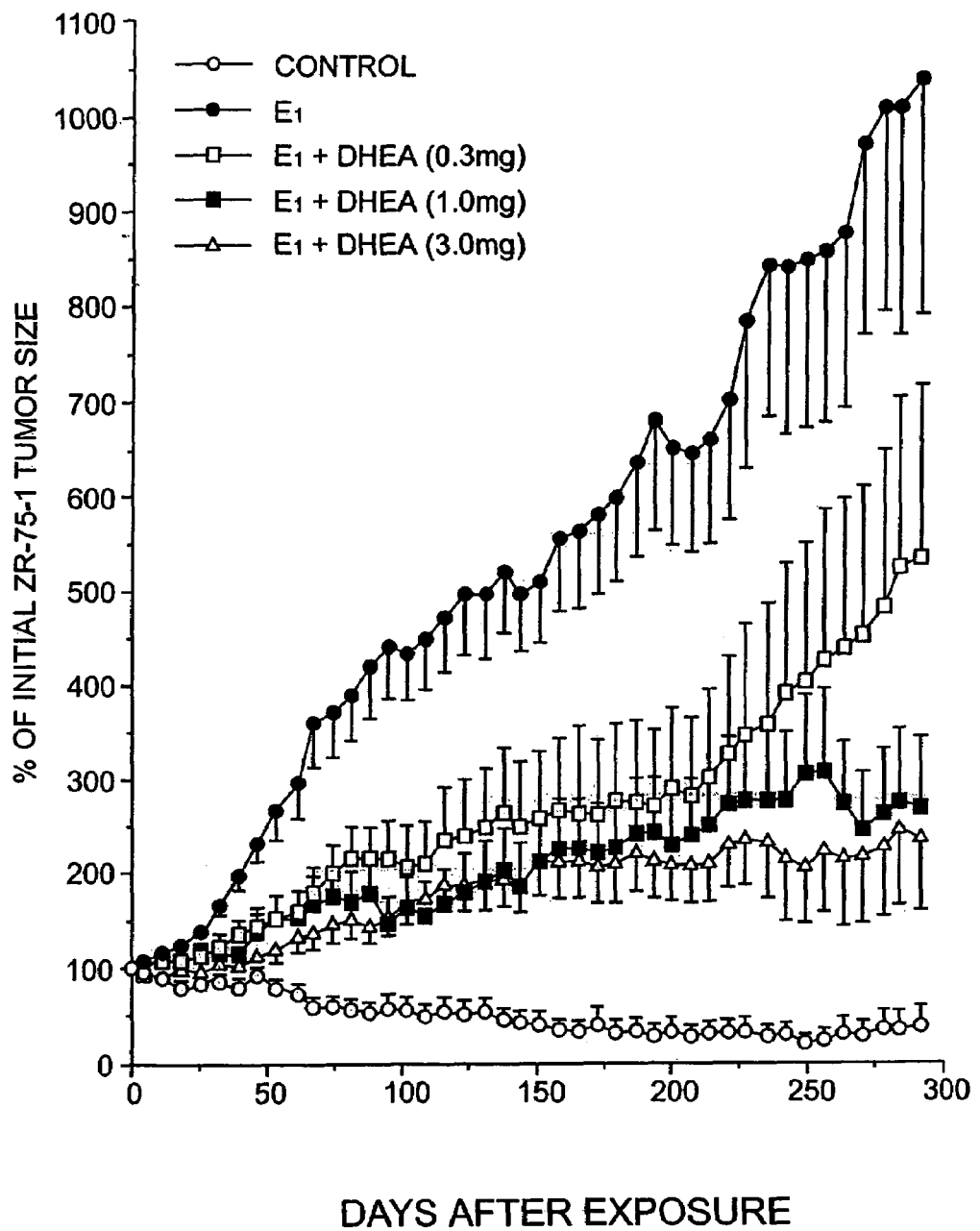
FIG. 4 shows: A) Effect of increasing doses of DHEA (0.3 mg, 1.0 mg or 3.0 mg) administered percutaneously twice daily on average ZR-75-1 tumor size in ovariectomized (OVX) nude mice supplemented with estrone. Control OVX mice receiving the vehicle alone are used as additional controls. The initial tumor size was taken as 100%. DHEA was administered percutaneously (p.c.) in a 0.02 ml solution of 50% ethanol–50% propylene glycol on the dorsal skin. B) Effect of treatment with increasing doses of DHEA or EM-800 alone or in combination for 9.5 months on ZR-75-1 tumor weight in OVX nude mice supplemented with estrone. **, p<0.01, treated versus control OVX mice supplemented with estrone.
Figure 5A:
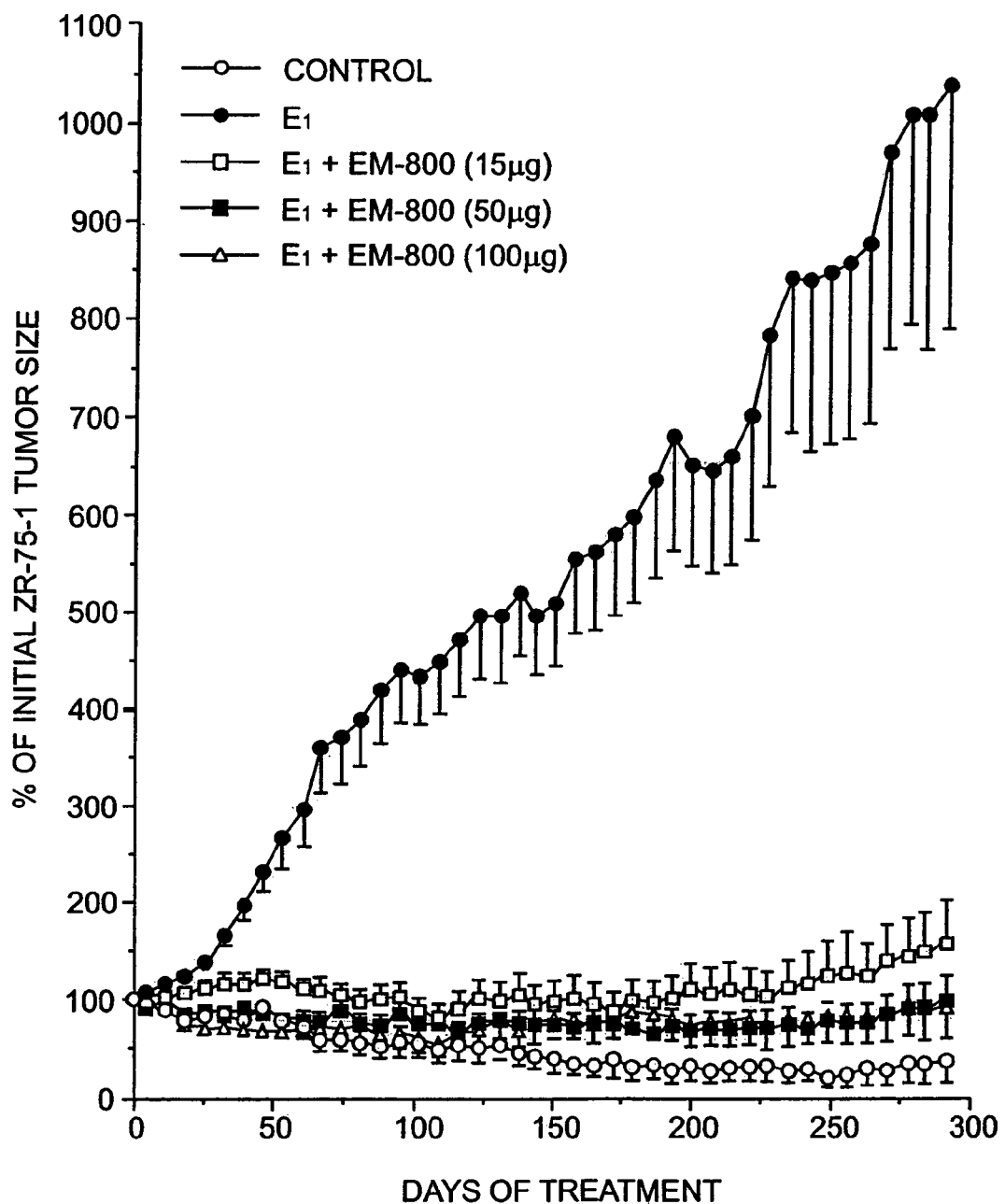
FIG. 5 shows the effect of increasing oral doses of the antiestrogen EM-800 (15 μg, 50 μg or 100 μg) (A) or of percutaneous administration of increasing doses of DHEA (0.3, 1.0 or 3.0 mg) combined with EM-800 (15 μg) or EM-800 alone (B) for 9.5 months on average ZR-75-1 tumor size in ovariectomized(OVX) nude mice supplemented with estrone. The initial tumor size was taken as 100%. Control OVX mice receiving the vehicle alone were used as additional controls. Estrone was administered subcutaneously at the dose of 0.5 μg once daily while DHEA was dissolved in 50% ethanol–50% propylene glycol and applied on the dorsal skin area twice daily in a volume of 0.02 ml. Comparison is also made with OVX animals receiving the vehicle alone.

As illustrated in FIG. 4A, human ZR-75-1 tumors increased by 9.4-fold over 291 days (9.5 months) in ovariectomized nude mice treated with a daily 0.5 µg subcutaneously administered dose of estrone while in control OVX mice who received the vehicle alone, tumor size was decreased to 36.9% of the initial value during the course of the study.

Figure 4B:
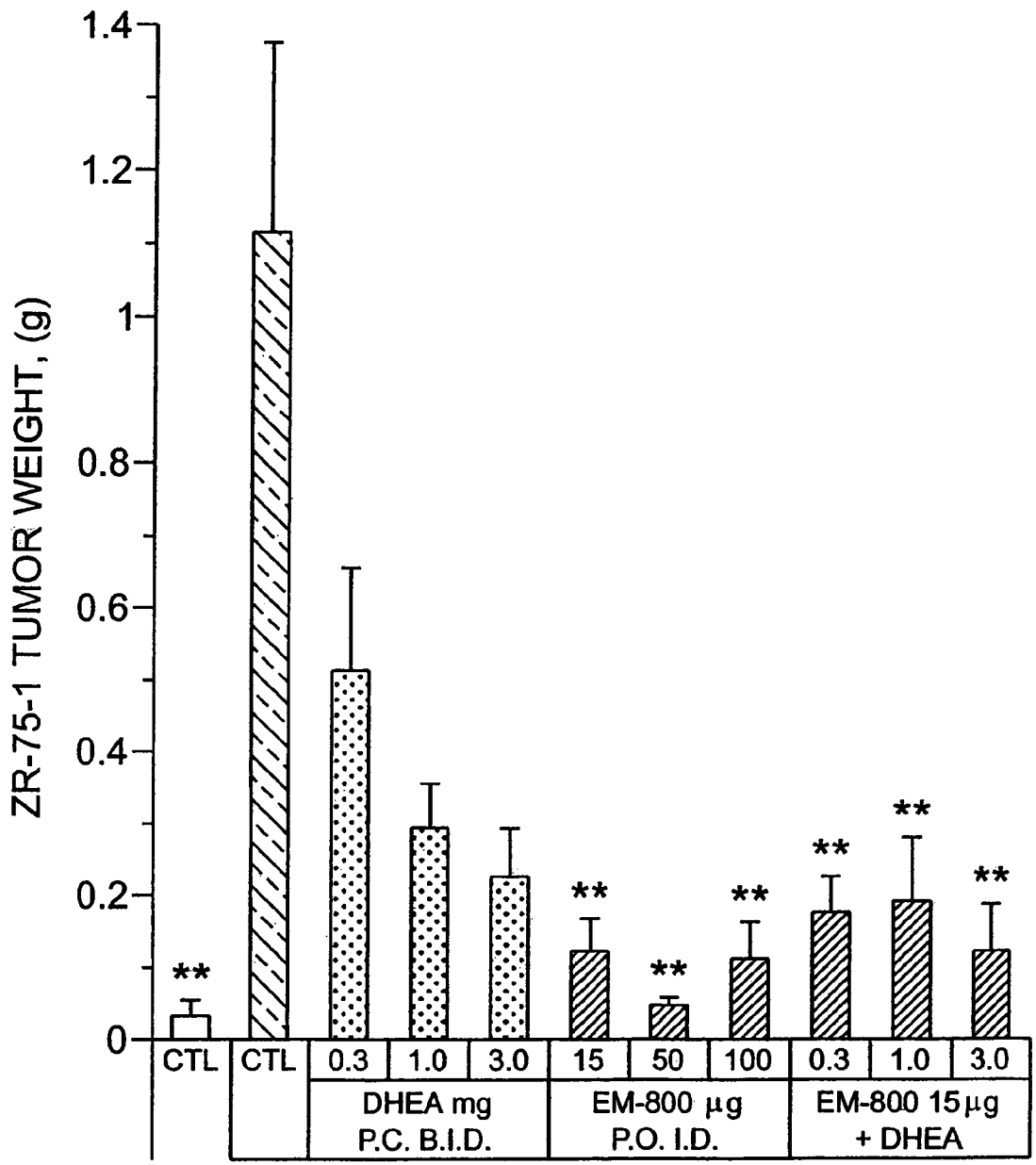

Treatment with increasing doses of percutaneous DHEA caused a progressive inhibition of $E_1$-stimulated ZR-75-1 tumor growth. Inhibitions of 50.4%, 76.8%, and 80.0% were achieved at 9.5 months of treatment with the 0.3 mg, 1.0 mg, and 3.0 mg daily doses per animal of DHEA, respectively (FIG. 4A). In agreement with the decrease in total tumor load, treatment with DHEA led to a marked decrease of the average weight of the tumors remaining at the end of the experiment. In fact, average tumor weight decreased from 1.12±0.26 g in control $E_1$-supplemented ovariectomized nude mice to 0.37±0.12 g (P=0.005), 0.20±0.06 g (P=0.001), and 0.17±0.06 g (P=0.0009) in the groups of animals receiving the daily 0.3, 1.0 and 3.0 mg doses of DHEA, respectively (FIG. 4B).

At the daily doses of 15 µg, 50 µg, and 100 µg, the antiestrogen EM-800 inhibited estrogen-stimulated tumor size by 87.5% (P<0.0001), 93.5% (P<0.0001), and 94.0% (P=0.0003), respectively (FIG. 5A) when compared to the tumor size in control animals at 9.5 months. The tumor size reductions achieved with the three EM-800 doses are not significantly different between each other. As illustrated in FIG. 4B, tumor weight at the end of the 9.5-month study was decreased from 1.12±0.26 g in control $E_1$-supplemented OVX mice to 0.08±0.03 g, 0.03±0.01 g and 0.04±0.03 g in animals treated with the daily 15 µg, 50 µg, and 100 µg doses of EM-800, respectively (P<0.0001 at all doses of EM-800 vs $E_1$ supplemented OVX).

Figure 5B:
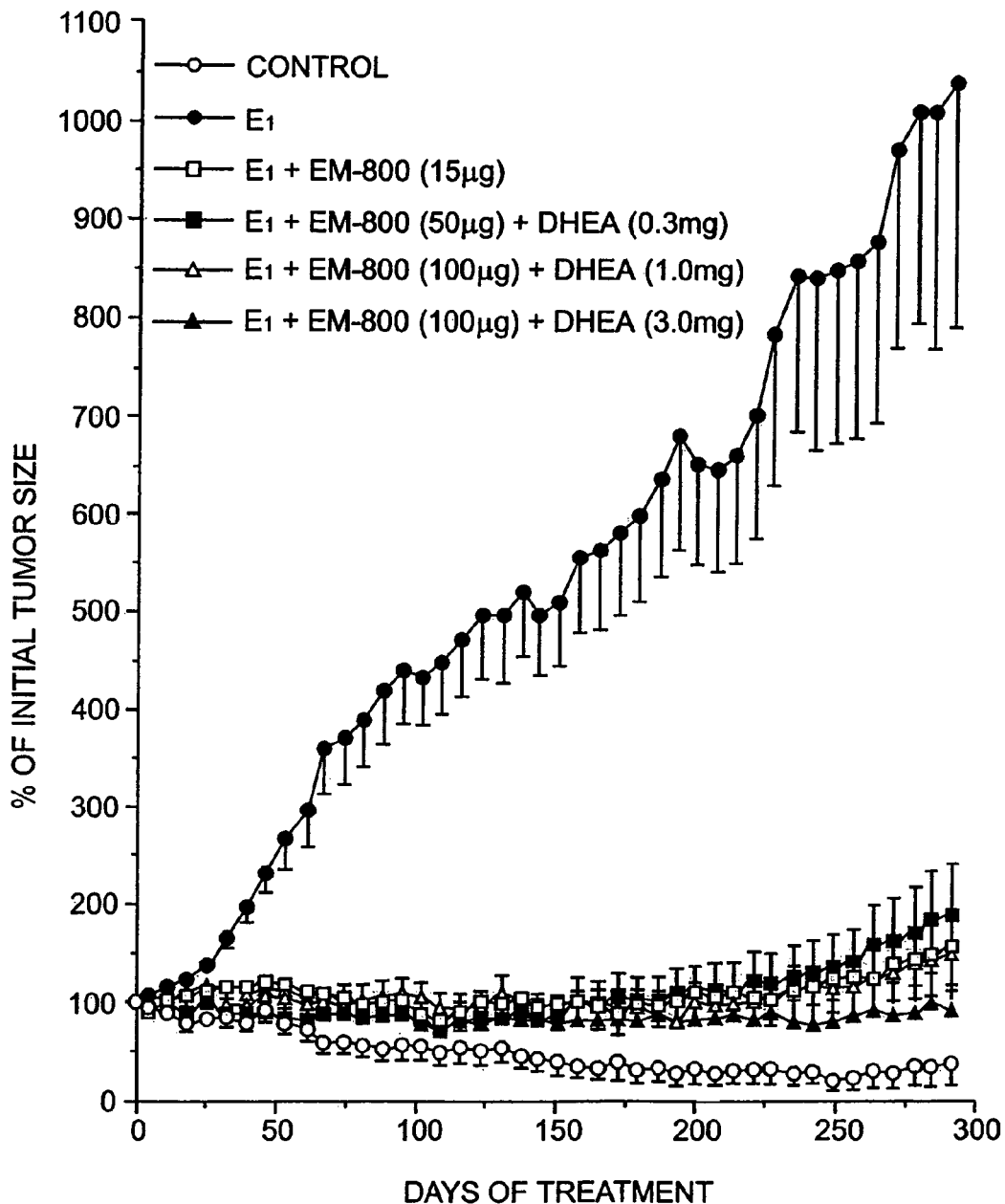

As mentioned above, the antiestrogen EM-800, at the daily oral dose of 15 µg, caused a 87.5% inhibition of estrone-stimulated tumor growth measured at 9.5 months. The addition of DHEA at the three doses used had no significant effect on the already marked inhibition of tumor size achieved with the 15 µg daily dose of the antiestrogen EM-800 (FIG. 5B). Thus, average tumor weight was dramatically reduced from 1.12±0.26 g in control estrone-supplemented mice to 0.08±0.03 g (P<0.0001), 0.11±0.04 g (P=0.0002), 0.13±0.07 g (P=0.0004) and 0.08±0.05 g (P<0.0001) in the animals who received the daily dose of 15 µg of the antiestrogen alone or in combination with the 0.3, 1.0, and 3.0 mg doses of DHEA, respectively (no significant difference was noted between the 4 groups) (FIG. 4B).

It was also of interest to examine the categories of responses achieved with the above-indicated treatments. Thus, treatment with the increasing doses of DHEA decreased, although not to a level of statistical significance (P=0.088), the number of progressing tumors from 87.5% in the control OVX animals supplemented with estrone to values of 50.0%, 53.3%, and 66.7% in the animals treated with the daily doses of 0.3, 1.0 or 3.0 mg of DHEA (Table 4). Complete responses, on the other hand, increased from 0% in the estrone-supplemented mice to 28.6%, 26.7%, and 20.0% in the animals receiving the 0.3, 1.0, and 3.0 mg daily doses of percutaneous DHEA. Stable responses, on the other hand, were measured at 12.5%, 21.4%, 20.0%, and 13.3% in the control $E_1$-supplemented mice and in the three groups of animals who received the above-indicated doses of DHEA, respectively. In control ovariectomized mice, the rates of complete, partial and stable responses were measured at 68.8%, 6.2%, and 18.8%, respectively, while progression was seen in only 6.2% of tumors (Table 4).

Complete responses or disappearance of the tumors were achieved in 29.4%, 33.3%, 26.7%, and 35.3% of tumors in the animals who received the antiestrogen EM-800 (P=0.0006) alone (15 μg) or in combination with the 0.3 mg, 1.0 mg, or 3.0 mg of DHEA, respectively (Table 4). Progression, on the other hand, was seen in 35.3%, 44.4%, 53.3%, and 17.6% of the tumors, in the same groups of animals, respectively. There is no significant difference between the groups treated with EM-800, either alone or in combination with DHEA.

No significant effect of DHEA or EM-800 treatment was observed on body weight adjusted for tumor weight. Treatment of OVX mice with estrone, increased uterine weight from 28±5 mg in OVX control mice to 132±8 mg (P<0.01) while increasing doses of DHEA caused a progressive but relatively small inhibition of the stimulatory effect of estrone which reached 26% (P=0.0008) at the highest dose of DHEA used. It can be seen in the same figure that estrone-stimulated uterine weight was decreased from 132±8 mg in control estrone-supplemented mice to 49±3 mg, 36±2 mg, and 32±1 mg (P<0.0001 at all doses vs control) with the daily oral doses of 15 μg, 50 μg, or 100 μg of EM-800 (overall P<0.0001), respectively. Fifteen micrograms (15 μg) EM-800 in combination with the 0.3 mg, 1.0 mg or 3.0 mg daily doses of DHEA, uterine weight was measured at 46±3 mg, 59±5 mg and 69±3 mg, respectively.

On the other hand, treatment with estrone increased vaginal weight from 14±2 mg in OVX animals to 31±2 mg (P<0.01) while the addition of DHEA had no significant effect. Vaginal weight was then reduced to 23±1 mg, 15±1 mg, and 11±1 mg following treatment with the daily 15 Mg, 50 μg or 100 μg doses of EM-800, respectively (overall p and pairwise P<0.0001 at all doses vs control). In combination with the 0.3 mg, 1.0 mg or 3.0 mg doses of DHEA and of EM-800, vaginal weight was measured at 22±1 mg, 25+2 mg and 23±1 mg, respectively (N.S. for all groups versus 15 μg EM-800). It should be mentioned that at the highest dose used, namely 100 μg daily, EM-800 decreased uterine weight in estrone-supplemented OVX animals to a value not different from that of OVX controls while vaginal weight was reduced to a value below that measured in OVX controls (P<0.05). DHEA, probably due to its androgenic effects, partially counteracted the effect of EM-800 on uterine and vaginal weight.

TABLE 4

Effect of percutaneous administration of DHEA or oral administration of EM-800 alone or in combination for 9.5 months on the responses (complete, partial, stable, and progression) of human ZR-75-1 breast tumor xenografts in nude mice.

| GROUP | TOTAL NUMBER OF ANIMALS | CATEGORY OF RESPONSE | | | |
|---|---|---|---|---|---|
| | | Complete | Partial | Stable | Progression |
| | | | Number and (%) | | |
| OVX | 16 | 11(68.8) | 1(6.2) | 3(18.8) | 1(6.2) |
| OVX + E1 (0.5 μg) | 16 | 0(0) | 0(0) | 2(12.5) | 14(87.5) |
| OVX + E1 (0.5 μg) + DHEA | | | | | |
| 0.3 mg | 14 | 4(28.6) | 0(0) | 3(21.4) | 7(50.0) |
| 1.0 mg | 15 | 4(26.7) | 0(0) | 3(20.0) | 8(53.3) |
| 3.0 mg | 15 | 3(20.0) | 0(0) | 2(13.3) | 10(66.7) |
| OVX + E1 (0.5 μg) + EM-800 | | | | | |
| 15 μg | 17 | 5(29.4) | 1(5.9) | 5(29.4) | 6(35.3) |
| 50 μg | 16 | 4(25.0) | 3(18.8) | 5(31.2) | 4(25.0) |
| 100 μg | 16 | 8(50.0) | 0(0) | 3(18.8) | 5(31.2) |
| OVX + E1 (0.5 μg) + EM-800 + DHEA | | | | | |
| 0.3 mg | 18 | 6(33.3) | 0(0) | 4(22.2) | 8(44.4) |
| 1.0 mg | 15 | 4(26.7) | 0(0) | 3(20.0) | 8(53.3) |
| 3.0 mg | 17 | 6(35.3) | 0(0) | 8(47.1) | 3(17.6) |

$E_1$ = Estrone;
DHEA = dehydroepiandrosterone;
OVX = ovariectomized

Example 3

Effect of the Preferred Compound of the Invention on Cholesterol Levels of Female Ovariectomized Rats Animals and Treatment Fifty to 60 day-old female Sprague-Dawley rats (Crl:CD (SD)Br) (Charles River Laboratory, St-Constant, Canada) weighing approximately 190 g at the time of ovariectomy were used. The animals were acclimated to the environmental conditions (temperature: 22±3° C.; humidity: 50±20%; 12-h light-12-h dark cycles, lights on at 07:15 h) for 1 week before the surgery. The animals were housed three per cage and were allowed free access to tap water and a pelleted certified rodent feed (Lab Diet 5002, Ralston Purina, St-Louis, Mo.). The experiment was conducted in a Canadian Council on Animal Care approved facility in accordance with the CCAC Guide for Care and Use of Experimental Animals.

One hundred thirty-six female rats were ovariectomized under Isoflurane anesthesia on day 0 of the study and were randomly distributed into 17 groups of animals to conduct the study outlined below:
Group 1: OVX CONT
Group 2: OVX+EM-800 (0.01 mg/kg, po, ID)
Group 3: OVX+EM-800 (0.03 mg/kg, po, ID)
Group 4: OVX+EM-800 (0.1 mg/kg, po, ID)
Group 5: OVX+EM-800 (0.3 mg/kg, po, ID)
Group 6: OVX+EM-800 (1 mg/kg, po, ID)
Group 7: OVX+EM-01538 (0.01 mg/kg, po, ID)
Group 8: OVX+EM-01538 (0.03 mg/kg, po, ID)
Group 9: OVX+EM-01538 (0.1 mg/kg, po, ID)
Group 10: OVX+EM-01538 (0.3 mg/kg, po, ID)
Group 11: OVX+EM-01538 (1 mg/kg, po, ID)
Group 12: OVX+Raloxifene (EM-1105) (0.01 mg/kg, po, ID)
Group 13: OVX+Raloxifene (EM-1105) (0.03 mg/kg, po, ID)
Group 14: OVX+Raloxifene (EM-1105) (0.1 mg/kg, po, ID)
Group 15: OVX+Raloxifene (EM-1105) (0.3 mg/kg, po, ID)
Group 16: OVX+Raloxifene (EM-1105) (1 mg/kg, po, ID)
Group 17: INT CONT The administration of treatments were started on day 10 of the study and were given by oral gavage once daily until day 13 of the study. Dosing suspensions were prepared in 0.4% methylcellulose and the concentration was adjusted according to the mean body weight of the group recorded on day 10 of the study in order to give 0.5 ml of dosing suspension per rat. Approximately 24 hours after the last dosing, overnight faster animals were killed by exsanguination at the abdominal aorta under isoflurane anesthesia and blood samples were processed for serum preparation. The uteri were removed, stripped of remaining fat and weighed.

Serum Cholesterol and Triglyceride Assays

Total serum cholesterol and triglyceride levels were determined using the Boehringer Mannheim Diagnostic Laboratory Systems).

Example 4

Androstene-3β,17β-diol (5-diol) possesses intrinsic estrogenic activity. In addition, as a precursor sex steroid, it can be transformed into active androgens and/or other estrogens in peripheral intracrine tissues. In order to assess the relative importance of the androgenic and estrogenic components of 5-diol action on bone mass, twenty-one week old rats were ovariectomized and treated percutaneously once daily with 2, 5, or 12.5 mg of 5-diol alone or in combination with the antiandrogen Flutamide (FLU, 10 mg, s.c., once daily), and/or the antiestrogen EM-800 (100 µg, s.c., once daily) for 12 months. Bone mineral density (BMD) was measured after 11 months of treatment. Ovariectomy (OVX) led to a 12.8% decrease in femoral BMD ($p<0.01$) while treatment with the highest dose of 5-diol restored 34.3% of femoral BMD lost during the 11 months following OVX ($p<0.01$). Simultaneous administration of FLU completely prevented the stimulatory effect of 5-diol on femoral BMD while the addition of EM-800 resulted in an additional 28.4% stimulation compared to the effect of 5-diol alone. The simultaneous administration of 5-diol, FLU, and EM-800 only displayed the effect of EM-800 (27%) since the effect of 5-diol was completely blocked by FLU. Comparable results were obtained on BMD of lumbar spine although lumbar spine BMD in OVX rats receiving 12.5 mg 5-diol alone, 12.5 mg 5-diol+ EM-800 or 5-diol+FLU+EM-800 was restored to values not significantly different from those of intact animals. The histomorphometric analysis shows that the stimulatory effects of 5-diol on bone volume, trabecular number and the inhibitory effect on trabecular separation of secondary spongiosa of the proximal tibia metaphyseal area are abolished by FLU, but further enhanced by EM-800. The marked stimulation of serum alkaline phosphatase activity obtained following the treatment with 5-diol is 57% ($p<0.01$ vs 12.5 mg 5-diol alone) reversed by the simultaneous administration of FLU. Treatment with 5-diol had no statistically significant inhibitory effect on the urinary ratio of calcium to creatinine. The highest dose of 5-diol caused a significant 23% ($p<0.01$) reduction of serum cholesterol while the addition of EM-800 decreased serum cholesterol by 62% ($p<0.01$). The present data clearly show the stimulatory effect of 5-diol on bone formation and suggest that although 5-diol is a weak estrogen, its stimulatory effect on bone formation is predominantly mediated by an androgenic effect. Moreover, the additive stimulatory effects of EM-800 and 5-diol on bone mass demonstrate the bone-sparing effect of the anti-estrogen EM-800 in the rat. The cholesterol-lowering activity of both 5-diol and EM-800 could have interesting utility for the prevention of cardiovascular diseases.

Example 5

| Group | Serum Alkaline phosphatase IU/L | Urinary OH-proline/ creatinin µmol/mmol | LH ng/ml | GnRH mRNA levels silver grains per cell | Cholesterol mmol/L | Triglycerides mmol/L |
| --- | --- | --- | --- | --- | --- | --- |
| Intact Control | 30 ± 3** | 15.4 ± 1.3 | 0.09 ± 0.03** | 33.7 ± 0.7** | 2.28 ± 0.12 | 1.4 ± 0.2 |
| OVX Control | 51 ± 4 | 11.7 ± 1.2 | 3.55 ± 0.50 | 44.0 ± 0.9 | 2.29 ± 0.16 | 1.1 ± 0.1 |
| OVX + MPA | 57 ± 4 | 11.7 ± 1.2 | 2.51 ± 0.20* | 35.5 ± 0.7** | 2.55 ± 0.14 | 1.3 ± 0.1 |
| OVX + E$_2$ | 41 ± 5 | 9.2 ± 0.9 | 2.37 ± 0.45* | 40.4 ± 0.8** | 2.02 ± 0.15 | 0.8 ± 0.1 |
| OVX + DHT | 56 ± 5 | 7.8 ± 0.7* | 1.55 ± 0.27** | 38.8 ± 0.7** | 2.44 ± 0.16 | 0.9 ± 0.1 |
| OVX + DHEA | 201 ± 25** | 7.3 ± 1.0* | 0.02 ± 0.01** | 34.5 ± 0.7** | 1.78 ± 0.16* | 0.8 ± 0.1 |
| OVX + DHEA + FLU | 103 ± 10** | 14.5 ± 1.2 | 1.13 ± 0.24** | 41.5 ± 0.7* | 2.27 ± 0.15 | 0.8 ± 0.1 |
| OVX + DHEA + EM-800 | 202 ± 17** | 6.4 ± 1.0** | LD** | 39.2 ± 0.7** | 0.63 ± 0.09** | 1.0 ± 0.2 |

LD: Limit of Detection: 0.01 ng/ml
*$p < 0.05$;
**$p < 0.01$ versus OVX Control

Example 6
Example of Synthesis of the Preferred Compound of the Invention
Synthesis of (S)-(+)-7-hydroxy-3-(4'-hydroxyphenyl)-4-methyl-2-(4''-(2'''-piperidinoethoxy)phenyl)-2H-1-benzopyran hydrochloride EM-01538 (EM-652, HCl)
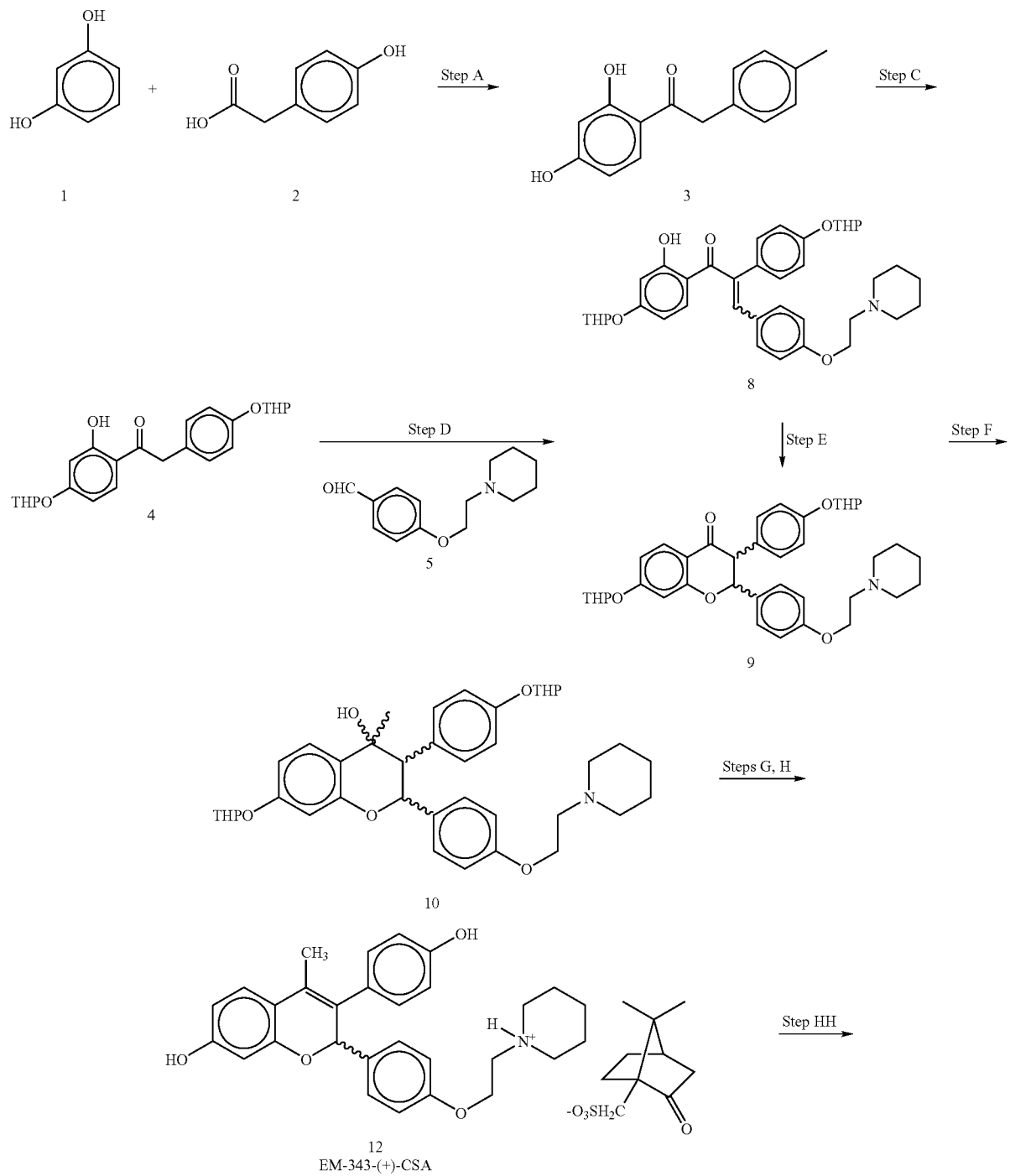

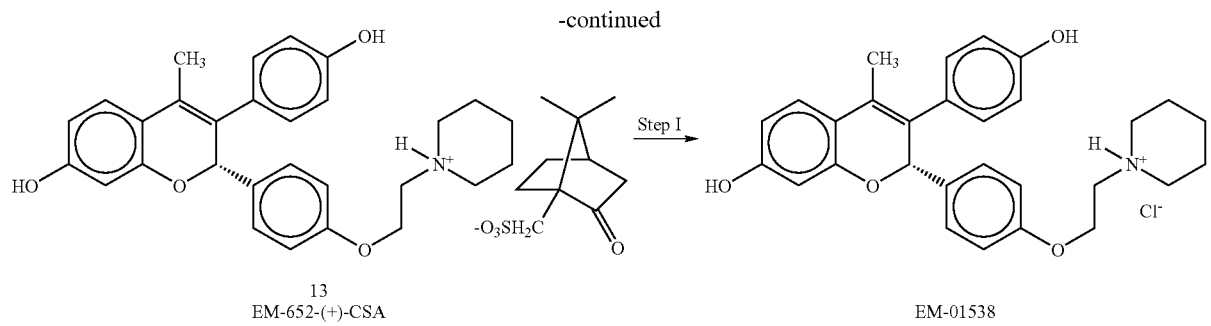

13
EM-652-(+)-CSA

EM-01538

Step A: BF$_3$.Et$_2$O, toluene; 100° C.; 1 hour.

Step C: 3,4-dihydropyran, p-toluenesulfonic acid monohydrate, ethyl acetate; 25° C. under nitrogen, 16 hours, and then crystallization in isopropanol.

Steps D, E, and F:
(1) piperidine, toluene, Dean & Stark apparatus, reflux under nitrogen; (2) 1,8-diazabicyclo[5, 4, 0]undec-7-ene, DMF, reflux 3 hours;
(3) CH$_3$MgCl, THF, −20 to 0° C. and then room temperature for 24 hours;

Steps G, H: (1S)-(+)-10-camphorsulfonic acid, acetone, water, toluene, room temperature, 48 hours.

Step HH: 95% ethanol, 70° C., then room temperature 3 days.

Step HHR: Recycling of mother liquor and wash of step HH (S)-10-camphorsulfonic acid, reflux; 36 hours, then room temperature for 16 hours.

Step I:
(1) DMF aq., Na$_2$CO$_3$, ethyl acetate;
(2) ethanol, dilute HCl;
(3) water.

Synthesis of 2-tetrahydropyranyloxy-4-hydroxy-2'-(4"-tetrahydropyranyloxyphenyl) acetophenone (4). A suspension of 2,4-dihydroxy-2'-(4"-hydroxyphenyl)acetophenone 3 (97.6 g, 0.4 mole) (available from Chemsyn Science Laboratories, Lenexa, Kans.) in 3,4-dihydropyran (218 ml, 3.39 mole) and ethyl acetate (520 ml) was treated with p-toluenesulfonic acid monohydrate (0.03 g, 0.158 mmole) at about 25° C. The reaction mixture was stirred under nitrogen with no external heating for about 16 hours. The mixture was then washed with a solution of sodium bicarbonate (1 g) and sodium chloride (5 g) in water (100 ml). The phases were separated and the organic phase was washed with brine (20 ml). Each wash was back extracted with 50 ml ethyl acetate. All the organic phases were combined and filtered through sodium sulfate.

Solvent (about 600 ml) was removed by distillation at atmospheric pressure and isopropanol (250 ml) was added. Additional solvent (about 300 ml) was distilled at atmospheric pressure and isopropanol (250 ml) was added. Additional solvent (about 275 ml) was distilled at atmospheric pressure and isopropanol (250 ml) was added. The solution was cooled at about 25° C. with stirring and after about 12 hours, the crystalline solid was filtered, washed with isopropanol and dried (116.5 g, 70%).

Synthesis of 4-hydroxy-4-methyl-2-(4'-[2"-piperidino]-ethoxy)phenyl-3-(4'"-tetrahydropyranyloxy)phenyl-7-tetrahydropyranyloxy-chromane (10). A solution of 2-tetrahydropyranyloxy-4-hydroxy-2'-(4"-tetrahydropyranyloxyphenyl)acetophenone 4 (1 kg, 2.42 mole), 4-[2-(1-piperidino)ethoxy]benzaldehyde 5 (594 g, 2.55 mole) (available from Chemsyn Science Laboratories, Lenexa, Kans.) and piperidine (82.4 g, 0.97 mole) (available from Aldrich Chemical Company Inc., Milwaukee, Wis.) in toluene (8L) was refluxed under nitrogen with a Dean & Stark apparatus until one equivalent of water (44 mL) was collected.

Toluene (6.5 L) was removed from the solution by distillation at atmospheric pressure. Dimethylformamide (6.5 L) and 1,8-diazabicyclo[5,4,0]undec-7-ene (110.5 g, 0.726 mole) were added. The solution was agitated for about 8 hours at room temperature to isomerize the chalcone 8 to chromanone 9 and then added to a mixture of water and ice (8 L) and toluene (4 L). The phases were separated and the toluene layer washed with water (5 L). The combined aqueous washes were extracted with toluene (3×4 L). The combined toluene extracts were finally washed with brine (3×4 L), concentrated at atmospheric pressure to 5.5 L and then cooled to −10° C.

With continued external cooling and stirring under nitrogen, a 3M solution of methylmagnesium chloride in THF (2.5 L, 7.5 mole) (available from Aldrich Chemical Company Inc., Milwaukee, Wis.) was added, maintaining the temperature below 0° C. After all the Grignard reagent was added, the external cooling was removed and the mixture allowed warm to room temperature. The mixture was stirred at this temperature for about 24 hours.

The mixture was again cooled to about −20° C. and with continued external cooling and stirring, saturated ammonium chloride solution (200 ml) was added slowly, maintaining the temperature below 20° C. The mixture was stirred for 2 hours and then added the saturated ammonium chloride solution (2L) and toluene (4 L) and agitated for five minutes. The phases were separated and the aqueous layer extracted with toluene (2×4L). The combined toluene extracts were washed with dilute hydrochloric acid until the solution became homogenous and then with brine (3×4 L). The toluene solution was finally concentrated at atmospheric pressure to 2L. This solution was used directly in the next step.

Synthesis of (2R,S)-7-hydroxy-3-(4'-hydroxyphenyl)-4-methyl-2-(4"-[2'"-piperidino]ethoxy)phenyl)-2H-1-benzopyran (1S)-10-camphorsulphonic acid salt (±12). To the toluene solution of 4-hydroxy-4-methyl-2-(4'-[-2"-piperidino]-ethoxy)-phenyl-3-(4'"-tetrahydropyranyloxy)phenyl-7-tetrahydropyranyloxychromane (10) was added acetone (6 L), water (0.3 L) and (S)-10-camphorsulphonic acid (561 g, 2.42 mole) (available from Aldrich Chemical Company Inc., Milwaukee, Wis.). The mixture was agitated under nitrogen for 48 hours after which time the solid (2R,S)-7-hydroxy-3-(4'-hydroxyphenyl)-4-methyl-2-(4"-[2'"-piperidino]ethoxy)

phenyl)-2H-1-benzopyran (1S)-10-camphorsulphonic acid salt (12) was filtered, washed with acetone and dried (883 g). This material was used in the next (HH) step without further purification.

Synthesis of (2S)-7-hydroxy-3-(4'-hydroxyphenyl)-4-methyl-2-(4"-[2'''-piperidino]ethoxy)phenyl)-2H-1-benzopyran (1S)-10-camphorsulphonic acid salt (13, (+)-EM-652(1S)-CSA salt). A suspension of (2R,S)-7-hydroxy-3-(4'-hydroxyphenyl)-4-methyl-2-(4"-[2'''-piperidino]ethoxy)phenyl)-2H-benzopyran (1S)-10-camphorsulphonic acid salt ±12 (759 g) in 95% ethanol was heated with stirring to about 70° C. until the solid had dissolved. The solution was allowed to cool to room temperature with stirring then seeded with a few crystals of (2S)-7-hydroxy-3-(4'-hydroxyphenyl)-4-methyl-2-(4"-[2'''-piperidino]ethoxy)phenyl)-2H-1-benzopyran (1S)-10-camphorsulphonic acid salt 13. The solution was stirred at room temperature for about three days in total. The crystals were filtered, washed with 95% ethanol and dried (291 g, 76%). The de of the product was 94.2% and the purity 98.8%.

Synthesis of (S)-(+)-7-hydroxy-3-(4'-hydroxyphenyl)-4-methyl-2-(4"-(2'''-piperidinoethoxy)phenyl)-2H-1-benzopyran hydrochloride EM-01538 (EM-652, HCl). A suspension of compound 13 (EM-652-(+)—CSA salt, 500 mg, 0.726 mmol) in dimethylformamide (11 μL, 0.15 mmol) was treated with an 0.5 M aqueous sodium carbonate solution (7.0 mL, 3.6 mmol), and stirred for 15 min. The suspension was treated with ethyl acetate (7.0 mL) and stirred during 4 h. The organic phase was then washed with an aqueous saturated sodium carbonate solution (2×5 mL) and brine (1×5 mL) dried over magnesium sulfate, and concentrated. A solution of the resulting pink foam (EM-652) in ethanol (2 mL) was treated with 2 N hydrochloric acid (400 μL, 0.80 mmol), stirred for 1 h, treated with distilled water (5 mL), and stirred during 30 min. The resulting suspension was filtered, washed with distilled water (5 mL), dried in air and under high vacuum (65° C.) to give a creamy powder (276 mg, 77%): Fine off-white powder; Scanning Calorimetry: Melting peak onset at 219° C., ΔH=83 J/g; $[\alpha]^{24}_D$=154° in methanol 10 mg/ml.; $^1$H NMR (300 MHz, CD$_3$OD) δ (ppm) 1.6 (broad, 2H, H-4'''), 1.85 (broad, 4H, H-3'''' and 5''''), 2.03 (s, 3H, CH$_3$), 3.0 and 3.45 (broad, 4H, H-2'''' and 6''''), 3.47 (t, J=4.9 Hz, 2H, H-3'''), 4.26 (t, J=4.9 Hz, 2H, H-2'''), 5.82 (s, 1H, H-2), 6.10 (d, J=2.3 Hz, 1H, H-8), 6.35 (dd, J=8.4, 2.43 Hz, 1H, H-6), 6.70 (d, J=8.6 Hz, 2H, H-3', and H-5'), 6.83 (d, J=8.7 Hz, 2H, H-3" and H-5"), 7.01 (d, J=8.5 Hz, 2H, H-2' and H-6'), 7.12 (d, J=8.4 Hz, 1H, H-5), 7.24 (d, J=8.6 Hz, 2H, H-2" and H-6"); 13C RMN (CD$_3$OD, 75 MHz) δ ppm 14.84, 22.50, 23.99, 54.78, 57.03, 62.97, 81.22, 104.38, 109.11, 115.35, 116.01, 118.68, 125.78, 126.33, 130.26, 130.72, 131.29, 131.59, 134.26, 154.42, 157.56, 158.96, 159.33. Elemental Composition: C; H, N, Cl: Theory; 70.51, 6.53, 2.84, 7.18, %, Found: 70.31, 6.75, 2.65, 6.89%.

Example 7

In Vivo Assays of Bioavailability of the Prodrugs of Androst-5-ene-3β,17β-diol

1) Principle

The assays of the bioavailability of prodrugs of sex steroid precursors were performed in male Sprague Dawley rats by measuring the plasma concentrations of the compounds after single oral administration of the compounds.

a) Animals and Treatment

Male Sprague-Dawley rats [Crl:CD(SD)Br] weighing 275-350 g were obtained from Charles-River Canada Inc. and housed 2 per cage during the acclimation period and individually during the study period. The animals were maintained under a regimen of 12 hours light: 12 hours dark (lights on at 08:00). Animals received certified Rodent feed (Lab Diet # 5002, pellets) and tap water ad libitum. Rats were fasted (access to water only) starting on the evening prior to dosing.

Each compound to be tested was administered to three animals as a suspension in 0.4% methylcellulose by oral gavage at a dose of 150 μmg/rat. One blood sample of ~0.7 ml was collected from the jugular vein of rats under Isoflurane-induced anesthesia at 1, 2, 3, 4, and 7 hours post-gavage. Blood samples were immediately transferred into a refrigerated 0.75 ml Microtainer containing EDTA and kept in an ice-water bath until centrifugation at 3000 rpm for 10 minutes. Plasma separation was performed rapidly (less than 50 minutes) after blood collection. One aliquot of 0.25 ml of plasma was then transferred into a borosilicate tube (13×100) and was rapidly frozen on dry-ice. Plasma samples were kept at −80° C. until measurement of plasma concentration of the sex steroid or sex steroid precursors by GC-MS.

Figure 12:
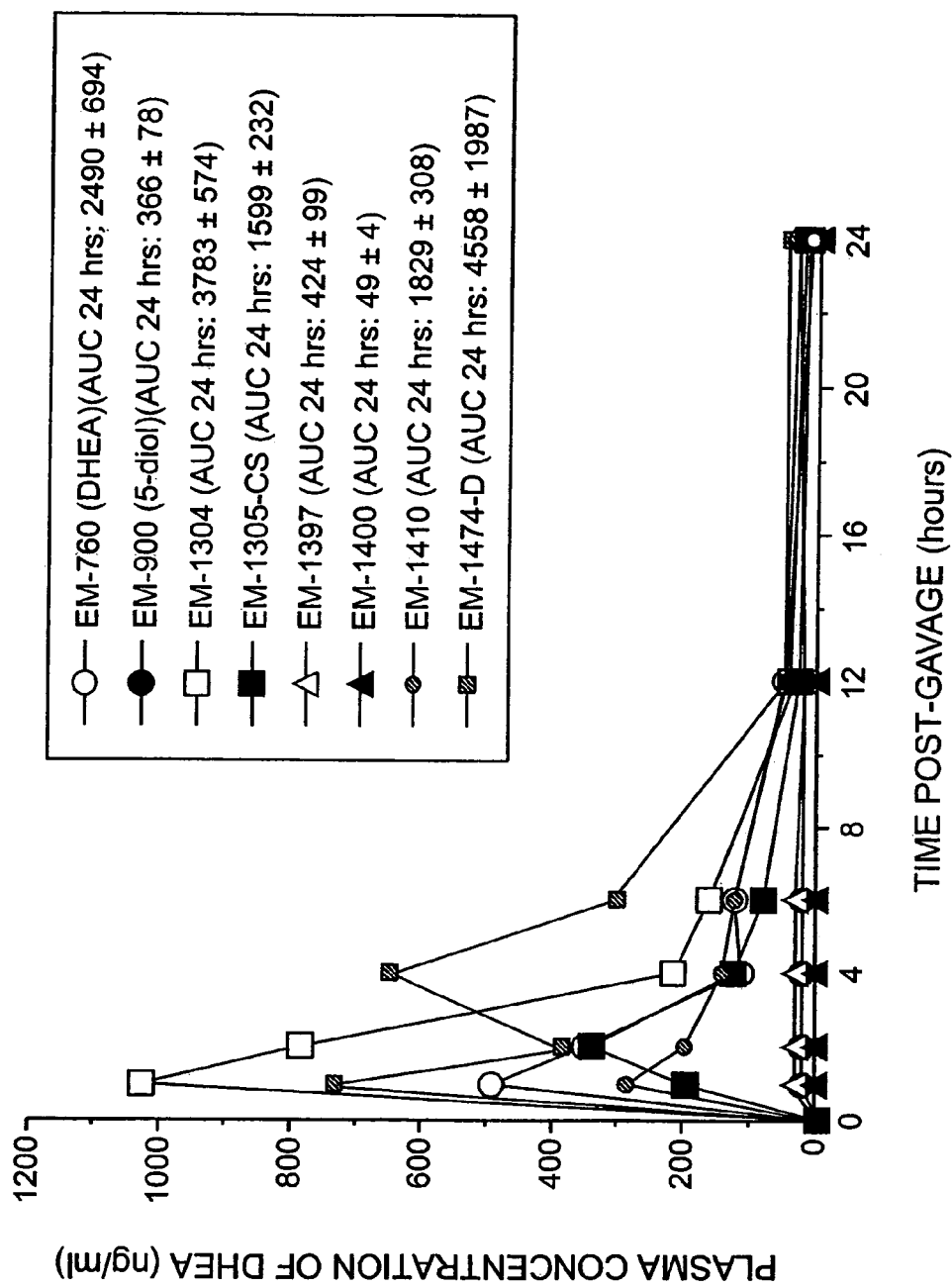
FIG. 12 shows the plasma concentration of DHEA (ng/mL) (Y axis) in function of time (X-axis) after a single oral absorption of preferred sex steroid precursors of the invention(150 μmol/rat) in male rats. In the box, AUC 24 h of DHEA induced by these compounds is reported. EM-760 dehydroepiandrosterone EM-900 androst-5-ene-3β,17β-diol EM-1304 androst-5-ene-3β,17β-diol 3-acetate EM-1305-CS androst-5-ene-3β,17β-diol diacetate EM-1397 androst-5-ene-3β,17β-diol 3 acetate 17 benzoate EM-1400 androst-5-ene-3β,17β-diol dibenzoate EM-1410 androst-5-ene-3β, 17β-diol dipropionate EM-1474-D androst-5-ene-3β,17β-diol dihemisuccinate
Figure 13:
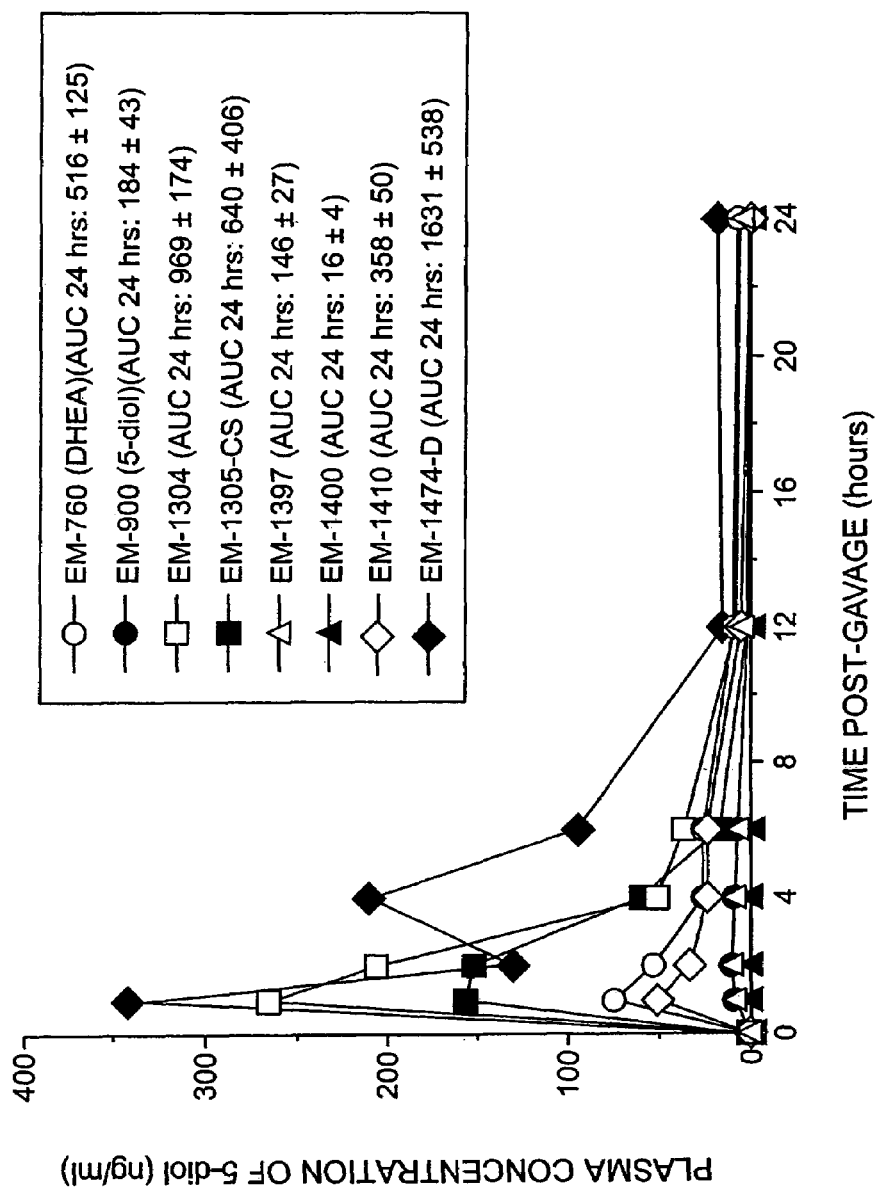
FIG. 13 shows the plasma concentration of androst-5-ene-3β,17β-diol (ng/mL) (Y axis) in function of time (X-axis) after a single oral absorption of sex steroid precursor of the invention(150 μmol/rat) in male rats. In the box, AUC 24 h of androst-5-ene-3β,17β-diol induced by these compounds is reported. EM-760 dehydroepiandrosterone EM-900 androst-5-ene-3β,17β-diol EM-1304 androst-5-ene-3β,17β-diol 3-acetate EM-1305-CS androst-5-ene-3β, 17β-diol diacetate EM-1397 androst-5-ene-3β,17β-diol 3 acetate 17 benzoate EM-1400 androst-5-ene-3β,17β-diol dibenzoate EM-1410 androst-5-ene-3β,17β-diol dipropionate EM-1474-D androst-5-ene-3β,17β-diol dihemisuccinate

Results:

Oral absorption and AUCs are shown in FIGS. 12 and 13.

Pharmaceutical Composition Examples

Set forth below, by way of example and not of limitation, are several pharmaceutical compositions utilizing preferred active SERM EM-800 or EM-1538 and preferred active a sex steroid precursor DHEA, EM-1304 or EM-01474-D Other compounds of the invention or combination thereof, may be used in place of (or in addition to) EM-800 or EM-1538, DHEA, EM-1304 or EM-01474-D. The concentration of active ingredient may be varied over a wide range as discussed herein. The amounts and types of other ingredients that may be included are well known in the art.

Example A

Tablet

| Ingredient | Weight % (by weight of total composition) |
| --- | --- |
| EM-800 | 5.0 |
| DHEA | 15.0 |
| Gelatin | 5.0 |
| Lactose | 58.5 |
| Starch | 16.5 |

Example B

Gelatin Capsule

| Ingredient | Weight % (by weight of total composition) |
| --- | --- |
| EM-800 | 5.0 |
| DHEA | 15.0 |
| Lactose hydrous | 65.0 |

-continued

| Ingredient | Weight % (by weight of total composition) |
|---|---|
| Starch | 4.8 |
| Cellulose microcrystalline | 9.8 |
| Magnesium stearate | 0.4 |

Kit Examples

Set forth below, by way of example and not of limitation, are several kits utilizing preferred active SERM EM-800 or EM-1538 and preferred active a sex steroid precursor DHEA, EM-1304 or EM-01474-D Other compounds of the invention or combination thereof, may be used in place of (or in addition to) EM-800 or EM-1538, DHEA, EM-1304 or EM-01474-D. The concentration of active ingredient may be varied over a wide range as discussed herein. The amounts and types of other ingredients that may be included are well known in the art.

Example A

The SERM is orally administered while the sex steroid precursor is percutaneously administered SERM Composition for Oral Administration (Capsules)

| Ingredient | Weight % (by weight of total composition) |
|---|---|
| EM-800 | 5.0 |
| Lactose hydrous | 80.0 |
| Starch | 4.8 |
| Cellulose microcrystalline | 9.8 |
| Magnesium stearate | 0.4 |

Sex Steroid Precursor Composition for Topical Administration (Gel)

| Ingredient | Weight % (by weight of total composition) |
|---|---|
| DHEA | 10.0 |
| Caprylic-capric Triglyceride (Neobee M-5) | 5.0 |
| Hexylene Glycol | 15.0 |
| Transcutol (diethyleneglycol monomethyl ether) | 5.0 |
| Benzyl alcohol | 2.0 |
| Cyclomethicone (Dow corning 345) | 5.0 |
| Ethanol (absolute) | 56.0 |
| Hydroxypropylcellulose (1500 cps) (KLUCEL) | 2.0 |

Example B

The SERM and the sex steroid precursor are orally administered

Non-Steroidal Antiestrogen Composition for Oral Administration (Capsules)

| Ingredient | Weight % (by weight of total composition) |
|---|---|
| EM-800 | 5.0 |
| Lactose hydrous | 80.0 |
| Starch | 4.8 |
| Cellulose microcrystalline | 9.8 |
| Magnesium stearate | 0.4 |

Sex Steroid Precursor Composition for Oral Administration (Gelatin Capsule)

| Ingredient | Weight % (by weight of total composition) |
|---|---|
| DHEA | 15.0 |
| Lactose hydrous | 70.0 |
| Starch | 4.8 |
| Cellulose microcrystalline | 9.8 |
| Magnesium stearate | 0.4 |

Other SERMs may be substituted for EM-800 or EM-01538 in the above formulations, as well as other sex steroid inhibitors may be substituted for DHEA, EM-1304 or EM-01474-D. More than one SERM or more than one precursor may be included in which case the combined weight percentage is preferably that of the weight percentage for the single precursor or single SERM given in the examples above.

The invention has been described in terms of preferred embodiments and examples, but is not limited thereby. Those of skill in the art will readily recognize the broader applicability and scope of the invention which is limited only by the patent claims herein.

What is claimed is:

1. A method of treating or reducing vaginal dryness comprising increasing levels of a sex steroid precursor selected from the group consisting of dehydroepiandrosterone, dehydroepiandrosterone sulfate, androst-5-ene-3b,17b-diol and 4-androsten-3,17-dione, in a patient in need thereof by administering a therapeutically effective amount of the precursor and further comprising administering a therapeutically effective amount of a selective estrogen receptor modulator as part of a combination therapy.

* * * * *